US011578315B2

(12) United States Patent
Lavie et al.

(10) Patent No.: US 11,578,315 B2
(45) Date of Patent: Feb. 14, 2023

(54) TRUNCATED GUINEA PIG L-ASPARAGINASE VARIANTS AND METHODS OF USE

(71) Applicant: THE BOARD OF TRUSTEES OF THE UNIVERSITY OF ILLINOIS, Urbana, IL (US)

(72) Inventors: Arnon Lavie, Chicago, IL (US); Hien-Anh Nguyen, Chicago, IL (US); Amanda Schalk, Chicago, IL (US)

(73) Assignees: The Board of Trustees of the University of Illinois, Urbana, OH (US); The United States Government as represented by the Department of Veterans Affairs, Washington, DC (US)

( * ) Notice: Subject to any disclaimer, the term of this patent is extended or adjusted under 35 U.S.C. 154(b) by 4 days.

(21) Appl. No.: 16/637,070

(22) PCT Filed: Aug. 10, 2018

(86) PCT No.: PCT/US2018/046196
§ 371 (c)(1),
(2) Date: Feb. 6, 2020

(87) PCT Pub. No.: WO2019/032952
PCT Pub. Date: Feb. 14, 2019

(65) Prior Publication Data
US 2020/0239867 A1  Jul. 30, 2020

Related U.S. Application Data

(60) Provisional application No. 62/544,411, filed on Aug. 11, 2017, provisional application No. 62/544,396, filed on Aug. 11, 2017.

(51) Int. Cl.
| C12N 9/82 | (2006.01) |
| C12N 15/70 | (2006.01) |
| C12N 15/55 | (2006.01) |
| A61K 38/50 | (2006.01) |
| A61P 35/02 | (2006.01) |
| A61K 38/00 | (2006.01) |

(52) U.S. Cl.
CPC .............. *C12N 9/82* (2013.01); *A61P 35/02* (2018.01); *C12Y 305/01001* (2013.01); *A61K 38/00* (2013.01)

(58) Field of Classification Search
None
See application file for complete search history.

(56) References Cited

U.S. PATENT DOCUMENTS

2009/0131317 A1  5/2009  Angell et al.
2015/0337027 A1  11/2015  Hill et al.

FOREIGN PATENT DOCUMENTS

| EP | 0811687 A2 | 12/1997 |
| EP | 0726313 B1 | 1/2004 |
| JP | H10057080 A | 3/1998 |
| JP | 2010501191 A | 1/2010 |
| JP | 2015503333 A | 2/2015 |
| JP | 2016117718 A | 6/2016 |
| JP | 2017513503 A | 6/2017 |
| WO | 2012170640 A1 | 12/2012 |
| WO | 2015164588 A1 | 10/2015 |

OTHER PUBLICATIONS

Singh et al., Curr. Protein Pept. Sci. 18:1-11, 2017 (Year: 2017).*
Zhang et al., Structure 26:1474-1485, 2018 (Year: 2018).*
Rigouin et al., Sci. Reports 7:10224, 2017 (Year: 2017).*
Terpe, K., Appl. Microbiol. Biotechnol. 60:523-533, 2003 (Year: 2003).*
Meier et al., J. Mol. Biol. 344:1051-1069, 2004 (Year: 2004).*
"Supplementary Data", https://www.nature.com/articles/s41598-017-10758-4#additional-information, Aug. 31, 2017, 6 pages (Year: 2017).*
UniProt Database Accesssion No. A0A6P6DP48, Sep. 2021, 2 pages (Year: 2021).*
International Search Report and Written Opinion in PCT/US2018/046196 dated Oct. 19, 2018.
Karpel-Massler, G., D. Ramani, C. Shu, M.E. Halatsch, M.A. Westhoff, J.N. Bruce, P. Canoll & M.D. Siegelin (2016) "Metabolic reprogramming of glioblastoma cells by L-asparaginase sensitizes for apoptosis in vitro and in vivo," Oncotarget 7(23):33512-33528.
Kouno, M., C. Lin, N. Schechter, D. Siegel, X. Yang, J.T. Seykora & J.R. Stanley (2013) "Targeted delivery of tumor necrosis factor-related apoptosis-inducing ligand to keratinocytes with a pemphigus monoclonal antibody," J. Invest. Dermaol. 133(9):2212-2220.
Schalk, A.M., H.-A. Nguyen, c. Rigouin & A. Lavie (2014) "Identification and Structural Analysis of an L-Asparaginase Enzyme from Guinea Pig with Putative Tumor Cell Killing Properties," J. Biol. Chem. 289:33175-33186.
International Preliminary Report on Patentability in PCT/US2018/046196 dated Feb. 11, 2020.
Kouno, M., (May 24, 2016) "Development of the epidermis specific drug delivery system using nonpathogenic pemphigus antibodies," Scientific Research Grant Project, Report of the research results. Theme No. 25461713.
Tsutsumi, Y. & T. Mayumi (2003) "Creation of functional bioactive muteins using phage display technique results in a novel drug delivery system," Drug Delivery System 18(6):536-544.

\* cited by examiner

*Primary Examiner* — David Steadman
(74) *Attorney, Agent, or Firm* — Licata & Tyrrell P.C.

(57) ABSTRACT

Variant guinea pig L-asparaginases which are truncated and humanized are described as are fusion proteins containing the L-asparaginase and use of the L-asparaginases in the treatment of cancers such as acute lymphoblastic leukemia and acute myeloid leukemia.

15 Claims, 3 Drawing Sheets
Specification includes a Sequence Listing.

```
hASN   MARAVGPERRLLAVYTGGTIGMRSELGVLVPGTGLAAILRTLPMFHDEEH
GpA    MARASGSERHLLLIYTGGTLGMQSKGGVLVPGPGLVTLLRTLPMFHDKEF
hN-gC  MARAVGPERRLLAVYTGGTIGMRSELGVLVPGTGLAAILRTLPMFHDEEH
gN-hC  MARASGSERHLLLIYTGGTLGMQSKGGVLVPGPGLVTLLRTLPMFHDKEF
63-hC  MARASGSERHLLLIYTGGTLGMQSKGGVLVPGPGLVTLLRTLPMFHDKEF
64-hC  MARASGSERHLLLIYTGGTLGMQSKGGVLVPGPGLVTLLRTLPMFHDEEH
65-hC  MARASGSERHLLLIYTGGTLGMQSKGGVLVPGPGLVTLLRTLPMFHDEEH
SA-hC  MARASGSERHLLLIYTGGTLGMQSKGGVLVPGPGLVTLLRTLPMFHDEEH
       ****.*.**.**.:*****.**.*:.******.**.::*********:*.

hASN   ARARGLSEDTLVLPPASRNQRILYTVLECQPLFDSSDMTIAEWVCLAQTI
GpA    AQAQGLPDHALALPPASHGPRVLYTVLECQPLLDSSDMTIDDWIRIAKII
hN-gC  ARARGLSEDTLVLPPASRNQRILYTVLECQPLFDSSDMTIAEWVCLAQTI
gN-hC  AQAQGLPDHALALPPASHGPRVLYTVLECQPLLDSSDMTIDDWIRIAKII
63-hC  ARARGLSEDTLVLPPASRNQRILYTVLECQPLLDSSDMTIDDWIRIAKII
64-hC  ARARGLSEDTLVLPPASRNQRILYTVLECQPLLDSSDMTIDDWIRIAKII
65-hC  ARARGLSEDTLVLPPASRNQRILYTVLECQPLFDSSDMTIAEWVCLAQTI
SA-hC  ARARGLSEDTLVLPPASRNQRILYTVLECQPLLDSSDMTIDDWIRIAKII
       *.*.**.:.:*.*****..*:***********:****.:*:.:*:.* hASN   KRHYEQYHGFVVIHGTDTMAFAASMLSFMLENLQKTVILTGAQVPIHALW
GpA    ERHYEQYQGFVVIHGTDTMASGASMLSFMLENLHKPVILTGAQVPIRVLW
hN-gC  KRHYEQYHGFVVIHGTDTMAFAASMLSFMLENLQKTVILTGAQVPIHALW
gN-hC  ERHYEQYQGFVVIHGTDTMASGASMLSFMLENLHKPVILTGAQVPIRVLW
63-hC  ERHYEQYQGFVVIHGTDTMAFAASMLSFMLENLHKPVILTGAQVPIRVLW
64-hC  ERHYEQYQGFVVIHGTDTMAFAASMLSFMLENLHKPVILTGAQVPIHALW
65-hC  KRHYEQYHGFVVIHGTDTMAFAASMLSFMLENLHKPVILTGAQVPIHALW
SA-hC  ERHYEQYHGFVVIHGTDTMAFAASMLSFMLENLQKTVILTGAQVPIRVLW
       :******:***********..***********:*.**********..**

hASN   SDGRENLLGALLMAGQYVIPEVCLFFQNQLFRGNRATKVDARRFAAFCSP
GpA    NDARENLLGALLVAGQYIIPEVCLFMNSQLFRGNRVTKVDSQKFEAFCSP
hN-gC  SDGRENLLGALLMAGQYVIPEVCLFFQNQLFRGNRATKVDARRFAAFCSP
gN-hC  NDARENLLGALLVAGQYIIPEVCLFMNSQLFRGNRVTKVDSQKFEAFCSP
63-hC  NDARENLLGALLVAGQYIIPEVCLFMNSQLFRGNRVTKVDSQKFEAFCSP
64-hC  SDGRENLLGALLVAGQYIIPEVCLFMNSQLFRGNRVTKVDSQKFEAFCSP
65-hC  SDGRENLLGALLMAGQYVIPEVCLFFQNQLFRGNRATKVDARRFAAFCSP
SA-hC  NDARENLLGALLVAGQYIIPEVCLFMSNQLFRGNRATKVDARRFAAFCSP
       .:*******..:****::.**.**..:*.***** hASN   NLLPLATVGADITINRELVRKVDGKAGLVVHSSMEQDVGLLRLYPGIPAA
GpA    NLSPLATVGADVTIAWDLVRKVKWKDPLVVHSNMEHDVALLRLYPGIPAS
hN-gC  NLLPLATVGADITINRELVRKVDGKAGLVVHSSMEQDVGLLRLYPGIPAA
gN-hC  NLSPLATVGADVTIAWDLVRKVKWKDPLVVHSNMEHDVALLRLYPGIPAS
63-hC  NLSPLATVGADVTIAWDLVRKVKWKDPLVVHSSMEQDVGLLRLYPGIPAS
64-hC  NLSPLATVGADVTIAWDLVRKVKWKDPLVVHSSMEQDVGLLRLYPGIPAS
65-hC  NLLPLATVGADVTIAWDLVRKVKWKDPLVVHSNMEHDVALLRLYPGIPAA
SA-hC  NLSPLATVGADITINRELVRKVDGKAGLVVHSSMEQDVGLLRLYPGIPAA
       **.*********.**..:**.*****.*.****.**.**.**********:

hASN   LVRAFLQPPLKGVVMETFGSGNGPTKPDLLQELRVATERGLVIVNCTHCL
GpA    LVRAFLQPPLKGVVLETFGSGNGPSKPDLLQELRAAQRGLIMVNCSQCL
hN-gC  LVRAFLQPPLKGVVMETFGSGNGPTKPDLLQELRVATERGLVIVNCTHCL
gN-hC  LVRAFLQPPLKGVVLETFGSGNGPSKPDLLQELRAAERGLIMVNCSQCL
63-hC  LVRAFLQPPLKGVVLETFGSGNGPSKPDLLQELRAAERGLIMVNCSQCL
64-hC  LVRAFLQPPLKGVVMETFGSGNGPTKPDLLQELRAAERGLIMVNCSQCL
65-hC  LVRAFLQPPLKGVVLETFGSGNGPSKPDLLQELRAAERGLIMVNCSQCL
SA-hC  LVRAFLQPPLKGVVMETFGSGNGPTKPDLLQELRVATERGLVIVNCTHCL
       **************:********:*********..::***::***::**
```

*FI

```
hASN    QGAVTTDYAAGMAMAGAGVISGFDMTSEAALAKLSYVLGQPGLSLDVRKE
GpA     RGSVTPGYAT--SLAGANIVSGLDMTSEAALAKLSYVLGLPELSLERRQE
hN-gC   QGAVTTDYAAGMAMAGAGVISGFDMTSEAALAKLSYVLGQPGLSLDVRKE
gN-hC   RGSVTPGYAT--SLAGANIVSGLDMTSEAALAKLSYVLGLPELSLERRQE
63-hC   RGSVTPGYAT--SLAGANIVSGLDMTSEAALAKLSYVLGLPELSLERRQE
64-hC   RGSVTPGYAT--SLAGANIVSGLDMTSEAALAKLSYVLGLPELSLERRQE
65-hC   RGSVTPGYAT--SLAGANIVSGLDMTSEAALAKLSYVLGLPELSLERRQE
SA-hC   QGAVTTGYAT--SLAGANIVSGLDMTSEAALAKLSYVLGLPELSLERRQE
        .*:..:  ::*.:::***************.*.***:.*:* hASN    LLTKDLRGEMTPPSVEERRPSLQGNTLGGGVSWLLSLSGSQEADALRNAL
GpA     LLAKDLRGEMTLPTADLHQSSPPGSTLGQGVARLFSLFGCQEEDSVQDAV
hN-gC   LLTKDLRGEMTLPTADLHQSSPPGSTLGQGVARLFSLFGCQEEDSVQDAV
gN-hC   LLAKDLRGEMTPPSVEERRPSLQGNTLGGGVSWLLSLSGSQEADALRNAL
63-hC   LLAKDLRGEMTPPSVEERRPSLQGNTLGGGVSWLLSLSGSQEADALRNAL
64-hC   LLAKDLRGEMTPPSVEERRPSLQGNTLGGGVSWLLSLSGSQEADALRNAL
65-hC   LLAKDLRGEMTPPSVEERRPSLQGNTLGGGVSWLLSLSGSQEADALRNAL
SA-hC   LLAKDLRGEMTPPSVEERRPSLQGNTLGGGVSWLLSLSGSQEADALRNAL
        **:******** *:.:  ...*  *.*** **:.*:** *.** *:::*:

hASN    VPSLACAAAHAGDVEALQALVELGSDLGLVDFNGQTPLHAAARGGHTEAV
GpA     MPSLALALAHAGELEALQALMELGSDLRLKDSNGQTLLHVAARNGRDGVV
hN-gC   MPSLALALAHAGELEALQALMELGSDLRLKDSNGQTLLHVAARNGRDGVV
gN-hC   VPSLACAAAHAGDVEALQALVELGSDLGLVDFNGQTPLHAAARGGHTEAV
63-hC   VPSLACAAAHAGDVEALQALVELGSDLGLVDFNGQTPLHAAARGGHTEAV
64-hC   VPSLACAAAHAGDVEALQALVELGSDLGLVDFNGQTPLHAAARGGHTEAV
65-hC   VPSLACAAAHAGDVEALQALVELGSDLGLVDFNGQTPLHAAARGGHTEAV
SA-hC   VPSLACAAAHAGDVEALQALVELGSDLGLVDFNGQTPLHAAARGGHTEAV
        :****.* **::*:*** * * ** .***.*.  .* hASN    TMLLQRGVDVNTRDTDGFSPLLLAVRGRHPGVIGLLREAGASLSTQELEE
GpA     TMLLHRGMDVNARDRDGLSPLLLAVQGRHRECIRLLRKAGACLSPQDLKD
hN-gC   TMLLHRGMDVNARDRDGLSPLLLAVQGRHRECIRLLRKAGACLSPQDLKD
gN-hC   TMLLQRGVDVNTRDTDGFSPLLLAVRGRHPGVIGLLREAGASLSTQELEE
63-hC   TMLLQRGVDVNTRDTDGFSPLLLAVRGRHPGVIGLLREAGASLSTQELEE
64-hC   TMLLQRGVDVNTRDTDGFSPLLLAVRGRHPGVIGLLREAGASLSTQELEE
65-hC   TMLLQRGVDVNTRDTDGFSPLLLAVRGRHPGVIGLLREAGASLSTQELEE
SA-hC   TMLLQRGVDVNTRDTDGFSPLLLAVRGRHPGVIGLLREAGASLSTQELEE
        ****:**:***:**.**:*******.***:  *.**::***.**.::::**

hASN    AGTELCRLAYRADLEGLQVWWQAGADLGQPGYDGHSALHVAEAAGNLAVV
GpA     AGTELCRLASRADMEGLQAWGQAGADLQQPGYDGRSALCVAEAAGNQEVL
hN-gC   AGTELCRLASRADMEGLQAWGQAGADLQQPGYDGRSALCVAEAAGNQEVL
gN-hC   AGTELCRLAYRADLEGLQVWWQAGADLGQPGYDGHSALHVAEAAGNLAVV
63-hC   AGTELCRLAYRADLEGLQVWWQAGADLGQPGYDGHSALHVAEAAGNLAVV
64-hC   AGTELCRLAYRADLE-----------------------------------
65-hC   AGTELCRLAYRADLEGLQVWWQAGADLGQPGYDGHSALHVAEAAGNLAVV
SA-hC   AGTELCRLAYRADLEGLQVWWQAGADLGQPGYDGHSALHVAEAAGNLAVV
        *********.***:*
                                                       Identity to hASN
hASN    AFLQSLEGAVGAQAPCPEVLPGV   (SEQ ID NO:2)        100%
GpA     ALLRNL-ALVG-----PEVPPAI   (SEQ ID NO:1)        69.8%
hN-gC   ALLRNL-ALVG-----PEVPPAI   (SEQ ID NO:38)       86.5%
gN-hC   AFLQSLEGAVGAQAPCPEVLPGV   (SEQ ID NO:37)       83.4%
63-hC   AFLQSLEGAVGAQAPCPEVLPGV   (SEQ ID NO:39)       85.7%
64-hC   -----------------------   (SEQ ID NO:40)       87.1%
65-hC   AFLQSLEGAVGAQAPCPEVLPGV   (SEQ ID NO:41)       91.1%
SA-hC   AFLQSLEGAVGAQAPCPEVLPGV   (SEQ ID NO:42)       91.6%
```

*FIG. 2B*

TRUNCATED GUINEA PIG L-ASPARAGINASE VARIANTS AND METHODS OF USE

This patent application is a U.S. National Stage Application of PCT/US2018/046196 filed Aug. 10, 2018 and claims the benefit of priority of U.S. Provisional Application Nos. 62/544,396, filed Aug. 11, 2017, and 62/544,411, filed Aug. 11, 2017, the contents of which are incorporated herein by reference in their entireties.

This invention was made with government support under Grant Number EB013685 awarded by the National Institutes of Health and Grant Number BX001919 awarded by the Department of Veteran Affairs. The government has certain rights in the invention.

INTRODUCTION

Background

Certain cancers, such as acute lymphoblastic leukemia (ALL), are dependent upon scavenging Asn from blood, a factor most commonly attributed to the lack/low expression of asparagine synthetase in such cancers. Accordingly, L-asparaginases have been identified as critical components in the treatment of these cancers. All commercially available L-asparaginases have dual activities. The predominant one, the L-asparaginase activity, hydrolyzes the amino acid L-asparagine (Asn) into L-aspartic acid (Asp) and ammonia. The secondary activity is an L-glutaminase activity, which hydrolyze L-glutamine (Gln) to L-glutamic acid (Glu) and ammonia. For FDA-approved enzymes, e.g., ELSPAR® (enzyme obtained from *Escherichia coli*) and ERWINAZE® (enzyme obtained from *Erwinia chrysanthemi*), the L-glutaminase activity ranges from 2 to 10% of the primary L-asparaginase activity. Whereas the importance of the L-asparaginase activity of these drugs is accepted, there are conflicting reports as to the importance of L-glutaminase activity in killing leukemic cells. Moreover, the L-glutaminase activity has been associated with much of the clinical toxicity of L-asparaginases. In fact, toxic side effects of L-asparaginase treatment severely limit the use of this anticancer drug.

Another disadvantage to the use of bacterial enzymes as therapeutics is their immunogenicity, which can pose a direct threat to the patient due to hypersensitivity reactions, up to anaphylactic shock. Moreover, generated antibodies can inactivate and clear the enzyme drug, thus reducing or even eliminating its effectiveness. Methods have been developed to reduce these severe side effects, such as conjugation of the *E. coli* enzyme with polyethylene glycol (PEGylation) or deimmunization by mutation of residues 115, 118, 120, 123, 215, 219, 307 and 312 of the wild-type *E. coli* enzyme (WO 2012/075173 A2). However, alternative L-asparaginase preparations with reduced immunogenicity and reduced L-glutaminase activity are needed.

A guinea pig L-asparaginase has been purified and characterized from guinea pig serum (Zhang, et al. (1995) Comp. Biochem. Physiol. B Biochem. Mol. Biol. 112(4):607-12). The guinea pig enzyme, annotated as HOW0T5_CAVPO, exhibits antitumor activity, has a low $K_m$ value for asparagine and lacks L-glutaminase activity (Schalk, et al. (2014) *J. Biol. Chem.* 289:33175-33186). See also EP 0726313 B1 and U.S. Pat. No. 6,537,547.

Other approaches for treating cancer using L-asparaginase have included co-administration of the L-asparaginase with a TNF-related apoptosis-inducing ligand (TRAIL) agonist or TRAIL receptor agonist, e.g., three soluble TRAIL domains and an additional functional domain such as an antibody fragment. See US 2015/0337027; US 2009/0131317 and WO 2012/170640. In this respect, L-asparaginase has been shown to overcome resistance to both intrinsic apoptosis induced by the Bcl-2/Bcl-xL inhibitor, ABT263, and extrinsic apoptosis mediated by TRAIL in glioma cells that are resistant toward L-asparaginase single treatment (Karpel-Massler, et al. (2016) *Oncotarget* 7(23): 33512-28).

SUMMARY OF THE INVENTION

This invention provides a C-terminally truncated Guinea pig L-Asparaginase (GpA) variant sharing at least 85% sequence identity with residues 1 to 359 of SEQ ID NO:1. In some embodiments, the C-terminal truncation is at a position between 359 and 396 of SEQ ID NO:1. In certain embodiments, the C-terminal truncation is at position 369 of SEQ ID NO:1. In other embodiments, the truncated GpA variant further includes at least one amino acid substitution relative to SEQ ID NO:1, e.g., at position 7, 10, 23, 25, 48, 49, 52, 53, 54, 57, 58, 59, 60, 62, 92, 98, 101, 102, 106, 108, 121, 122, 134, 147, 193, 198, 217, 233, 236, 250, 257, 281, 301, 311, 340, 344, 360, 362, 363, 364, 365, 366, 367, or 368, or a combination thereof. In particular embodiments, the at least one amino acid substitution relative to SEQ ID NO:1 is H10R, Q23R, K25E, K48E, Q52R, Q54R, P57S, D58E, H59D, A60T, A62V, D91A, D92E, K98Q, E101K, Q108H, S121F, G122A, H134Q, R147H, K193R, C198A, C198S, C198V, D217E, N233S, H236Q, S250A, Q288E, R301Q, E344D, L360P, T362S, A363V, D364E, L365E, H366R, Q367R, or S368P, or a combination thereof. In still other embodiments, the at least one amino acid substitution relative to SEQ ID NO:1 includes: (a) a cysteine residue at position 49, 52, 225, 257, 281 or 340, or a combination thereof; or (b) a lysine residue at position 7, 53, 54, 57, 58, 98, 106, 233, 250, 257, 281, 311 or 340, or a combination thereof. Ideally, the variant has a catalytic activity equal to or greater than wild-type GpA. Optionally, the truncated GpA variant can further include a histidine tag, a SUMO tag, an albumin-binding domain, three tandem soluble domains of TRAIL (e.g., residues 115-281 of human TRAIL), or a combination thereof.

Nucleic acid molecules, expression vectors, host cells and pharmaceutical compositions containing the truncated GpA variant or fusion proteins are also provided, as are methods of treating cancer by administering to a subject in need of treatment an effective amount of the truncated GpA variant or fusion proteins, optionally in combination with a stable form of TRAIL.

BRIEF DESCRIPTION OF THE DRAWINGS

FIGS. 2A and 2B show an amino acid sequence alignment of hASNase1 (hASN), gpASNase1 (GpA), and select humanized clones. Underlined residues are residues derived from GpA.

DETAILED DESCRIPTION OF THE INVENTION

Figure 1:
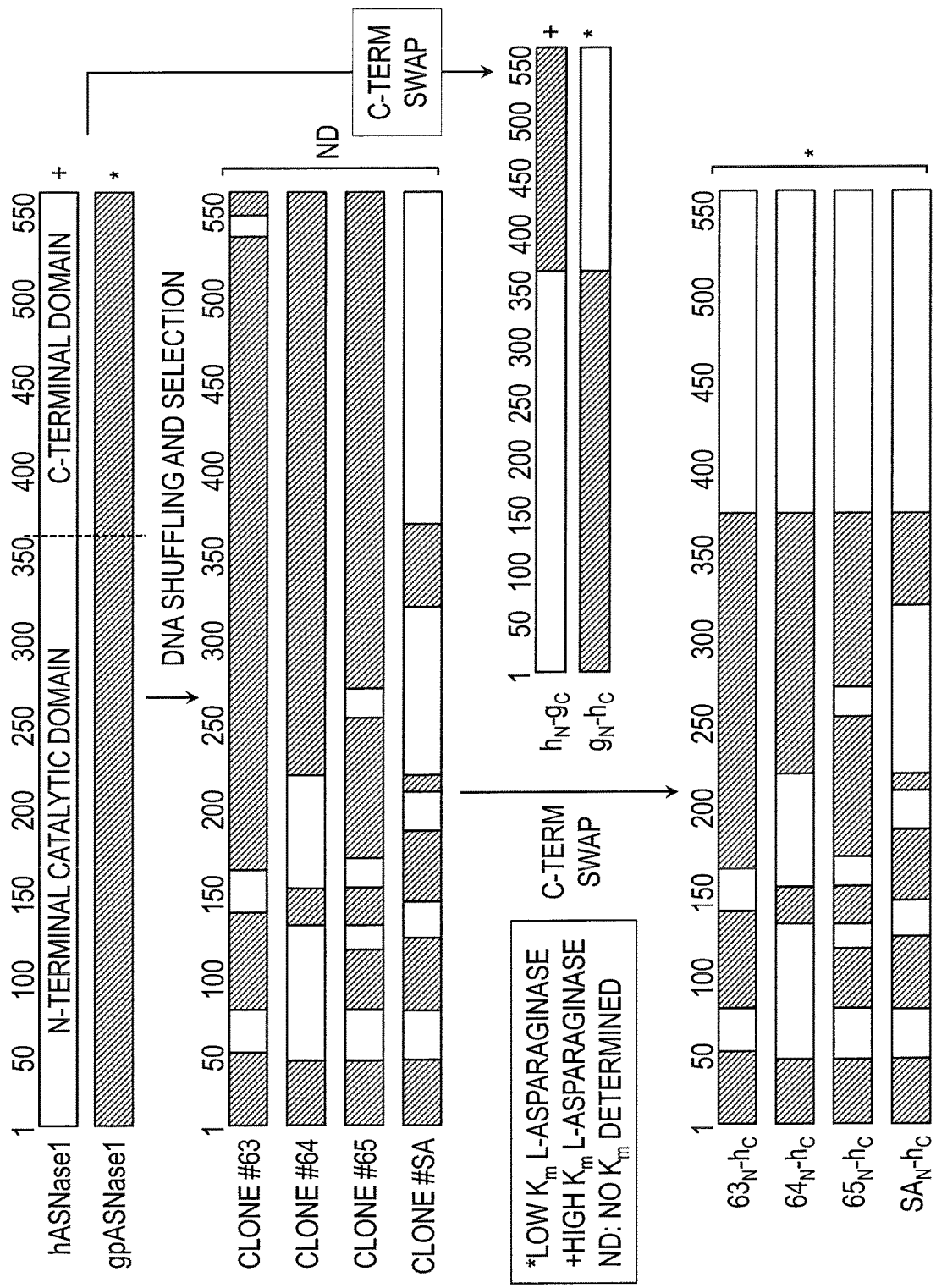
FIG. 1 is a schematic representation of the clones obtained from the DNA shuffling process and C-terminal domain swapping. hASNase1 sequences are open boxes, gpASNase1 is shaded boxes. Clones isolated from selection (#63, 64, 65 and SA) or generated by C-terminal swapping (63-hC, 64-hC, 65-hC and SA-hC) are a shuffle between hASNase1 (open boxes) and gpASNase1 (filled boxes) sequences.

L-asparaginase is a chemotherapy drug used to treat acute lymphoblastic leukemia (ALL). The main prerequisite for clinical efficacy of L-asparaginases is micromolar $K_m$ for asparagine to allow for complete depletion of this amino acid in the blood. Since currently approved L-asparaginases are of bacterial origin, immunogenicity is a challenge, which would be mitigated by a human enzyme. However, all human L-asparaginases have millimolar $K_m$ for asparagine. A low $K_m$ guinea pig L-asparaginase (gpASNase1) has been identified, which shares ~70% amino-acid identity with human L-asparaginase 1 (hASNase1). Like the human enzyme, gpASNase1 contains two domains; an N-terminal domain of ~360 residues where the L-asparaginase activity resides, and a C-terminal domain of ~200 residues of unknown function. To improve half-life, shorter yet stable versions of GpA were sought. Accordingly, GpA was C-terminally truncated to identify the shortest fragment of GpA that retained activity. This analysis indicated that the 359 amino acid residue N-terminal catalytic domain could be expressed with a SUMO tag and retained wild-type activity. However, upon removal of the SUMO tag, the protein became unstable. Extending the truncation to residue 369 provided both a stable and active enzyme.

To decrease the immunogenicity of the truncated GpA variant, two different approaches were taken to humanize the enzyme: DNA shuffling and structure-based mutation of surface residues. Humanization of GpA yielded variants sharing approximately 80% sequence identity with hASNase1, wild-type GpA activity, a low $K_m$ value for asparagine, and no detectable L-glutaminase activity. Upon introduction of cysteine or lysine residues and conjugation to PEG, the truncated GpA variants maintained, and in some instanced, exhibited an increase in their L-asparaginase activity. In addition, modifications such as N- or C-terminal addition of a histidine tag, SUMO tag, and/or albumin binding domain can increase in vivo circulation time and fusion of the truncated GpA variant to three tandem soluble domains of TRAIL can facilitate cell death by both providing the necessary signals for the intrinsic apoptotic cascade (L-asparaginase) and inducing the extrinsic apoptotic cascade (TRAIL).

Accordingly, this invention provides truncated GpA variants, and fusion proteins thereof, for use in the treatment of cancers such as lymphomas and leukemias, which are dependent upon the presence of an external supply of Asn. The improved safety of the instant L-asparaginases will provide benefit to current patient populations (e.g., those with pediatric ALL), and extended use in other patient populations (e.g., adult ALL, AML, and other cancers).

As is known in the art, L-asparaginases (L-asparagine aminohydrolase, E.C. 3.5.1.1) are amidases that hydrolyses the amide bond in Asn to Asp and ammonia (Kumar & Verma (2012) *Asian J. Biochem. Pharma Res.* 3:197-205). Wild-type guinea pig (*Cavia porcellus*) L-asparaginase, referred to herein as "gpASNase1" or "GpA," is a 565 amino acid residue protein available under Uniprot Accession No. H0W0T5_CAVPO and SEQ ID NO:1. GpA exhibits anti-tumor activity, has a low $K_m$ value for asparagine and lacks L-glutaminase activity. However, wild-type GpA only shares approximately 70% sequence identity with hASNase1. Accordingly, this invention provides a truncated GpA, which in some embodiments is humanized to decrease immunogenicity. In particular, this invention provides a truncated GpA variant sharing at least 85% sequence identity with residues 1 to 359 of SEQ ID NO:1.

A "GpA variant" refers to a non-naturally occurring form of GpA that exhibits L-asparaginase activity, has a low $K_m$ for Asn, and lacks L-glutaminase activity. By comparison, a "wild-type" GpA refers to the typical form of the L-asparaginase when isolated from a naturally occurring source. A wild-type is that which is most frequently observed in a natural population and is thus arbitrarily designated the normal or wild-type form. Wild-type GpA has a reaction rate ($k_{cat}$) of approximately 39 s$^{-1}$ and $K_m$ for Asn of 58 μM (Schalk, et al. (2014) *J. Biol. Chem.* 289:33175-33186). A truncated GpA variant of this invention typically exhibits a $k_{cat}$ of at least 75%, 80%, 85%, 90%, 95%, or 100% of wild-type GpA enzyme and exhibits a $K_m$ for Asn of less than 250 μM, 200 μM, 150 μM, 100 μM, 80 μM or 60 μM.

At a minimum, a GpA variant is truncated. "Truncated GpA" refers to a GpA wherein all or a portion of the approximately 206 C-terminal amino acid residues have been removed. In certain embodiments, a truncated GpA protein retains the N-terminal 359 amino acid residue catalytic domain. Ideally, the full-length GpA (SEQ ID NO:1) is C-terminally truncated at a position between residue 359 and 396. In particular, the full-length GpA (SEQ ID NO:1) is C-terminally truncated at position 359, 367, 369, 374, 384, 392 or 396. In certain embodiments, a truncated GpA variant is C-terminally truncated at position 369. Exemplary truncated GpA variants are provided in SEQ ID NO:3 (GpA359), SEQ ID NO:4 (GpA367), SEQ ID NO:5 (GpA369), SEQ ID NO:6 (GpA374), SEQ ID NO:7 (GpA384), SEQ ID NO:8 (GpA392) and SEQ ID NO:9 (GpA396). In some embodiments, a C-terminally truncated GpA variant comprises or consists of SEQ ID NO:3. In certain embodiments, a C-terminally truncated GpA variant comprises or consists of SEQ ID NO:5.

According to other aspects of this invention, a GpA variant is truncated and includes at least one amino acid substitution or modification (e.g., PEGylation or protein fusion) that increases stability, increases sequence identity with hASNase1, and/or increases in vivo circulation time of the GpA as compared to a wild-type GpA enzyme. As demonstrated herein, amino acid residues located on the surface of GpA were mutated to either humanize GpA and/or provide a site suitable for PEGylation. Further, fusion of GpA to protein tags or trimeric TRAIL provides stability and/or enhanced tumor cell killing activity.

Accordingly, in some aspects, a GpA variant has at least one amino acid substitution relative to wild-type GpA (SEQ ID NO:1). In particular embodiments, the amino acid residue that is substituted is a surface residue. The term "surface residue" refers to a residue located on a surface of a protein. In contrast, a buried residue is a residue that is not located on the surface of a protein. A surface residue usually includes a hydrophilic side chain. Operationally, a surface residue can be identified computationally from a structural model of a protein as a residue that contacts a sphere of hydration rolled over the surface of the molecular structure. A surface residue also can be identified experimentally through the use of deuterium exchange studies, or accessibility to various labeling reagents such as, e.g., hydrophilic alkylating agents. In particular embodiments, the amino acid substitution is not at one of the active site residues, e.g., Thr19, Ser85, Ser86, Thr116, Asp117, Ala142, Lys188, Asn272, and Tyr308.

Surface residues of GpA that can be substituted to generate the GpA variant of this invention include, but are not limited to, amino acid residues at position 7, 10, 23, 25, 40, 48, 49, 52, 53, 54, 57, 58, 59, 60, 62, 92, 98, 101, 106, 108, 121, 122, 131, 132, 134, 147, 193, 198, 217, 221, 222, 223, 224, 225, 226, 233, 236, 250, 253, 257, 261, 281, 282, 283, 284, 301, 311, 340, 344, 345, 347, 352, 358, 359, 360, 362, 363, 364, 365, 366, 367, or 368 of SEQ ID NO:1. In some embodiments, a GpA variant includes at least one amino acid substitution. In other embodiments, a GpA variant includes about 1 to 50, 1 to 45, 1 to 40, 1 to 35, 1 to 30, 1 to 25, 1 to 20, 1 to 15, 1 to 10, 1 to 7, or 1 to 4 amino acid substitutions. In particular embodiments, a GpA variant includes an amino acid substitution at one or more of positions 7, 10, 23, 25, 48, 49, 52, 53, 54, 57, 58, 59, 60, 62, 92, 98, 101, 106, 108, 121, 122, 134, 147, 193, 198, 217, 233, 236, 250, 257, 281, 301, 311, 340, 344, 360, 362, 363, 364, 365, 366, 367 and 368 of SEQ ID NO:1.

As indicated herein, truncated GpA369 shares about 72% sequence identity with the N-terminal 371 amino acid residues of hASNase1. Ideally, the at least one amino acid substitution of GpA generates a GpA variant with increased amino acid sequence identity with hASNase1 compared to wild-type GpA. Accordingly, one aspect of this invention provides for the humanization of GpA. In accordance with this aspect of the invention, the truncated GpA variant preferably has an amino acid sequence identity with the N-terminal 371 amino acid residues of hASNase1 of at least 70%, 72%, 74%, 76%, 78%, 80%, 82% or 84%. Further, the truncated GpA variant shares at least 85%, 87%, 89%, 91%, 93%, 95%, 97% or 99% sequence identity with wild-type truncated GpA.

Preferably, humanization of truncated GpA is achieved by replacing one or more surface residues of wild-type GpA with the corresponding surface residues of hASNase1. In particular, humanization of truncated GpA is achieved by replacing wild-type GpA residue H10, Q23, K25, K48, Q52, Q54, D91, D92, K98, E101, Q108, S121, G122, H134, R147, K193, D217, N233, H236, S250, Q288, R301, E344, L360, T362, A363, L365, H366, Q367, or S368, or any combination thereof, with the corresponding surface residue of hASNase1. Specifically, humanization of truncated GpA is achieved by making one or more of the following amino acid substitutions: H10R, Q23R, K25E, K48E, Q52R, Q54R, D91A, D92E, K98Q, E101K, Q108H, S121F, G122A, H134Q, R147H, K193R, D217E, N233S, H236Q, S250A, Q288E, R301Q, E344D, L360P, T362S, A363V, L365E, H366R, Q367R and/or S368P to wild-type GpA. Exemplary truncated and humanized GpA variants are provided in SEQ ID NO:45, SEQ ID NO:46, SEQ ID NO:47, SEQ ID NO:48, SEQ ID NO:49, SEQ ID NO:50, SEQ ID NO:58, SEQ ID NO:59, SEQ ID NO:60, SEQ ID NO:61, SEQ ID NO:62, SEQ ID NO:64, SEQ ID NO:65 and SEQ ID NO:86.

PEGylation of L-asparaginases has been shown to increase in vivo circulation time. The term "PEGylated" or "PEGylation" refers to conjugation of an L-asparaginase with polyethylene glycol (PEG). "PEG" or "polyethylene glycol" refers to any water-soluble poly(ethylene glycol) or poly(ethylene oxide). The expression PEG thus comprises the structure $(CH_2CH_2O)_n$, wherein n is an integer from 2 to about 1000. A commonly used PEG is end-capped PEG, wherein one end of the PEG termini is end-capped with a relatively inactive group such as alkoxy, while the other end is a hydroxyl group that may be further modified by linker moieties. In one embodiment, the capping group is methoxy and the corresponding end-capped PEG is denoted mPEG. Hence, mPEG is $CH_3O(CH_2CH_2O)_n$, wherein n is an integer from 2 to about 1000. In another embodiment, the capping group is hydroxyl and the corresponding end-capped PEG is hydroxyPEG. "PEG" followed by a number (not being a subscript) indicates a PEG moiety with the approximate molecular weight equal the number multiplied by 1,000. Hence, "PEG40" or "PEG40K" is a PEG moiety having an approximate molecular weight of 40 kDa. Examples of methods that may be used for determining PEG molecular weight include, without limitation, mass spectrometry, such as, for example, TOF-MS. PEG may be provided, for example, by NOF Corporation, Tokyo, Japan; Creative PEG-works, Winston Salem, N.C.; and Nanocs, Boston, Mass.

In one embodiment, the PEG moiety may be attached by nucleophilic substitution (acylation) on N-terminal alpha-amino groups or on lysine residue(s) on the gamma-positions, e.g., with OSu-activated esters. In another embodiment, the PEG moiety may be attached by reductive alkylation on amino groups present in the GpA protein using PEG-aldehyde reagents and a reducing agent, such as sodium cyanoborohydride. In another embodiment, the PEG moiety may be attached to the side-chain of an unpaired cysteine residue in a Michael addition reaction using for example PEG maleimide reagents. Other PEGylation methods include, but are not limited to, bridging PEGylation, transglutaminase PEGylation, glycoPEGylation, PEGylation using genetic engineering, releasable linkers PEGylation. For a review on PEGylation methods, see Pasut & Veronese (2012) *J. Contr. Rel.* 161:461-472; and Roberts, et al. (2012) *Adv. Drug Del. Rev.* 64:116-127. In one embodiment, the PEG moieties are attached to side chain(s) of lysine or cysteine residue(s).

"Linker" refers to a chemical moiety which connects an —HN— group of the GpA protein with the —O— group of a PEG moiety. In a preferred embodiment, the linker does not have any adverse influence on the activity of GpA. The linker is typically a derivative of a carboxylic acid, wherein the carboxylic acid functionality is used for attachment to the GpA protein via an amide bond. Examples of linkers include, but are not limited to, an acetic acid moiety with the linking motif: $CH_2CO$, a propionic acid moiety with the linking motif: $CH_2CH_2CO$ or $CHCH_3CO$, a butyric acid moiety with the linking motif: $CH_2CH_2CH_2CO$ or $CH_2CHCH_3CO$, a CO group, N-(aminocarbonyl)succinimide derivatives (such as, for example, N—(N-propylpropanamide) succinimide, N—(N-propylhexanamide) succinimide and N—(N-ethylpropanamide)succinimide), pentanoic acid $((CH_2)_5CO)$, α-methyl butanoic acid $(CH_2CH_2CH(CH_3)CO)$, succinic acid $(CO(CH_2)_2CO)$, glutaric acid $(CO(CH_2)_3CO)$, succinamide derivatives (such as, for example, $(CH_2)_2NHCO(CH_2)_2CO$), glutaramide derivatives (such as, for example, $(CH_2)_3NHCO(CH_2)_3CO$ and $(CH_2)_2NHCO(CH_2)_3CO$). Exemplary PEG molecules of use in this invention include, but are not limited to, methoxy PEG succinimidyl carbonate (mPEG-SC), mPEG-succinimidyl carboxy methyl ester (mPEG-SCM) and mPEG-succinamide succinimidyl ester (mPEG-SAS).

Methods of PEGylation that can be used to PEGylate an L-asparaginase of the invention are provided, for example, in U.S. Pat. Nos. 4,179,337, 5,766,897, US 2002/0065397, and US 2009/0054590. Ideally, a PEGylated GpA variant is produced by reacting PEG with a truncated GpA variant in a ratio of PEG:GpA of about 20:1 to 100:1, or more particularly 20:1 to 50:1, or most particularly 20:1, depending on the PEG size. In some aspects, the GpA variant has at least one cysteine residue, the PEG is a maleimide PEG, the reaction is carried out in the absence of glycine or aspartic acid, and the reaction product is treated with beta-mercaptoethanol. In other aspects, the GpA variant has at least one lysine residue, the PEG is mPEG-SC, mPEG-SCM or mPEG-SAS, and the reaction is carried out in the absence of DTT and glycerol.

As disclosed herein, an L-asparaginase can be PEGylated by site-specific PEGylation at 1 to 6 cysteine or 10 to 30 lysine residues introduced into the amino acid sequence of the L-asparaginase by amino acid substitution. See Examples 4 and 5. In particular, truncated GpA, or a humanized and truncated GpA may be PEGylated by introduction of: (a) a cysteine residue at position 49, 52, 225, 257, 281 and/or 340; or (b) a lysine residue at position 7, 53, 54, 57, 58, 98, 106, 233, 250, 257, 281, 311 and/or 340. In addition to introduction of cysteine or lysine residues at specific locations, endogenous cysteine or lysine residues may be mutated (i.e., substituted with another residue) to more evenly distribute the PEGylation sites over the length of the protein. In this respect, certain embodiments include replacing residue Cys198 with Ala, Val or Ser and/or replacing residue Lys223 with Asp. In one embodiment, Cys198 is replaced with Ala and the L-asparaginase derivative is PEGylated at Cys79. In other embodiments, Cys198 is replaced with Ala and one or more of the amino acid residues at positions 49, 225 and 340 are replaced with cysteine. Exemplary truncated GpA variants suitable for PEGylation are provided in SEQ ID NO:51 (GpA369-C198A), SEQ ID NO:52 (GpA369-C198S), SEQ ID NO:53 (GpA369-C198V), SEQ ID NO:54 (GpA369-C198A+K225C), SEQ ID NO:55 (GpA369-C198A+K225C+E340C), SEQ ID NO:56 (GpA369-C198A+K225C+E340C+E49C), SEQ ID NO:57 (GpA369-C198A+K225C+E340C+E49C+Q257C), SEQ ID NO:58 (GpA369(hum)-Group1+2+3-C198A), SEQ ID NO:59, SEQ ID NO:60, SEQ ID NO:61, SEQ ID NO:62, SEQ ID NO:63, SEQ ID NO:64, SEQ ID NO:65 and SEQ ID NO:86.

To increase the in vivo circulation time of truncated GpA, this invention also provides the variants, in particular truncated GpA variants, having a histidine tag (His), a SUMO tag (SUMO), an albumin-binding domain (ABD), or a combination thereof. The truncated GpA variant can include the histidine tag, SUMO tag and/or an albumin-binding domain at its C-terminus, N-terminus, and/or an internal location within the GpA sequence. Ideally, when a His tag, SUMO tag or ABD is inserted within the GpA sequence (i.e., not at the N- or C-terminus), the insertion is in one or more flexible loops of the GpA protein. By way of illustration, the truncated GpA variant can have the N- to C-terminal structure of SUMO-Asparaginase-ABD, His-SUMO-ABD-Asparaginase, His-SUMO-Asparaginase-ABD, His-SUMO-Asparaginase, His-ABD-Asparaginase, ABD-Asparaginase, ABD-SUMO-Asparaginase, Asparaginase$^{1-225}$-ABD-Asparaginase$^{226-369}$, Asparaginase$^{1-340}$-ABD-Asparaginase$^{341-369}$, and the like. Nucleic acids encoding the His, SUMO or ABD can be inserted in-frame either 5' or 3' of the nucleic acids encoding the truncated GpA variant thereby creating a fusion protein.

Ideally, the inclusion of one or more of a histidine tag, a SUMO tag, an albumin-binding domain, or a combination thereof can significantly increase the in vivo circulation time of an L-asparaginase. Alternatively stated, the variant has a longer t½ than wild-type L-asparaginase administered at an equivalent protein dose. As used herein, the term "t½" or "half-life" refers to the time that would be required for the concentration of a truncated GpA variant or fusion protein thereof to fall by half in vitro or in vivo, for example, after injection in a mammal. Given that efficacy of L-asparaginases is related to the in vivo half-life of the drug, the truncated GpA variants of this invention are particularly useful in the treatment of cancers, such as leukemias and lymphomas.

As used herein, a "histidine tag" refers to an amino acid motif composed of at least one histidine (His) residue and preferably at least 6 His residues. The histidine tag includes a polyhistidine of 6 (hexa histidine tag, 6×His tag, or His$_6$ tag), 7, 8, 9, 10, or up to 20 histidine residues.

A "SUMO tag" refers to the fusion of a SUMO (small ubiquitin-related modifier) protein to a protein of interest to enhance the solubility/stability of the protein of interest. The inclusion of a SUMO tag can be achieved using known expression systems such as the CHAMPION pET SUMO expression system (Invitrogen), the EXPRESSO T7 SUMO cloning and expression system (Lucigen), or pET His6 SUMO TEV LIC cloning vector (Addgene). In addition to SUMO tag, it is contemplated that other Ubl proteins can be used including, but not limited to, Ub, Rub1, Hub1, ISG15, Ubi-L (MNSF), FAT10, Apg12, Apg8 and Urml (Larsen & Wang (2002) *J. Proteome Res.* 1(5):411-9). See also U.S. Pat. No. 7,655,413, incorporated herein by reference in its entirety. Exemplary SUMO tags are set forth in SEQ ID NO:66, SEQ ID NO:67, SEQ ID NO:68, SEQ ID NO:69 and SEQ ID NO:70.

An "albumin-binding domain" or "ABD" refers to a polypeptide that binds albumin in vivo or in vitro and enhances the serum half-life and biodistribution of a therapeutic agent. Albumin may be derived from any animal species, for example human, monkey, or rodent. Albumin-binding domains are described, for example, in U.S. Pat. No. 6,267,964, WO 1991/19741, WO 2005/097202, WO 2001/45746, WO 2013/043071 and US 2004/0001827. Further, U.S. Pat. No. 9,156,887 discloses non-natural albumin-binding domains, which may be used in this invention. In some embodiments, the albumin-binding domain has the amino acid sequence set forth in SEQ ID NO:71, SEQ ID NO:72 or SEQ ID NO:73.

Enhanced cytotoxic activity of the truncated GpA variants disclosed herein can be achieved by conjugating or fusing the GpA to three tandem soluble domains of TRAIL or co-administering the GpA with a stable form of TRAIL. The resulting fusion protein can provide at least a 20-, 25-, 30-, 35-, or 40-fold decrease in IC$_{50}$ value compared to a truncated GpA variant lacking the three tandem soluble domains of TRAIL. Accordingly, a truncated GpA variant fused to three tandem soluble domains of TRAIL is particularly useful in the treatment of cancer, in particular, L-asparaginase-insensitive cancers.

A "fusion protein" refers to a chimeric protein containing proteins or protein fragments (e.g., GpA variants) operably linked in a non-native way. In accordance with the fusion protein of this invention, three tandem soluble domains of TRAIL (TRAIL$_{trimer}$) are fused, in-frame, with a truncated GpA variant. Ideally, a glycine or serine residue is inserted between each TRAIL repeat to facilitate folding of the TRAIL trimer (see, e.g., SEQ ID NO:87 and SEQ ID NO:88). Optionally, the TRAIL trimer and Asparaginase components can be separated by a linker as set forth in SEQ ID NO:81, SEQ ID NO:82, SEQ ID NO:83, or SEQ ID NO:84. The fusion protein can include the TRAIL trimer fused to the C-terminus (GpA-TRAIL$_{trimer}$; e.g., SEQ ID NO:89 and SEQ ID NO:90) or N-terminus (TRAIL$_{trimer}$-GpA; e.g., SEQ ID NO:91 and SEQ ID NO:92) of GpA, where the GpA component can be any the previously described variants. When further used in combination with a tag or modification, the fusion protein can have the structure of: SUMO-TRAIL$_{trimer}$-GpA-ABD, His-SUMO- ABD-TRAIL$_{trimer}$-GpA, His-SUMO-TRAIL$_{trimer}$-GpA-ABD, His-SUMO-GpA-TRAIL$_{trimer}$, His-ABD-TRAIL$_{trimer}$-GpA, ABD-GpA-TRAIL$_{trimer}$, ABD-SUMO-TRAIL$_{trimer}$-GpA, and the like. In addition to being inserted at the N- or C-terminus, the ABD peptide can be engrafted in one or more flexible loops of GpA variants. In one example, the flexible loop spans residues 215 to 228. In another example, the flexible loop spans residues 337 to 342 of GpA. See, e.g., SEQ ID NO:94 and SEQ ID NO:95. Nucleic acids encoding TRAIL in particular TRAIL$_{trimer}$ can be inserted in-frame either 5' or 3' of the nucleic acids encoding the L-asparaginase thereby creating the fusion protein.

Preferably, the soluble domains of TRAIL are derived from a mammalian, particularly human TRAIL including allelic variants and/or derivatives thereof. The soluble domains include the extracellular portion of TRAIL including the receptor binding domain without membrane localized domains. Like other proteins of the TNF superfamily, TRAIL is anchored to the membrane via an N-terminal portion of 15-30 amino acids, the so-called stalk-region. The stalk region contributes to trimerization and provides a certain distance to the cell membrane. However, the stalk region is not part of the receptor binding domain (RBD). Accordingly, it is preferred that the soluble TRAIL domains include the receptor binding domain of the TRAIL lacking any amino acids from the stalk region (see US 2015/0337027).

The soluble TRAIL domain may be derived from human TRAIL. Preferably, the soluble TRAIL domains are derived from human TRAIL, particularly starting from amino acid residues 115-122, and include amino acid residues 115-281, 120-281, 121-281 or 122-281 of human TRAIL. In certain embodiments, each of the soluble domains of TRAIL$_{trimer}$ are composed of residues 115-281 of human TRAIL. Residues 115-281 of human TRAIL are set forth herein in SEQ ID NO:80. To facilitate correct folding, a glycine or serine residue may be inserted between each TRAIL repeat. See, e.g., SEQ ID NO:87 and SEQ ID NO:88.

Derivatives and variants of the death receptor binding TRAIL domains are all contemplated and can be made by altering their amino acid sequences by substitutions, additions, and/or deletions/truncations or by introducing chemical modifications that result in functionally equivalent polypeptides. It will be understood by one of ordinary skill in the art that certain amino acids in a sequence of any polypeptide may be substituted for other amino acids without adversely affecting the activity of the polypeptides.

The TRAIL domains disclosed herein include substitutions of one or more of the amino acids in the disclosed sequences. A skilled artisan will be able to determine using well-known techniques suitable sequence variants of the peptides set forth herein. In certain embodiments, one skilled in the art may identify suitable areas of the molecule that may be changed without destroying activity by targeting regions not believed to be important for activity. In other embodiments, the skilled artisan can identify residues and portions of the molecules that are conserved among similar polypeptides. In further embodiments, even amino acid residues important for biological activity or for structure may be subject to conservative amino acid substitutions without destroying the biological activity thereof or without adversely affecting the peptide structure.

The three soluble domains of TRAIL are preferably linked to one another via peptide linking group composed of one to eight amino acid residues. Likewise, it is preferable that TRAIL$_{trimer}$ is linked to the L-asparaginase via a peptide linking group composed of one to twenty amino acid residues. The term "peptide linking group" or "linker" is meant to refer to a peptide moiety that acts as a molecular bridge to operably link two different molecules together. Desirably, the linkers of this invention are composed of glycine or serine, or a combination thereof. In particular embodiments, each of the soluble domains of TRAIL$_{trimer}$ are preferably linked to one another by a single glycine or single serine residue. An exemplary TRAIL$_{trimer}$ includes a single serine residue between the three soluble TRAIL domains (SEQ ID NO:88). Regarding the peptide linking group located between the TRAIL$_{trimer}$ and L-asparaginase, it is desirable that this linker is a flexible linker. The flexible linker preferably has a length of one to 20 amino acid residues, particularly a length of 6, 9, 12, 15 or 18 amino residues. The flexible linker is preferably a glycine/serine linker, i.e., a peptide linker composed primarily of the amino acids glycine and serine. In a particular embodiment, the linker between the TRAIL$_{trimer}$ and L-asparaginase is a (GGGS)$_n$ linker (SEQ ID NO:81), wherein n is 1 to 4, or a permutation thereof including, e.g., GGGS(GGGGS)$_n$ (SEQ ID NO:82), herein n is 1 to 4. In certain embodiments, the linker between the TRAIL$_{trimer}$ and L-asparaginase has the amino acid sequence set forth in SEQ ID NO:83. In other embodiments, the linker between the TRAIL$_{trimer}$ and L-asparaginase has the amino acid sequence set forth in SEQ ID NO:84. An example of a TRAIL$_{trimer}$-GpA variant fusion protein has an N-terminal TRAIL$_{trimer}$ including a single glycine or serine residue between the three soluble TRAIL domains and a glycine/serine linker between the TRAIL$_{trimer}$ and truncated GpA variant. See, e.g., SEQ ID NO:89, SEQ ID NO:90, SEQ ID NO:91 and SEQ ID NO:92.

A stable form of TRAIL is intended to refer to a form of TRAIL that promotes trimerization. In particular, to promote trimerization of TRAIL, the FOLDON sequence (GYIPEAPRDGQAYVRKDGEWVLLSTFL; SEQ ID NO:85), a small trimerization domain, has been shown to maintain TRAIL stability and biological activity at 37° C. for at least 48 hours (Kouno, et al. (2013) *J. Invest. Dermatol.* 133(9):2212-2220). Accordingly, the FOLDON peptide was inserted between a His-SUMO tag and the N-terminus of TRAIL to result in a His-SUMO-FOLDON-TRAIL fusion protein. The fusion protein was expressed and a yield of >10 mg/L of the fusion protein was obtained in the bacterial culture. The protein was very stable, showing that the inclusion of FOLDON results in a stable form of TRAIL. Accordingly, a stable form of TRAIL can be co-administered and/or combined in a pharmaceutical composition with a truncated GpA variant to enhance cytotoxic activity of the GpA.

The truncated GpA variants and fusion proteins disclosed herein can be readily prepared by conventional recombinant protein techniques, wherein recombinant host cells are transformed or transduced with an expression construct or vector harboring a nucleic acid molecule encoding the variant or fusion protein, the recombinant host cells are grown under suitable conditions to provide for expression of the variant or fusion protein, and the variant or fusion protein is subsequently isolated and optionally purified. Accordingly, this invention also provides a nucleic acid molecule encoding a truncated GpA variant or a fusion protein thereof, as well as an expression cassette and/or expression vector containing the same. Ideally, the expression cassette and expression vector contain the necessary regulatory sequences (e.g., promoter, terminator, and the like) to facilitate expression in the host cell of interest. Host cells including a nucleic acid molecule encoding a truncated GpA variant or fusion protein are also included within the scope of this invention. Host cells can include eukaryotic cells (e.g., mammalian, fungal or yeast cells) or prokaryotic cells (e.g., *E. coli*).

Once produced and isolated/purified, the truncated GpA variant and/or fusion protein of the invention can be used as is or formulated in a pharmaceutical composition containing a pharmaceutically acceptable excipient. Pharmaceutical compositions provided herein can be specially formulated for intravenous administration in solid or liquid form or for intravenous injection. Optimal pharmaceutical compositions can be determined by one skilled in the art depending upon, for example, the intended route of administration, delivery format and desired dosage. See, for example, Remington's Pharmaceutical Sciences (19th edition, 1995).

The truncated GpA variant and/or fusion protein can be incorporated in a conventional systemic dosage form, such as an injectable formulation. The dosage forms may also include the necessary physiologically acceptable carrier material, excipient, lubricant, buffer, surfactant, antibacterial, bulking agent (such as mannitol), antioxidants (ascorbic acid or sodium bisulfite) or the like.

The primary carrier or excipient in a pharmaceutical composition may be either aqueous or non-aqueous in nature. For example, a suitable carrier or excipient may be water for injection, physiological saline solution or artificial cerebrospinal fluid, possibly supplemented with other materials common in compositions for parenteral administration. Neutral-buffered saline or saline mixed with serum albumin are further exemplary vehicles. Pharmaceutical compositions can include Tris buffer of about pH 7.0-8.5, or acetate buffer of about pH 4.0-5.5, which may further include sorbitol or a suitable substitute therefor. Pharmaceutical compositions of the invention may be prepared for storage by mixing the selected composition having the desired degree of purity with optional formulation agents (Remington's Pharmaceutical Sciences, Id.) in the form of a lyophilized cake or an aqueous solution. Further, the truncated GpA variant or fusion protein of the invention may be formulated as a lyophilizate using appropriate excipients such as sucrose or glycine.

Administration routes for the truncated GpA variant, fusion protein, or pharmaceutical compositions of the invention include injection by intravenous, intraperitoneal, intracerebral (intra-parenchymal), intracerebroventricular, intramuscular, intra-ocular, intraarterial, intraportal, or intralesional routes; by sustained release systems or by implantation devices. Compositions may be administered by bolus injection or continuously by infusion, or by implantation device. Compositions also can be administered locally via implantation of a membrane, sponge or another appropriate material onto which the desired molecule has been absorbed or encapsulated. Where an implantation device is used, the device may be implanted into any suitable tissue or organ, and delivery of the desired molecule may be via diffusion, timed-release bolus, or continuous administration.

The compositions of the invention can be delivered parenterally. When parenteral administration is contemplated, the therapeutic compositions for use in this invention may be in the form of a pyrogen-free, parenterally acceptable aqueous solution comprising the desired compound identified in a screening method of the invention in a pharmaceutically acceptable vehicle. A particularly suitable vehicle for parenteral injection is sterile distilled water in which the compound identified in a screening method of the invention is formulated as a sterile, isotonic solution, appropriately preserved. Preparation can involve the formulation of the desired molecule with an agent, such as injectable microspheres, bio-erodible particles, polymeric compounds (such as polylactic acid or polyglycolic acid), beads or liposomes, that may provide controlled or sustained release of the product which may then be delivered via a depot injection. Formulation with hyaluronic acid has the effect of promoting sustained duration in the circulation. Implantable drug delivery devices may be used to introduce the desired molecule.

The compositions may also be formulated for inhalation. In these embodiments, the truncated GpA variant or fusion protein is formulated as a dry powder for inhalation, or inhalation solutions may also be formulated with a propellant for aerosol delivery, such as by nebulization. Pulmonary administration is further described in WO 1994/020069, which describes pulmonary delivery of chemically modified proteins.

The compositions of the invention can be delivered through the digestive tract, such as orally. The preparation of such pharmaceutically acceptable compositions is within the skill of the art. The truncated GpA variant or fusion protein of the invention that is administered in this fashion may be formulated with or without those carriers customarily used in the compounding of solid dosage forms such as tablets and capsules. A capsule may be designed to release the active portion of the formulation at the point in the gastrointestinal tract when bioavailability is maximized and pre-systemic degradation is minimized. Additional agents can be included to facilitate absorption of the peptides of the invention disclosed herein. Diluents, flavorings, low melting point waxes, vegetable oils, lubricants, suspending agents, tablet disintegrating agents, and binders may also be employed.

These compositions may also contain adjuvants such as preservative, wetting agents, emulsifying agents and dispersing agents. Prevention of the action of microorganisms can be ensured by the inclusion of various antibacterial and antifungal agents, for example, paraben, chlorobutanol, phenol sorbic acid and the like. It may also be desirable to include isotonic agents such as sugars, sodium chloride and the like. Prolonged absorption of the injectable pharmaceutical form can be brought about by the inclusion of agents which delay absorption such as aluminum monostearate and gelatin.

The truncated GpA variant and/or fusion protein of the invention find particular use in the treatment of a disease or condition treatable by depletion of asparagine. Accordingly, this invention also provides methods for treating a disease, in particular cancer, by administering to a subject in need of treatment and effective amount of a truncated GpA variant or fusion protein. An "effective amount" is used herein to refer to an amount of an active ingredient sufficient to achieve the intended purpose of (a) reducing the severity of the disorder; (b) limiting or preventing development of symptoms characteristic of the disorder(s) being treated; (c) inhibiting worsening of symptoms characteristic of the disorder(s) being treated; (d) limiting or preventing recurrence of the disorder(s) in patients that have previously had the disorder(s); (e) limiting or preventing recurrence of symptoms in patients that were previously symptomatic for the disorder(s); (f) reduction of mortality after occurrence of a disease or a disorder; (g) healing; and (h) prophylaxis of a disease. The effective amount in each individual case may be determined empirically by a skilled artisan according to established methods in the art. As used in the context of the invention, "administering" includes in vivo administration to an individual as well as administration directly to cells or tissue in vitro or ex vivo. An effective amount of a truncated GpA variant or fusion protein is generally that which can induce apoptosis and reduce circulating L-asparagine in cancer cells or a tumor of the subject. A clinician may titer the dosage or route of administration to obtain the optimal therapeutic effect.

In certain embodiments, the truncated GpA variant or fusion protein is useful in the treatment or the manufacture of a medicament for use in the treatment of cancers such as acute lymphoblastic Leukemia (ALL) in both adults and children, as well as other conditions where asparagine depletion is expected to have a useful effect. Such conditions include, but are not limited to, malignancies or cancers, including but not limited to hematalogic malignancies, non-Hodgkin's lymphoma, NK lymphoma, pancreatic cancer, ovarian cancer, Hodgkin's disease, acute myelocytic Leukemia, acute myelomonocytic Leukemia, chronic lymphocytic Leukemia, lymphosarcoma, reticulosarcoma, and melanosarcoma. Representative non-malignant hematologic diseases which respond to asparagine depletion include immune system-mediated blood diseases, e.g., infectious diseases such as those caused by HIV infection (i.e., AIDS). Non-hematologic diseases associated with asparagine dependence include autoimmune diseases, for example rheumatoid arthritis, SLE, autoimmune, collagen vascular diseases, AIDS, etc. Other autoimmune diseases include osteo-arthritis, Issac's syndrome, psoriasis, insulin dependent diabetes mellitus, multiple sclerosis, sclerosing panencephalitis, systemic lupus erythematosus, rheumatic fever, inflammatory bowel disease (e.g., ulcerative colitis and Crohn's disease), primary billiary cirrhosis, chronic active hepatitis, glomerulonephritis, myasthenia gravis, pemphigus vulgaris, and Graves' disease. In particular embodiments, the truncated GpA variant or fusion protein is used in the treatment of non-Hodgkin's lymphoma, leukemia, acute lymphoblastic leukemia, acute myeloid leukemia, B cell lymphoma, Burkitt's lymphoma, chronic myelocytic leukemia, chronic lymphocytic leukemia, and hairy cell leukemia.

Cells suspected of causing disease can be tested for asparagine dependence in any suitable in vitro or in vivo assay, e.g., an in vitro assay wherein the growth medium lacks asparagine. Thus, in one aspect, the invention is directed to a method of treating a disease treatable in a patient, the method comprising administering to the patient an effective amount of truncated GpA variant or fusion protein of the invention. In a specific embodiment, the disease is ALL. In a particular embodiment, the truncated GpA variant or fusion protein used in the treatment of a disease treatable by asparagine depletion includes a truncated GpA variant from guinea pig.

The truncated GpA variant or fusion protein can be administered on a schedule ranging from about 3-times a week to about once a month, typically once per week or once every other week, as a single agent (e.g., monotherapy) or as part of a combination of chemotherapy drugs, including, but not limited to glucocorticoids, corticosteroids, anticancer compounds or other agents, including, but not limited to methotrexate, dexamethasone, prednisone, prednisolone, vincristine, cyclophosphamide, and anthracycline. As an example, patients with ALL will be administered the truncated GpA variant or fusion protein of the invention as a component of multi-agent chemotherapy during 3 chemotherapy phases including induction, consolidation or intensification, and maintenance. In a specific example, the truncated GpA variant or fusion protein is not administered with an asparagine synthetase inhibitor (e.g., see WO 2007/103290). In another specific example, the truncated GpA variant or fusion protein is not administered with an asparagine synthetase inhibitor but is administered with other chemotherapy drugs. The truncated GpA variant or fusion protein can be administered before, after, or simultaneously with other compounds as part of a multi-agent chemotherapy regimen.

In a specific embodiment, the method involves administering a truncated GpA variant or fusion protein of the invention at an amount of about 1 U/kg to about 1000 U/kg. In a more specific embodiment, the truncated GpA variant or fusion protein is administered at an amount selected from the group consisting of about 20, 50, 60, 70, 100, 200, 300, 400, 500 and 600 U/kg. In another specific embodiment, the truncated GpA variant or fusion protein is administered at a dose ranging from about 1000 IU/m$^2$ to about 20000 IU/m$^2$ (e.g., 1000 IU/m$^2$, 2000 IU/m$^2$, 3000 IU/m$^2$, 4000 IU/m$^2$, 5000 IU/m$^2$, 6000 IU/m$^2$, 7000 IU/m$^2$, 8000 IU/m$^2$, 9000 IU/m$^2$, 10000 IU/m$^2$, 11000 IU/m$^2$, 12000 IU/m$^2$, 13000 IU/m$^2$, 14000 IU/m$^2$, 15000 IU/m$^2$, 16000 IU/m$^2$, 17000 IU/m$^2$, 18000 IU/m$^2$, 19000 IU/m$^2$, or 20000 IU/m$^2$). In another specific embodiment, the truncated GpA variant or fusion protein is administered at a dose that depletes Asn to undetectable levels for a period of about 3 days to about 10 days (e.g., 3, 4, 5, 6, 7, 8, 9, or 10 days) for a single dose. In another embodiment, the method involves administering a truncated GpA variant or fusion protein of the invention that has a longer in vivo circulating half-life after a single dose compared to the wild-type L-asparaginase.

The following non-limiting examples are provided to further illustrate the present invention.

Example 1: Generation of Active, C-Terminally Truncated GpA

Mammalian L-asparaginases such as human L-asparaginase (hASNase1; UNIPROT entry Q86U10; SEQ ID NO:2) and the guinea pig L-asparaginase (gpASNase1 or GpA; UNIPROT entry H0W0T5; SEQ ID NO:1) contain two domains; an N-terminal domain of ~360 residues where the L-asparaginase activity resides, and a C-terminal domain of ~200 residues of unknown function. By comparison, the clinically relevant bacterial L-asparaginases from *E. coli* and *Erwinia chrysanthemi* are about 350 amino acid residues in length and do not contain such a C-terminal domain.

One of the challenges of injectable biologics therapeutics comes from the short half-lives resulting in poor bioavailability. Clearance mostly results from proteolysis, renal filtration or from neutralization by the immune system. Larger molecules of foreign sequence have more chance to be detected by the immune system and get quickly cleared from the system. Identifying shorter yet stable versions of GpA was expected to provide a better therapeutic, especially in the context where the C-terminal domain of the full-length protein was of unknown function.

To assess the function of the C-terminal residues of GpA, C-terminally truncated GpA variants were constructed and analyzed for stability and full L-asparaginase activity. Sequence alignment of hASNase1, GpA, *E. coli* L-asparaginase, and *Erwinia* L-asparaginase enzymes and crystal structure analysis (indicated that catalytic domain ends at residue 359. A construct composed of residues 1-359 of GpA (SEQ ID NO:3) was recombinantly expressed, but the purified C-truncated enzyme was unstable. Therefore, additional C-terminally truncated GpA constructs were prepared (Table 1) fused to a SUMO tag.

TABLE 1

| GpA | Residues* | SEQ ID NO: |
|---|---|---|
| Full-length GpA | 1-565 | 1 |
| GpA359 | 1-359 | 3 |
| GpA367 | 1-367 | 4 |
| GpA369 | 1-369 | 5 |
| GpA374 | 1-374 | 6 |
| GpA384 | 1-384 | 7 |
| GpA392 | 1-392 | 8 |
| GpA396 | 1-396 | 9 |

*Relative to SEQ ID NO: 1.

Recombinant overexpression of these C-terminally truncated GpA constructs indicated that all proteins were well overexpressed and purified to >95% of purity (measured by SDS-PAGE). While GpA367 precipitated quickly in a matter of minutes after the stability SUMO tag was cut off, the longer variants showed excellent stability and activity, which was comparable to the full-length protein. Notably, longer constructs carrying an extra Cys388 tended to form an unspecific disulfide bond, altering the tetrameric form necessary for L-asparaginase activity. While a C-terminally truncated GpA composed of at least residues 1-369 yields a stable GpA enzyme with L-asparaginase activity, as demonstrated herein the stability of a C-terminally truncated GpA composed of residues 1-359 or 1-367 can be stabilized by fusion with a heterologous peptide/protein (e.g., a SUMO tag or albumin) or chemical modification (e.g., PEGylation).

Example 2: Humanized GpA Variants Produced by Directed Evolution

Overview.

Directed evolution, or the process to mimic natural evolutionary processes in the laboratory, is widely used to improve enzyme properties. See, e.g., Dalby (2011) Curr. Opin. Struct. Biol. 21:473-480; Goldsmith & Tawfik (2012) Curr. Opin. Struct. Biol. 22:406-412; Labrou (2010) Curr. Protein Pept. Sci. 11:91-100; Wang & Zhao (2012) Bioresour. Technol. 115:117-125. Given the advances in library generation, screening techniques and foremost a better understanding of mechanisms of natural protein evolution, large improvements in the evolved catalytic activity (relative to the starting point, and in absolute $k_{cat}/K_m$ values) have been obtained (Fasan, et al. (2008) J. Mol. Biol. 383:1069-80; Bar-Even, et al. (2011) Biochemistry (Mosc.) 50:4402-10).

To overcome immunogenicity, a human-like L-asparaginase with kinetic properties similar to that of the type II E. coli L-asparaginase was generated via a directed evolution approach. Using DNA family shuffling, several clones with high sequence identity to hASNase1 but with the low $K_m$ properties of the gpASNase1 were identified.

Strains.

Chromosomal gene deletions were performed using the λ-red recombinase system (Datsenko & Wanner (2000) Proc. Natl. Acad. Sci. U.S.A. 97:6640-6645). The tyrosine aminotransferase gene tyrB, the aspartate aminotransferase gene aspC and the L-asparaginase genes ansA, ansB, iaaA were deleted from the chromosome of E. coli BW25113 F⁻, DE(araD-araB)567, lacZ4787(del)::rrnB-3, LAM-, rph-1, DE(rhaD-rhaB)568, hsdR514 resulting in E. coli BW5Δ. Briefly, a primer pair was used to amplify the gene replaced by the kanamycin resistance cassette from the appropriate keio strain according to known methods (Datsenko & Wanner (2000) Proc. Natl. Acad. Sci. U.S.A. 97:6640-6645). Subsequently, the linear PCR product was used to replace the entire open reading frame of the targeted gene on the BW25113 chromosome. Colonies containing the correct gene deletions were transformed with the FLP recombinase plasmid pCP20 to remove the kanamycin resistance marker, and the pCP20 was then cured from the resulting strain. The strain E. coli BW2Δ was obtained following the same process and after the deletion of the genes ansA and ansB.

Cloning of hASNase1 and gpASNase1 into BW2Δ and BW5Δ. The gene encoding the codon-optimized sequence of the hASNase1 was amplified using the primers NdeI-hA_F1 and hA-BamHI R573 and the codon-optimized sequence of gpASNase1 with the primers NdeI-gpA_F1 and gpA-BamHI_R565 (Table 2). After a BamHI/NdeI digestion, the PCR products were inserted into the pBAD vector. The resulting vectors were subsequently used to transform the strains BW5Δ and BW2Δ, resulting in the strains BW5Δ pBAD_hASNase1, BW5ΔpBAD-gpASNase1, BW2Δ pBAD_hASNase1 and BW2Δ pBAD_gpASNase1. BW5Δ and BW2Δ were also transformed with the empty pBAD vector to serve as controls.

TABLE 2

| Primer | Sequence (5'→3') | SEQ ID NO: |
|---|---|---|
| gpA-BamHI_R565 | AACGTCGGATCCTTAAATAGCCGGCGGGACTTC | 10 |
| gpA_F | ATGGCACGCGCTTCGGGCTCGGAA | 11 |
| gpA_R | CCAGATTACGCAGCAGAGC | 12 |
| hA-F | GCTCGTGCTGTGGGTCCGGAA | 13 |
| hA_R | GACACCCGGCAGCACTTC | 14 |
| gpA360-367_R | CTGATGCAGGTCTGCCGTCGGCAGCGTCATTTCACCGCGCAGGT | 15 |
| hA354-361_F | AAGGACCTGCGCGGTGAAATGACGCTGCCGACGGCAGACCTGC | 16 |
| hA362-369_R | GCGACGTTCTTCCACAGACGGCGGGGTCATTTCACCACGCAGATC | 17 |
| gpA352-359_F | AAAGATCTGCGTGGTGAAATGACCCCGCCGTCTGTGGAAGAACG | 18 |

TABLE 2-continued

| Primer | Sequence (5'→3') | SEQ ID NO: |
|---|---|---|
| Lib1 M22R23_F | TACACCGGCGGCACCATTGGCNNKNNKAGTGAGC TCGGCGTGCTTGTG | 19 |
| Lib1 M22R23_R | CACAAGCACGCCGAGCTCACTMNNMNNGCCAATG GTGCCGCCGGTGTA | 20 |
| Lib2 D84S86_F | CTGGAGTGCCAGCCCCTCTTCNNKTCCNNKGACA TGACCATCGCTGAGTGG | 21 |
| Lib2 D84S86_R | CCACTCAGCGATGGTCATGTCMNNGGAMNNGAAG AGGGGCTGGCACTCCAG | 22 |
| Lib3 H114G115_F | CAGTACCACGGCTTTGTGGTCATCNNKNNKACCG ACACCATGGCCTTTGCTGCC | 23 |
| Lib3 H114G115_R | GGCAGCAAAGGCCATGGTGTCGGTMNNMNNGATG ACCACAAAGCCGTGGTACTG | 24 |
| Lib4 A142Q143V144_F | AGAAGACTGTCATCCTCACTGGGNNKNNKNNKCC CATCCATGCCCTGTGGAGC | 25 |
| Lib4 A142Q143V144_R | GCTCCACAGGGCATGATGGGMNNMNNMNNCCCAG TGAGGATGACAGTCTTCT | 26 |
| Lib5 A191R192_F | GCAACCGGGCAACCAAGGTAGACNNKNNKAGGTT CGCAGCTTTCTGCTCCCC | 27 |
| Lib5 A191R192_R | GGGGAGCAGAAAGCTGCGAACCTMNNMNNGTCTA CCTTGGTTGCCCGGTTGC | 28 |
| Lib6 T118F121_F | TCATCCACGGCACCGACNNKATGGCCNNKGCTGC CTCGATGCTGTCC | 29 |
| Lib6 T118F121_R | GGACAGCATCGAGGCAGCMNNGGCCATMNNGTCG GTGCCGTGGATGA | 30 |
| Lib7 A91C95T99_F | TCCAGTGACATGACCATCNNKGAGTGGGTTNNKC TTGCCCAGNNKATCAAGAGGCACTACGAG | 31 |
| Lib7 A91C95T99_R | CTCGTAGTGCCTCTTGATMNNCTGGGCAAGMNNA ACCCACTCMNNGATGGTCATGTCACTGGA | 32 |
| Lib8 R23E25L26_F | GGCGGCACCATTGGCATGNNKAGTNNKNNKGGCG TGCTTGTGCCCGGG | 33 |
| Lib8 R23E25L26_R | CCCGGGCACAAGCACGCCMNNMNNACTMNNCATG CCAATGGTGCCGCC | 34 |

Media and Growth Experiments. M9 complete medium was made from M9 minimum salt (Sigma) supplemented with 0.4% glycerol, 2 μM thiamine, 1 mM MgSO$_4$ 0.1 mM CaCl$_2$ and 100 μg/mL ampicillin. For complete M9 plates, 15 g/L of agar was added. For the experiments with the strain BW2Δ, M9 medium was made without NH$_4$Cl. When required, L-asparaginase was added to M9 medium at different concentrations. To induce the expression of hASNase1 and gpASNase1 cloned into the pBAD vector, 0.02% arabinose was added to the M9 medium. For the growth experiments on complete M9 on agar plates, the strains were first grown in LB overnight at 37° C., spun down and washed in M9 medium. An appropriate dilution of this suspension was then spread on the M9 plates so as to get the same number of colonies for each strain. Plates were incubated at 37° C. for 48 to 96 hours.

DNA Shuffling.

DNA shuffling was performed as described (Meyer, et al. (2014) *Curr. Protoc. Mol. Biol.*, Ausubel (ed) 105:Unit-15.12) with slight adjustments. Briefly, an equimolar mixture of the hASNase1 and GpA genes were digested with 0.5 U of DNase (NEB) for 2 minutes and 30 seconds. Fragments between 100 bp and 200 bp were extracted using the QIAQUICK gel extraction kit (Qiagen), reassembled by PCR and then amplified using either the primers specific to the GpA gene or the one specific to the hASNase1 gene. The obtained shuffled fragments were cloned into a pBAD vector using the Megawhop method (Miyazaki (2003) *Methods Mol. Biol.* 231:23-28). Briefly, 100 to 300 ng of shuffled fragments were used as megaprimers to run a whole plasmid PCR using either pBAD_hASNase1 or pBAD_gpASNase1 as template. After digestion of the template with DpnI, 20 to 40 ng of newly synthesized plasmids containing the shuffled sequences were used to transform electrocompetent BW5Δ cells. After the pulse, the cells were resuspended in 1 ml SOC medium and incubated with shaking at 37° C. for one hour. The cells were then spun down at 4000×g for 4 minutes and gently resuspended in 200 μL of M9 medium. One hundred μL were plated on M9 plate supplemented with 0.2 mM Asn or 2 mM Asn. After 4 days of incubation of the plates at 37° C., the colonies from the 2 mM Asn plate were isolated and pooled into 200 μL of fresh M9 medium. Two dilutions were successively carried out and used to plate fresh 0.2 mM Asn M9 plates. Clones capable of growing on the 0.2 mM Asn plate after 4 days of incubation at 37° C. and three additional days at room temperature were isolated and streaked on LB plates.

C-Terminal Domain Swapping.

To build the clone $h_N$-$g_C$, the sequence corresponding to the N-terminal domain of hASNase1 ($h_N$, residue 1-361) was amplified using the primers NdeI-hA_F1 and gpA360-367_R and the sequence corresponding to the C-terminal domain of gpASNase1 (gC, residue 360-565) was amplified using the primers hA354-361_F and gpA-BamHI_R565. To build the clone $g_N$-$h_C$ the sequence corresponding to the N-terminal domain of gpASNase1 ($g_N$, residue 1-359) was amplified using the primers NdeI-gpA_F1 and hA362-369_R and the sequence corresponding to the C-terminal domain of hASNase1 ($h_C$, residue 362-573) was amplified using the primers gpA352-359_F and hA_BamHI_R573. Primers are listed in Table 2. The chimera was then constructed by PCR fusion of fragment $h_N$ and $g_C$ or $g_N$ and $h_C$ using the appropriate primers and then subsequently cloned into the pBAD and pET vectors.

Cloning and Expression of the Selected Clones.

The isolated clones were cultured; the plasmid was extracted and sequenced. The corresponding genes were transferred to a pET vector (modified pET14b to include a His-SUMO tag, using the same primers as the one used for cloning into the pBAD vector) to allow the expression of the His-tagged protein in C41 (DE3) cells. The culture was carried out in 1 L of 2YT medium supplemented with 100 µg/mL ampicillin. Expression was induced with 0.1 mM IPTG and cells were grown overnight at 18° C. Cells were harvested, lysed and purified as previously described for the wild type gpASNase1 (Schalk, et al. (2014) *J. Biol. Chem.* 289:33175-86). The protein was eluted in a 25 mM Tris-HCl pH 7.5, 200 mM KCl, 500 mM imidazole buffer and dialyzed against the same buffer containing no imidazole but 1 mM of DTT. Expression and purification of the *E. coli* ansB enzyme was described previously (Schalk, et al. (2014) *J. Biol. Chem.* 289:33175-86).

Kinetic Assays.

The catalytic activity of the clones was determined using a spectroscopic NADH-dependent enzyme-coupled assay (Fernandez, et al. (2013) *Int. J. Clin. Exp. Med.* 6:478-487; Hejazi, et al. (2002) *Biochem. J.* 364:129-136), which measures the production of L-aspartic acid (Asp) through the 1:1 oxidation of reduced NADH. The conversion of NADH to NAD was measured spectrophotometrically as a decrease in absorbance at 340 nm at 37° C. All measurements were taken in triplicate in a buffer containing 100 mM Tris pH 7.5, 0.4 mM α-ketoglutarate and 0.4 mM NADH with 50 nM (hASNase1, hN-gC); 10 nM (gpASNase1, gN-hC, 63-hC, 64-hC, 65-hC, SA-hC) or 3 nM (ansB) enzyme. Glutamic-oxalacetic transaminase (Sigma) and malic dehydrogenase (Sigma) were helper enzymes for the coupled enzymatic reactions; 5 and 1 unit were used, respectively. Data were fit to the Michaelis-Menten equation using SigmaPlot (Systat Software Inc). Due to the cooperative nature of hASNase1, this enzyme was analyzed using the Hill equation.

Cell Culture.

The LOUCY (Ben-Bassat, et al. (1990) *Cancer Genet. Cytogenet.* 49(2):241-8) and SUP-B15 (ATCC CRL-1929) cell lines are described in the art. All cell lines were analyzed by STR (Short Tandem Repeat) and confirmed to match 100% to corresponding STR profile data from the Global Bioresource Center ATCC. All cell lines were verified to be *mycoplasma* free. LOUCY and SUP-B15 lines were cultivated in a humid atmosphere (5% C02, 37° C.) using RPMI 1640 media supplemented with 10% FBS (Hyclone) and 1× penicillin-streptomycin solution (Invitrogen). L-Glutamine was added directly into cell cultures to a final concentration of 2 mM. Ninety µL aliquots of cell suspension (5×10$^5$ cells per mL) were cultured in triplicate in round-bottomed 96-well microtiter plates in the presence of 10 µL of either DPBS (Dulbecco's phosphate-buffered saline, Mediatech) or different L-asparaginases to a final concentration ranging from 0.00001 to 0.1 IU/mL. After incubating the plates for 4 days at 37° C. in humidified air containing 5% $CO_2$, 11 µL of Alamar Blue (Invitrogen) was added to a final concentration of 10% (v/v) and the plates were incubated for an additional two hours, followed by reading of the fluorescence signal. The leukemic cell viability was calculated as percentage of fluorescence counts in the presence of L-asparaginase versus that in the DPBS control.

Development of the Selection Systems.

To create a selection system for L-asparaginase activity, a bacterial strain whose growth is dependent on any product of the enzymatic reaction was required. Since L-asparaginase catalyzes the hydrolysis of Asn into Asp and ammonia, two selections systems were developed and tested: one employing a bacterial strain dependent on the reaction product ammonium as the sole nitrogen source and the other uses a strain auxotroph for Asp.

Strain BW2Δ:

Dependence on L-Asparaginase Reaction for Nitrogen Source. All life forms require a nitrogen source. For *E. coli* grown in a minimal media such as M9, the nitrogen source is usually obtained in the form of $NH_4Cl$ salt. However, in the absence of $NH_4Cl$, it was verified that the *E. coli* BW strain used in this study could grow using 2 mM Asn in the media. This demonstrates that *E. coli* can use Asn as a nitrogen source through the activity of its endogenous L-asparaginases. To make the BW *E. coli* strain dependent on the $NH_4Cl$ produced by exogenous L-asparaginase activity, two endogenous L-asparaginase genes (ansA and ansB) were deleted from the *E. coli* BW parental strain, which were then referred to as BW2Δ. Notably, the third endogenous L-asparaginase (iiiA) was not deleted, since it has a very high $K_m$ value for Asn. Indeed, under the experimental conditions, even with 2 mM Asn in the media, growth of the BW2Δ strain was greatly impaired.

Strain BW5Δ:

Dependence on L-Asparaginase Reaction for Aspartate. *E. coli* can generate Asp by hydrolyzing Asn (the L-asparaginase reaction) or by an aminotransferase reaction. Indeed, the parental BW strain grows well in M9 media independently and with no effect by Asp supplementation. To create an *E. coli* strain auxotrophic for Asp, all three endogenous L-asparaginase genes (ansA, ansB, and iiiA) were deleted, as were the two relevant aminotransferase genes (aspC and tyrB). The strain with these five genes deleted was referred to as strain BW5Δ. To ensure that the strain BW5Δ acquired Asp auxotrophy, growth was tested in minimal media M9 with and without Asp supplementation. It was observed that without supplementing the media with Asp, BW5Δ could not grow. However, growth was observed in the Asp supplemented conditions.

Use of the BW2Δ and BW5Δ Strains to Select Clones Expressing L-Asparaginase. To investigate whether these bacterial strains can be used as selection systems for L-asparaginase activities and foremost whether they would allow the differentiation between L-asparaginases based on their $K_m$ property, the growth of the BW2Δ and BW5Δ strains expressing either an L-asparaginase with a low $K_m$ or an L-asparaginase with a high $K_m$ was analyzed. Human L-asparaginase type I (hASNase1), the protein target to be evolved, is characterized by a $K_m$ for Asn in the millimolar range (Karamitros & Konrad (2014) *J. Biol. Chem.* 289: 12962-75; Schalk, et al. (2014) *J. Biol. Chem.* 289:33175-86) and was thus used as the high $K_m$ L-asparaginase. The guinea pig L-asparaginase I (gpASNase1) was characterized as having a $K_m$ for Asn in the micromolar range (Schalk, et al. (2014) *J. Biol. Chem.* 289:33175-86) and was thus used as the low $K_m$ L-asparaginase. Both genes encoding the respective L-asparaginase were cloned into the pBAD vector in order to have well-controlled protein expression.

In the first screening system, which is based on the L-asparaginase reaction supplying the sole source of nitrogen, BW2Δ was transformed with pBAD (control vector), pBAD_hASNase1 (high $K_m$ enzyme) or pBAD_gpASNase1 (low $K_m$ enzyme). The transformed cells were grown in M9 medium lacking $NH_4Cl$ but supplemented with an increasing concentration of Asn. The expectation was that a low Asn concentration would preferentially promote the growth of the bacteria carrying the pBAD_gpASNase1 plasmid, coding for the low $K_M$ enzyme. Results show that growth of both BW2Δ pBAD_hASNase1 and pBAD_gpASNase1 did in fact depend on the concentration of Asn (i.e., enhanced concentration of Asn leading to better growth). However, per Asn concentration, there was not a significant difference of growth between BW2Δ pBAD_hASNase1 and pBAD_gpASNase1, e.g., at 0.2 mM Asn, BW2Δ bacteria that express the low $K_m$ gpASNase1 enzyme did not form significantly more or bigger colonies than bacteria that express the high $K_m$ hASNase1 enzyme. In sum, this screening system was found to be not suitable for discriminating between L-asparaginases that differ in their Asn $K_m$ value.

In the second screening system, which is based on Asp auxotrophy, BW5Δ was similarly transformed with pBAD, pBAD_hASNase1 or pBAD_gpASNase1. The transformed cells were grown in complete M9 media supplemented with increasing concentration of Asn. Growth of BW5Δ pBAD_hASNase1 and pBAD_gpASNase1 were found to be dependent on the concentration of Asn. Interestingly, at 2 mM Asn, which represents a concentration at which the guinea pig enzyme is saturated with substrate ($K_m$=50 μM) and the human enzyme is only partially saturated ($K_m$=3,500 μM), hASNase1 and gpASNase1 transformed BW5Δ strains show similar growth. In other words, at this relatively high Asn concentration, the BW5Δ strain cannot be used to distinguish between those bacteria that express a low $K_m$ L-asparaginase to those that express a high $K_m$ enzyme. In contrast, at lower concentrations of the substrate Asn, only BW5ΔpBAD_gpASNase1 is capable of growing. Indeed, at 0.2 mM Asn, a concentration of Asn well below the $K_m$ of hASNase1 but above the $K_m$ of gpASNase1, colonies of BW5ΔpBAD_gpASNase1 developed whereas BW5Δ pBAD_hASNase1 could not grow. Noteworthy, this growth difference was found to be independent of enzyme expression level since no change in growth was noticed when arabinose (the inducer for protein expression) was used in the range 0.0002%-0.2%. Taken together, the results suggest that the difference in growth seen between BW5Δ expressing hASNase1 and BW5Δ expressing gpASNase1 on minimal media plates directly reflects the $K_m$ of the respectively expressed L-asparaginase.

The conclusion from this initial set of experiments is that the screen based on the L-asparaginase reaction supplying the nitrogen (using the BW2Δ strain) does not differentiate well enough between high and low $K_m$ enzymes, whereas the screen based on the L-asparaginase reaction supplying the amino acid Asp (using the BW5Δ strain) does indeed discriminate between enzymes with differing affinities to Asn—at low Asn concentration, only the bacteria expressing the low $K_m$ L-asparaginase forms colonies. Hence, all further selection work aimed at discovering a human L-asparaginase variant that has acquired a low $K_m$ was performed with the BW5Δ *E. coli* strain.

DNA Family Shuffling. DNA family shuffling is an alternative method for generating genetic diversity. The protein sequences of hASNase1 and gpASNase1 contain 573 and 565 amino acids, respectively, and are 69.8% identical at the amino acid level (differing by 170 amino acids). Working with synthetic codon-optimized versions of both hASNase1 (SEQ ID NO:35) and gpASNase1 (SEQ ID NO:36), the genes encoding hASNase1 and gpASNase1 show 75% identity at the DNA level. As mentioned herein, hASNase1 has a $K_m$ of 3.5 mM for Asn, whereas the $K_m$ of the guinea pig enzyme was determined to be 50 μM (Table 3). The DNA shuffling method was used to recombine the two L-asparaginases in order to obtain a chimera that displays the low $K_m$ of the guinea pig but with as high as possible amino acid homology with the human enzyme. The shuffled fragments were then cloned into the pBAD vector. The resulting chimeric library was used to transform the BW5Δ strain. The presence of mutants possessing a low $K_m$ was discovered using the selection protocol as described above. Four clones (#63, #64, #65 and # SA) were isolated from M9 plates at an Asn concentration of 0.2 mM. Sequence analyses of these clones revealed a shuffling pattern with recombination events occurring predominantly in the N-terminal (i.e., catalytic) domain; one of the selected clones (# SA) carried a mutation that introduced a premature stop codon (STOP) that was beyond the catalytic domain (FIG. 1).

Swapping of the C-terminal domain. To minimize immunogenicity against GpA, an enzyme was sought that was as identical as possible to the human L-asparaginase but that had the low $K_m$ property of the guinea pig/*E. coli* type II enzymes. Shuffling experiments suggested that a chimera that had the guinea pig L-asparaginase domain followed by the human C-terminal domain would still retain the favorable kinetic properties of the gpASNase1 but would have an increased sequence identity with the human enzyme.

Accordingly, two chimeras were generated; one, which was referred to as $h_N$-$g_C$ and included the human N-terminal domain fused to the guinea pig C-terminal domain, and the second, which was referred to as $g_N$-$h_C$ and included the guinea pig N-terminal domain fused to the human C-terminal domain (FIG. 1, Table 3). In vitro kinetic characterization of these chimeras validated the prediction, with $h_N$-$g_C$ displaying kinetic properties similar to hASNase1 and $g_N$-$h_C$ displaying kinetic properties similar to gpASNase1 (Table 4).

This result demonstrates that the C-terminal domain of GpA does not influence the catalytic activity of the L-asparaginase and most importantly does not negatively affect the $K_m$. Since the goal was to identify a clone with gpASNase1 kinetic properties but with the highest sequence homology to hASNase1, the four clones, #63, #64, #65 and # SA, were engineered by replacing their shuffled C-terminal domain with the exact sequence of the human C-terminal domain (FIG. 1). The engineered clones, namely $63_N$-$h_C$, $64_N$-$h_C$, $65_N$-$h_C$ and $SA_N$-$h_C$, displayed respectively 85.7%, 91.1%, 87.1% and 91.6% identity with the wild-type hASNase1 sequence (Table 3 and FIG. 2A-2B).

TABLE 3

| Enzyme Name | # of Residues | % Identity to hASNase1 | SEQ ID NO: |
|---|---|---|---|
| hASNase1 | 573 | 100 | 2 |
| ansB | 326 | 26.9 | — |
| gpASNase1 | 565 | 69.8 | 1 |
| $g_N$-$h_C$ | 571 | 83.4 | 37 |
| $h_N$-$g_C$ | 567 | 86.5 | 38 |
| $63_N$-$h_C$ | 571 | 85.7 | 39 |
| $64_N$-$h_C$ | 571 | 91.1 | 40 |
| $65_N$-$h_C$ | 571 | 87.1 | 41 |
| $SA_N$-$h_C$ | 571 | 91.6 | 42 |

Catalytic Properties of the Variants.

For determining the precise kinetic properties of $63_N$-$h_C$, 64N-$h_C$, $65_N$-$h_C$ and $SA_N$-$h_C$, the genes encoding these enzymes were sub-cloned into a pET14b expression vector and expressed in C41 *E. coli* cells. The purified clones were tested for their L-asparaginase activity (Table 4). *E. coli* L-asparaginase ansB was also included in order to compare the clones to an L-asparaginase approved for cancer therapy. It was observed that the four clones selected for by directed evolution and carrying the C-terminal domain of hASNase1 displayed high sequence identity with hASNase1 (>85%) but kinetic properties similar to gpASNase1 with a $K_m$ in the micromolar range. Clone $63_N$-$h_C$ (85.7% identity with the hASNase1 sequence) displayed the lowest $K_m$ at 47 µM. Clone $SA_N$-$h_C$ had the highest sequence identity to hASNase1 (91.6% identity), but this clone had a somewhat higher Asn $K_m$ of 165 µM. The observed Asn hydrolysis rates of the enzymes at 50 µM Asn ($k_{obs@50\ \mu M}$) were compared as this is a relevant blood Asn concentration (Ollenschlager (1988) *Eur. J. Clin. Invest.* 18:512-6). The *E. coli* ansB $k_{obs@50\ \mu M}$ was found to be 41±0.3 sec$^{-1}$ and that of wild-type gpASNase1 was 20 sec$^{-1}$. Importantly, the $k_{obs@50\ \mu M}$ values for the humanized clones were also in this range, being 17 sec$^{-1}$, 10 sec$^{-1}$, 17 sec$^{-1}$ and 6 sec$^{-1}$ for clones $63_N$-$h_C$, $64_N$-$h_C$, $65_N$-$h_C$ and $SA_N$-$h_C$, respectively.

TABLE 4

| Enzyme name | $k_{cat}$ (sec$^{-1}$) | $K_m$ (µM) | $k_{cat}/K_m$ (sec$^{-1}$µM$^{-1}$) | $k_{obs}$ (sec$^{-1}$) @50 µM |
|---|---|---|---|---|
| hASNase1* | 17 ± 0.8 | 3500 ± 300 | 0.005 | ND |
| ansB | 48 ± 1 | 11 ± 1 | 4.4 | 41 ± 0.3 |
| gpASNase1 | 41 ± 2 | 50 ± 7 | 0.8 | 20 ± 1 |
| $g_N$-$h_C$ | 24 ± 1 | 35 ± 4 | 0.7 | 14 ± 1 |
| $h_N$-$g_C$ | 14 ± 0.5 | 3800 ± 120 | 0.004 | ND |
| $63_N$-$h_C$ | 32 ± 0.6 | 47 ± 3 | 0.7 | 17 ± 0.5 |
| $64_N$-$h_C$ | 60 ± 2 | 202 ± 17 | 0.3 | 10 ± 1 |
| $65_N$-$h_C$ | 40 ± 1 | 74 ± 5 | 0.5 | 17 ± 1 |
| $SA_N$-$h_C$ | 32 ± 2 | 165 ± 19 | 0.2 | 6 ± 1 |

*Kinetic parameters using the Hill-equation (n = 2.1)
ND: not determined

Cell Culture Evaluation of the Humanized L-Asparaginase Clones.

To determine whether GpA enzyme exhibited anti-ALL activity, human T-ALL LOUCY and B-ALL SUP-B15 cell lines were exposed to increasing concentrations of gpASNase1. The results of this analysis indicated that gpASNase1 exhibited an IC$_{50}$ of 0.00015 IU/ml and 0.00036 IU/ml for the LOUCY and SUP-B15 cell lines, respectively (Table 5). Notably, these IC$_{50}$ values are comparable to those of the *E. coli* type II enzyme.

Chimeras of hASNase1 and gpASNase1 were also evaluated for their anti-ALL potency. Clones $g_N$-$h_C$, $63_N$-hC and $65_N$-hC were selected for these experiments since these clones have the lowest Asn $K_m$ (35, 47 and 74 µM, respectively) and thereby have activities most similar to that of gpASNase1 (50 µM). Due to the higher $K_m$ value of $65_N$-hC, this clone had the highest IC$_{50}$ value compared to the other enzymes but was still very effective in killing both the T-ALL and B-ALL cells (IC$_{50}$ in the mIU/mL range; Table 5). Clones $g_N$-$h_C$ and $63_N$-$h_C$ proved to be very similar in their cell-killing power compared to gpASNase1. This is especially notable for clone $63_N$-$h_C$, since this clone increased the percent identity to hASNase1 from 69.8% as present in gpASNase1 to 85.7%.

TABLE 5

| | IC$_{50}$ value (IU/mL × 10$^{-4}$) | |
|---|---|---|
| Enzyme Name | LOUCY | SUB-B15 |
| gpASNase1 | 1.5 | 3.6 |
| $g_N$-$h_C$ | 2.9 | 5.7 |
| $63_N$-$h_C$ | 3.8 | 6.0 |
| $65_N$-$h_C$ | 85.3 | 13.0 |
| *E. coli* type II | 3.5 | 3.7 |

In summary, this analysis identified humanized variants of GpA that had the required low $K_m$ property. Two of the identified clones, 63N-hC and 65N-hC, respectively shared 85.7% and 87.1% amino acid sequence identity with the hA-FL but had a $K_m$ similar to full-length GpA. These clones possess 100- to 140-fold enhanced catalytic efficiency compared to full length hASNase1. Notably, these highly human-like L-asparaginases maintain their in vitro ALL killing potential.

Example 3: Humanized GpA Variants Produced Via a Structured-Based Approach

As an alternative to DNA shuffling and domain swapping, a structure-based approach was taken to humanize the GpA enzyme and reduce the immunogenicity of the same. For this approach, the truncated GpA369 variant (SEQ ID NO:5) was modified. The crystal structure of GpA was examined and predictions were made as to which residues at the surface of the enzyme could be mutated to the corresponding amino acids in hASNase1, and whose presence would not be detrimental to the activity or stability of the enzyme. The candidate surface residues were divided into three groups based upon the likelihood of having a possible impact on activity or stability of GpA (Group 1, no impact; Group 2, likely no impact; and Group 3, possible impact) (Table 6).

TABLE 6

| Group 1 | | Group 2 | | Group 3 | |
|---|---|---|---|---|---|
| GpA residue[1] | Human residue[2] | GpA residue[1] | Human residue[2] | GpA residue[1] | Human residue[2] |
| Q23 | R23 | H10 | R10 | R147 | H147 |
| K25 | E25 | D91 | A91 | K193 | R193 |
| K48 | E48 | D92 | E92 | D217 | E217 |
| Q52 | R52 | Q108 | H108 | R301 | Q301 |
| Q54 | R54 | H236 | Q236 | | |
| K98 | Q98 | S250 | A250 | | |
| E101 | K101 | | | | |
| S121 | F121 | | | | |
| G122 | A122 | | | | |
| H134 | Q134 | | | | |
| N233 | S233 | | | | |
| Q288 | E288 | | | | |
| E344 | D346 | | | | |

TABLE 6-continued

| Group 1 | | Group 2 | | Group 3 | |
|---|---|---|---|---|---|
| GpA residue[1] | Human residue[2] | GpA residue[1] | Human residue[2] | GpA residue[1] | Human residue[2] |
| L360 | P362 | | | | |
| T362 | S364 | | | | |
| A363 | V365 | | | | |
| D364 | E366 | | | | |
| L365 | E367 | | | | |
| H366 | R368 | | | | |
| Q367 | R369 | | | | |
| S368 | P370 | | | | |

[1]Reference sequence GpA369 (SEQ ID NO: 5).
[2]Corresponding residue in reference sequence hASNase1 (SEQ ID NO: 2).

A GpA variant containing all the Group 1 mutations, the combination of Groups 1 and 2 mutations, and the combination of Groups 1, 2 and 3 mutations were prepared (Table 7). The GpA variants were recombinantly expressed and found to retain 100% of the wild-type activity and stability.

In vivo stability data suggested a potential cleavage of one of the surface exposed loops present in the GpA enzyme. In particular, the data suggested different stabilities between proteins having the sequence of loop 1 as present in hASNase1 (loop1$^{hum}$, residues 57-62: SEDTLV (SEQ ID NO:43)) to proteins having the sequence as present in GpA (loop1$^{gp}$, residues 57-62: PDHALA (SEQ ID NO:44)). Accordingly, GpA variants containing combinations of Group 1, 2 and 3 mutations were further mutated to include the loop1$^{hum}$ sequence (Table 7). Again, the Loop1 GpA variants were recombinantly expressed and found to retain 100% of the wild-type activity and stability.

TABLE 7

| | % Identity | | SEQ ID |
|---|---|---|---|
| Variant Name | GpA359* | hASNase1⁺ | NO: |
| GpA369 | 100% | 72.2% | 5 |
| GpA369(hum)-Group 1 | 96.4% | 77.9% | 45 |
| GpA369(hum)-Group 1 + 2 | 94.7% | 79.5% | 46 |
| GpA369(hum)-Group 1 + 2 + 3 | 93.6% | 80.6% | 47 |
| GpA369(hum)-Group1-loop1$^{hum}$ | 95.0% | 79.2% | 48 |
| GpA369(hum)-Group1 + 2-loop1$^{hum}$ | 93.3% | 80.9% | 49 |
| GpA369 (hum)-Group1 + 2 + 3-loop1$^{hum}$ | 92.2% | 81.9% | 50 |

*Identity determined over the entire length of the catalytic domain of the variant (residues 1-359) as compared to GpA359 (SEQ ID NO: 3).
⁺Identity determined over the entire length of the variant as compared to residues 1-371 of hASNase1, since the human enzyme has a two-residue insertion at residue 311.

Example 4: Mutation of Surface Cysteine Residues for PEGylation

PEGylation is known to increase in vivo circulation time. PEG molecules can be readily conjugated to cysteine residues of a protein of interest by maleimide-based PEGylation chemistry. GpA369 and humanized GpA369 variants contain five intrinsic cysteine residues, Cys79, Cys173, Cys198, Cys296 and Cys299. Based on crystal structure analysis, Cys173 and Cys296 are buried and thus predicted to not affect PEGylation. Cys299 was considered to be less accessible than Cys198 and contribute to tetramer stabilization. Attempts to exchange Cys299 to either Ala or Ser to avoid PEGylation at this site resulted in unstable proteins. Conversely, mutating the cysteine residue at position 198 to an alanine (GpA369-C198A, SEQ ID NO:51), serine (GpA369-C198S, SEQ ID NO:52) or valine (GpA369-C198V, SEQ ID NO:53) yielded equally stable and active proteins compared to the reference GpA369 enzyme. Moreover, maleimide-PEGylation of the GpA369-C198A, GpA369-C198S and GpA369-C198V proteins, now containing only a single reactive surface cysteine (Cys79), resulted in a homogenous product.

The degree of biologics protection by PEGylation depends on the structure and the complexity of the PEG agent, but in most cases, single-site PEGylation is not enough to cover the whole macromolecule. Therefore, additional GpA variants were generated, which contained between one and five surface cysteine residues. In this respect, the structure of GpA was analyzed in order to identify regions of residues that could be mutated to cysteines for multi-site PEGylated products. Useful regions must be on the surface, must be distant from oligomerization interfaces (GpA is a tetramer, so PEGylating a residue near an interface could be detrimental to the activity of the enzyme), and include residues that point outwards. Regions of GpA meeting these criteria are listed in Table 8.

TABLE 8

| Region | | | | |
|---|---|---|---|---|
| 1 | 2 | 3 | 4 | 5 |
| R40 | E131 | R253 | E340 | S358 |
| K48 | N132 | Q257 | E344 | S359 |
| E49 | K221-D226 | K261 | R345 | |
| Q52 | N233 | Q281-R284 | Q347 | |
| Q54 | | Q288 | K352 | |
| D58 | | | | |

Amongst the possible residues that could be mutated (Table 8), E49 from Region 1, K225 from Region 2, Q257 from Region 3 and E340 from Region 4 were identified as good candidates for mutation to a cysteine. Variants of GpA369-C198 and GpA369(hum)-Group1+2+3-C198, which included one or more of K225C, E340C, E49C and Q257C mutations were generated (Table 9).

TABLE 9

| | % Identity | | SEQ |
|---|---|---|---|
| Variant Name | GpA359* | hASNase1⁺ | ID NO: |
| GpA369-C198A | 99.7% | 72.0% | 51 |
| GpA369-C198A + K225C | 99.4% | 71.7% | 54 |
| GpA369-C198A + K225C + E340C | 99.2% | 71.7% | 55 |
| GpA369-C198A + K225C + E340C + E49C | 98.9% | 71.4% | 56 |
| GpA369-C198A + K225C + E340C + E49C + Q257C | 98.6% | 71.2% | 57 |
| GpA369(hum)-Group1 + 2 + 3-loop1$^{hum}$-C198A | 91.9% | 81.7% | 58 |
| GpA369(hum)-Group1 + 2 + 3-loop1$^{hum}$-C198A + R52C | 91.9% | 81.4% | 59 |
| GpA369(hum)-Group1 + 2 + 3-loop1$^{hum}$-C198A + R52C + K225C | 91.6% | 81.1% | 60 |
| GpA369(hum)-Group1 + 2 + 3-loop1$^{hum}$-C198A + R52C + K225C + E340C | 91.4% | 81.1% | 61 |
| GpA369(hum)-Group1 + 2 + 3-loop1$^{hum}$-C198A + R52C + K225C + E340C + Q281C | 91.1% | 80.9% | 62 |

*Identity determined over the entire length of the catalytic domain of the variant (residues 1-359) as compared to GpA359 (SEQ ID NO: 3).
⁺Identity determined over the entire length of the variant as compared to residues 1-371 of hASNase1, since the human enzyme has a two-residue insertion at residue 311.

Each of the variants listed in Table 9 were recombinantly expressed, purified and PEGylated with one or more of mPEG-10K, mPEG-20K and mPEG-40K (Table 10). As determined by SDS-PAGE analysis, the size of the PEGylated enzymes increased with an increase in the number of active cysteines. For example, using maleimide-PEG10K, GpA369(hum)-C198A migrated at a higher molecular weight after PEGylation (due to the extra 10K Da supplied by the PEG), and GpA369(hum)-C198A+R52C migrated at an even higher apparent molecular weight since this variant can react with two PEG molecules (for a total of an extra 20K Da supplied by two 10K molecules linked to the enzyme). Of note, the GpA369-C198A-K225C-E340C-E49C-Q257C mutant was prepared, expressed, purified and PEGylated with mPEG-10K. However, PEGylation of this variant with mPEG-10K resulted in multiple-species product. Chaperone 60KDa was present with at a 1:1 ratio with this protein, suggesting that the GpA369-C198A-K225C-E340C-E49C-Q257C mutant was not well folded.

TABLE 10

| Variants | $k_{obs}$ at 2 mM ASN (sec$^{-1}$) | % vs GpA-FL |
|---|---|---|
| Full length GpA (GpA-FL) | 41 | 100 |
| GpA369 | 44 | 107.3 |
| GpA369-C198A | 43.3 | 105.6 |
| GpA369-C198A + K225C | 41.4 | 100.9 |
| GpA369-C198A + K225C + E340C | 42.4 | 103.4 |
| GpA369-C198A + K225C + E340C + E49C | 41.6 | 101.5 |
| 10K-PEGylated-GpA369-C198A | 83.3 | 203.2 |
| 20K-PEGylated-GpA369-C198A | 83.7 | 204.1 |
| 40K-PEGylated-GpA369-C198A | 76.5 | 186.6 |
| 10K-PEGylated-GpA369-C198A + K225C | 92.6 | 225.9 |
| 20K-PEGylated-GpA369-C198A + K225C | 88.0 | 214.6 |
| 40K-PEGylated-GpA369-C198A + K225C | 92.8 | 226.3 |
| 10K-PEGylated-GpA369-C198A + K225C + E340C | 84.9 | 207.1 |
| 10K-PEGylated-GpA369-C198A + K225C + E340C + E49C | 83.9 | 204.6 |

*PEGylation was with linear PEG.

To further assess the PEGylation of the variants, different PEG:protein ratios were used. For this analysis, 2 mg/mL of GpA369-C198A was used along with 2-, 10-, and 20-fold excess m-PEG10K linear. Further, analysis was carried out to determine the effect of adding 5 mM beta-mercaptoethanol after the PEGylation reactions were completed, and including additives such as 10 mM or 100 mM glycine or 10 mM aspartic acid during the PEGylation reaction. This analysis indicated that a molar ratio of 20:1 of maleimide PEG:protein was needed to ensure full PEGylation of GpA369 variants. Further, the addition of beta-mercaptoethanol was found to provide homogenous product, whereas glycine or aspartic acid should be excluded in the PEGylation reaction.

In addition to linear maleimide-PEG10K, the GpA369 variants with PEGylated with linear maleimide-PEG20K, linear maleimide-PEG40K two-branched maleimide-PEG20K, four-arm maleimide-PEG10K, and Y-shape maleimide-PEG40K. PEGylation with each of these different types of PEG was observed. Notably, the PEGylated variants showed a significant increase in L-asparaginase activity compared to the naked variants of GpA369 (Table 10).

Example 5: Mutation of Surface Lysine Residues for PEGylation

Most conventional biotherapeutics are PEGylated on lysine residues, where the epsilon amino group of the lysine side chain reacts with the PEG molecule. Lysine is a common amino acid present at the surface of proteins. Therefore, PEGylation using this strategy often results in a product of low homogeneity, with a variable number of PEG molecules linked to the protein.

To increase homogeneity, lysine resides of GpA that are in close proximity to another lysine residue were replaced with a residue that would not react with PEG. In addition, residues having a possible negative impact on the structural integrity and thus the enzymatic activity of the tetrameric L-asparaginase were replaced with surface lysine residues in order to have the whole enzyme's surface fully and evenly protected.

Using this strategy, truncated GpA variants having the mutations listed in Table 11 were considered to be of use in this invention.

TABLE 11

| Variant Name | % Identity GpA359* | % Identity hASNase1[†] | SEQ ID NO: |
|---|---|---|---|
| GpA369-Q54K + D91K + K223D + S311K | 98.9% | 72.5% | 63 |
| GpA369(hum)-Group1 + 2 + 3-C198A-R54K + A91K + K223D + S311K | 92.8% | 80.1% | 64 |
| GpA369 (hum) -Group1 + 2 + 3-loop1$^{hum}$-C198A-R54K + A91K + K223D + S311K | 91.4% | 81.4% | 65 |
| GpA369 (hum) -Group1 + 2 + 3-loop1$^{hum}$-C198A-S7K + A53K + E58K + Q98K + Q106K + S233K + O257K + O281K + S311K + E340K | 90.3% | 79.2% | 86 |

*Identity determined over the entire length of the catalytic domain of the variant (residues 1-359) as compared to GpA359 (SEQ ID NO: 3).
[†]Identity determined over the entire length of the variant as compared to residues 1-371 of hASNase1, since the human enzyme has a two-residue insertion at residue 311.

To demonstrate the activity, stability and PEGylation via lysine residues, the GpA369(hum)-Group1+2+3-C198A-R54K+A91K+K223D+S311K variant was generated, recombinantly expressed, purified, and PEGylated using different PEG:protein ratios. This analysis showed that a molar ratio of more than 20:1 of amine PEG versus protein was needed to ensure full PEGylation of the GpA369 variant. It was also observed that additives such as DTT and glycerol should be excluded in the PEGylation reaction. Different size and linker types were tested, including Methoxy PEG Succinimidyl Carbonate 10K (mPEG-SC-10K), mPEG-Succinimidyl Carboxy Methyl Ester 5K (mPEG-SCM-5K) and mPEG-Succinamide Succinimidyl Ester 5K (mPEG-SAS-5K). Notably, none of the PEGylated products exhibited any loss in L-asparaginase activity compared to the naked version (Table 12).

TABLE 12

| Variants | $k_{obs}$ at 2 mM ASN (sec$^{-1}$) | % vs GpA-FL |
|---|---|---|
| Full length GpA (Gpa-FL) | 41 | 100 |
| GpA369(hum)-Group1 + 2 + 3-C198A-R54K + A91K + K223D + S311K | 69.5 | 169.5 |
| mPEG-SC-10K-PEGylated-GpA369(hum)-Group1 + 2 + 3-C198A-R54K + A91K + K223D + S311K | 69.3 | 169.1 |

TABLE 12-continued

| Variants | $k_{obs}$ at 2 mM ASN (sec$^{-1}$) | % vs GpA-FL |
|---|---|---|
| mPEG-SCM-5K-PEGylated-GpA369(hum)-Group1 + 2 + 3-C198A-R54K + A91K + K223D + S311K | 70.9 | 172.9 |
| mPEG-SAS-5K-PEGylated-GpA369(hum)-Group1 + 2 + 3-C198A-R54K + A91K + K223D + S311K | 66.9 | 163.2 |

Example 6: Tags for Increasing In Vivo Half-Life

Efficacy of L-asparaginase is related to the in vivo half-life of the drug; the longer the half-life, the longer the enzyme acts to hydrolyze the blood asparagine. Accordingly, to increase the in vivo half-life of L-asparaginase variants disclosed herein, tags are fused to the N-terminus of the L-asparaginase. Such tags include a histidine tag, a yeast SUMO tag; a human SUMO tag; a His$_6$-human SUMO tag where the SUMO tag can be one of the four homologous SUMO domains present in humans (SUMO-1, SUMO-2, SUMO-3 or SUMO-4); and an albumin-binding peptide tag. Each of the tags can increase the circulation time of the L-asparaginase enzyme. In addition, combinations of tags can be used. In particular, the SA21 and SUMO tags can be combined to obtain variants with an even further extended half-life.

The Histidine Tag.

The DNA sequence specifying a string of six to nine histidine residues is frequently used in vectors for production of recombinant proteins. The result is expression of a recombinant protein with a 6xHis or poly-His tag fused to its N- or C-terminus.

Expressed His-tagged proteins can be purified and easily detected thereby providing a means of specifically purifying or detecting the recombinant protein without a protein-specific antibody or probe. Kits are commercially available to His-tag proteins.

SUMO Modification.

It has been found that SUMO as an N-terminal fusion partner enhances functional protein production in prokaryotic and eukaryotic expression systems, based upon significantly improved protein stability and solubility.

Following the expression and purification of the fusion protein, the SUMO-tag can be cleaved by specific (SUMO) proteases via their endopeptidase activity in vitro to generate the desired N-terminus of the released protein partner. SUMO tag expression systems are commercially available. In some embodiments, the SUMO tag is a yeast SUMO tag (e.g., Smt3 (SEQ ID NO:66)). In other embodiments, the SUMO tag is a human SUMO tag (e.g., SUMO-1 (SEQ ID NO:67), SUMO-2 (SEQ ID NO:68), SUMO-3 (SEQ ID NO:69) or SUMO-4 (SEQ ID NO:70)).

His-SUMO Modification.

Combining a histidine (e.g., 1x-6xHis) tag and SUMO modification provides for efficient purification, increased expression and solubility, as well as increased half-life of L-asparaginases. Expression systems for providing the His-SUMO modification to a protein of interest are commercially available. See, e.g., the CHAMPION pET SUMO protein expression system (Invitrogen).

Albumin Binding Domain. Using phage display, a series of peptides that bind to serum albumin from multiple species have been identified (Dennis, at al. (2002) *J. Biol. Chem.* 277(38):35035-35043; US 2016/0185874; and US 2004/0001827). One of these peptides, called SA21, was found to have an extended serum half-life. Exemplary albumin binding peptides include, but are not limited to, SA20 (QRLIEDICLPRWGCLWEDDF; SEQ ID NO: 71), SA21 (RLIEDICLPRWGCLWEDD; SEQ ID NO: 72), and SA31 (RLIEDICLPRWGCLW; SEQ ID NO: 73). By fusing such domains to the L-asparaginase enzyme disclosed herein, pharmacokinetic improvements are expected via non-covalent association with albumin. See Dennis, et al. (2002) *J. Biol. Chem.* 277(38):35035-35043; US 2016/0185874; and US 2004/0001827.

Exemplary truncated GpA variants with various tags are provided in Table 13.

TABLE 13

| GpA Variant | Tag | SEQ ID NO: |
|---|---|---|
| GpA369-C79K-C198A | N-terminal yeast SUMO + 1X-His | 74 |
| GpA369-C79K-C198A | N-terminal human SUMO-1 + 1X-His | 75 |
| GpA369-C198A | N-terminal SA21 | 76 |
| GpA369-C198A | C-terminal SA21 | 77 |
| GpA369-C79A-C198A | N-terminal yeast SUMO + 1X-His, C-terminal SA21 | 78 |
| GpA369-C198A | N-terminal human SUMO-1 + 1X-His, C-terminal SA21 | 79 |
| GpA (hum)$_{1-225}$-SA21-GpA (hum)$_{226-369}$ | SA21 engrafted between residues 225 and 226 of GpA | 93 |
| GpA (hum)$_{1-340}$-SA21-GpA (hum)$_{341-369}$ | SA21 engrafted between residues 340 and 341 of GpA | 94 |

Example 7: TRAIL-GpA Fusion Protein

TRAIL (TNF-related apoptosis inducing ligand) is a protein that induces cell death by apoptosis. Accordingly, a TRAIL-Asparaginase fusion protein is created to combine the activity of these two proteins. Using this fusion protein, the L-asparaginase component signals the cell to undergo apoptosis, and the TRAIL component induces cell death. By way of illustration, three tandem soluble domains of TRAIL (TRAIL$_{trimer}$) are fused, in-frame, with a truncated and humanized guinea pig L-asparaginase such as GpA369 (hum)-Group1+2+3 (SEQ ID NO:47) or GpA369(hum)-Group1+2+3-loop1$^{hum}$ (SEQ ID NO:50) to generate TRAIL$_{trimer}$-GpA or GpA-TRAIL$_{trimer}$ fusion proteins.

Efficacy of a fusion protein is assessed by culturing human acute myeloid leukemia MV4;11 cells in the presence of the fusion protein to a final concentration ranging from 0.0001 to 2.5 IU/ml. After incubating the plates for 4 days at 37° C. in humidified air containing 5% $CO_2$, Alamar Blue (Invitrogen) is added to a final concentration of 10% v/v, and the plates are incubated for an additional 4 hours followed by reading of the fluorescence signal. Leukemic cell viability is calculated as the percentage of fluorescence counts in the presence of L-asparaginase versus that in the DPBS control. This analysis will demonstrate that the active fusion protein possesses remarkably better killing activity against the MV4;11 cell line compared to the truncated and humanized guinea pig L-asparaginase alone.

In vivo efficacy of a fusion protein for killing leukemic cells is assessed by injecting 4-10 non-obese diabetic/severe combined immune-deficient γ (NSG) mice (The Jackson Laboratory) at 6 weeks of age with 150 μL DPBS containing 5×10$^6$ luciferase-positive MV4;11 cells. At regular time points, the bioluminescence is measured using the IVIS Lumina II imaging system (PerkinElmer). After engraftment (Day 0), the mice are treated every day for one week with an i.p. injection of 15 IU/mouse of the fusion protein. The bioluminescence signal is measured at day 0 and day 7. The results of this analysis will demonstrate a remarkable killing effect of the MV4;11 cells by the fusion protein.

Efficacy of the fusion protein against solid cancers, such as pancreatic and ovarian cancers, is also determined. Pancreatic cancer cell lines such as Panc-1 and MiaPaca2 and ovarian cancer cell lines such as OVCAR3 and OVCAR4 are treated with the fusion protein or GpA alone to a final concentration ranging from 0.0001 to 2.5 IU/ml, or TRAIL$_{trimer}$ at a concentration that corresponds to that used for the fusion protein. After incubating the plates for 4 days at 37° C. in humidified air containing 5% $CO_2$, Alamar Blue (Invitrogen) is added to a final concentration of 10% v/v, and the plates are incubated for an additional 4 hours followed by reading of the fluorescence signal. Cancer cell viability is calculated as the percentage of fluorescence counts in the presence of the fusion protein versus that in the DPBS control. This analysis will demonstrate that the active fusion protein possesses remarkably better killing activity against the cancer cell lines compared to TRAIL$_{trimer}$ or GpA alone.

What is claimed is:

1. A Guinea pig L-Asparaginase (GpA) variant, wherein said GpA variant comprises an amino acid sequence having at least 85% sequence identity to the sequence of amino acid residues 1 to 359 of SEQ ID NO: 1, and has one or more amino acid substitutions relative to SEQ ID NO: 1, said amino acid substitutions being selected from the group consisting of:

H10R, Q23R, K25E, K48E, Q52R, Q54R, P57S, DS8E, H59D, A60T, A62V, D91A, D92E, K98Q, E101K, Q108H, G122A, H134Q, R147H, K193R, D217E, N233S, H236Q, S250A, Q288E, R301Q, E344D, L360P, T362S, A363V, D364E, L365E, H366R, Q367R and S368P; and optionally further having one or more amino acid substitutions relative to SEQ ID NO: 1 selected from the group consisting of C198A, C198S, C198V, E49C, R52C, K225C, Q257C, Q281C, and E340C.

2. The GpA variant of claim 1, wherein the variant is truncated at a position between amino acid residues corresponding to positions 359 and 396 of SEQ ID NO: 1.

3. The GpA variant of claim 1, wherein the variant is truncated at the position corresponding to position 369 of SEQ ID NO: 1.

4. The GpA variant of claim 1, wherein the variant has a catalytic activity equal to or greater than wild-type GpA comprising the amino acid sequence of SEQ ID NO: 1.

5. The GpA variant of claim 1, further comprising a histidine tag, a SUMO tag, an albumin-binding domain, or a combination thereof.

6. A nucleic acid molecule comprising a nucleotide sequence encoding the GpA variant of claim 1.

7. An expression vector comprising the nucleic acid molecule of claim 6.

8. An isolated host cell comprising the nucleic acid molecule of claim 6.

9. A pharmaceutical composition comprising the GpA variant of claim 1 and a pharmaceutically acceptable excipient.

10. A method of treating cancer in a subject comprising administering an effective amount of the GpA variant of claim 1 to a subject in need thereof, thereby treating the subject's cancer.

11. The method of claim 10, wherein the cancer is selected from non-Hodgkin's lymphoma, leukemia, acute lymphoblastic leukemia, acute myeloid leukemia, B cell lymphoma, Burkitt's lymphoma, chronic myelocytic leukemia, chronic lymphocytic leukemia, and hairy cell leukemia.

12. A Guinea pig L-Asparaginase (GpA) variant comprising the amino acid sequence of SEQ ID NO: 45, SEQ ID NO: 46, SEQ ID NO: 47, SEQ ID NO: 48, SEQ ID NO: 49, SEQ ID NO: 50, SEQ ID NO: 51, SEQ ID NO: 54, SEQ ID NO: 55, SEQ ID NO: 56, SEQ ID NO: 57, SEQ ID NO: 58, SEQ ID NO: 59, SEQ ID NO: 60, SEQ ID NO: 61, SEQ ID NO: 62, SEQ ID NO: 63, SEQ ID NO: 64, SEQ ID NO: 65, or SEQ ID NO: 86.

13. The GpA variant of claim 12, further comprising a histidine tag, a SUMO tag, an albumin-binding domain, or a combination thereof.

14. The GpA variant of claim 12, further comprising three tandem soluble domains of TRAIL.

15. The GpA variant of claim 14, wherein the soluble domains of TRAIL comprise residues 115-281 of human TRAIL.

\* \* \* \* \*

UNITED STATES PATENT AND TRADEMARK OFFICE
CERTIFICATE OF CORRECTION

| | | |
|---|---|---|
| PATENT NO. | : 11,578,315 B2 | Page 1 of 1 |
| APPLICATION NO. | : 16/637070 | |
| DATED | : February 14, 2023 | |
| INVENTOR(S) | : Arnon Lavie, Hien-Anh Nguyen and Amanda Schalk | |

It is certified that error appears in the above-identified patent and that said Letters Patent is hereby corrected as shown below:

On the Title Page

Item (73) for Assignees, please delete "The Board of Trustees of the University of Illinois, Urbana, OH (US);" and insert the following in its place:
--The Board of Trustees of the University of Illinois, Urbana, IL (US);--

Signed and Sealed this
Thirteenth Day of February, 2024

Katherine Kelly Vidal
*Director of the United States Patent and Trademark Office*

SEQUENCE LISTING

```
<160> NUMBER OF SEQ ID NOS: 94

<210> SEQ ID NO 1
<211> LENGTH: 565
<212> TYPE: PRT
<213> ORGANISM: Cavia porcellus

<400> SEQUENCE: 1

Met Ala Arg Ala Ser Gly Ser Glu Arg His Leu Leu Ile Tyr Thr
1               5                   10                  15

Gly Gly Thr Leu Gly Met Gln Ser Lys Gly Val Leu Val Pro Gly
                20                  25                  30

Pro Gly Leu Val Thr Leu Leu Arg Thr Leu Pro Met Phe His Asp Lys
                35                  40                  45

Glu Phe Ala Gln Ala Gln Gly Leu Pro Asp His Ala Leu Ala Leu Pro
50                  55                  60

Pro Ala Ser His Gly Pro Arg Val Leu Tyr Thr Val Leu Glu Cys Gln
65                  70                  75                  80

Pro Leu Leu Asp Ser Ser Asp Met Thr Ile Asp Asp Trp Ile Arg Ile
                85                  90                  95

Ala Lys Ile Ile Glu Arg His Tyr Glu Gln Tyr Gln Gly Phe Val Val
                100                 105                 110

Ile His Gly Thr Asp Thr Met Ala Ser Gly Ala Ser Met Leu Ser Phe
                115                 120                 125

Met Leu Glu Asn Leu His Lys Pro Val Ile Leu Thr Gly Ala Gln Val
            130                 135                 140

Pro Ile Arg Val Leu Trp Asn Asp Ala Arg Glu Asn Leu Leu Gly Ala
145                 150                 155                 160

Leu Leu Val Ala Gly Gln Tyr Ile Ile Pro Glu Val Cys Leu Phe Met
                165                 170                 175

Asn Ser Gln Leu Phe Arg Gly Asn Arg Val Thr Lys Val Asp Ser Gln
                180                 185                 190

Lys Phe Glu Ala Phe Cys Ser Pro Asn Leu Ser Pro Leu Ala Thr Val
                195                 200                 205

Gly Ala Asp Val Thr Ile Ala Trp Asp Leu Val Arg Lys Val Lys Trp
                210                 215                 220

Lys Asp Pro Leu Val Val His Ser Asn Met Glu His Asp Val Ala Leu
225                 230                 235                 240

Leu Arg Leu Tyr Pro Gly Ile Pro Ala Ser Leu Val Arg Ala Phe Leu
                245                 250                 255

Gln Pro Pro Leu Lys Gly Val Val Leu Glu Thr Phe Gly Ser Gly Asn
                260                 265                 270

Gly Pro Ser Lys Pro Asp Leu Leu Gln Glu Leu Arg Ala Ala Gln
                275                 280                 285
```

```
Arg Gly Leu Ile Met Val Asn Cys Ser Gln Cys Leu Arg Gly Ser Val
        290                 295                 300
Thr Pro Gly Tyr Ala Thr Ser Leu Ala Gly Ala Asn Ile Val Ser Gly
305                 310                 315                 320
Leu Asp Met Thr Ser Glu Ala Ala Leu Ala Lys Leu Ser Tyr Val Leu
                325                 330                 335
Gly Leu Pro Glu Leu Ser Leu Glu Arg Arg Gln Glu Leu Leu Ala Lys
            340                 345                 350
Asp Leu Arg Gly Glu Met Thr Leu Pro Thr Ala Asp Leu His Gln Ser
        355                 360                 365
Ser Pro Pro Gly Ser Thr Leu Gly Gln Gly Val Ala Arg Leu Phe Ser
370                 375                 380
Leu Phe Gly Cys Gln Glu Glu Asp Ser Val Gln Asp Ala Val Met Pro
385                 390                 395                 400
Ser Leu Ala Leu Ala Leu Ala His Ala Gly Glu Leu Glu Ala Leu Gln
                405                 410                 415
Ala Leu Met Glu Leu Gly Ser Asp Leu Arg Leu Lys Asp Ser Asn Gly
            420                 425                 430
Gln Thr Leu Leu His Val Ala Ala Arg Asn Gly Arg Asp Gly Val Val
        435                 440                 445
Thr Met Leu Leu His Arg Gly Met Asp Val Asn Ala Arg Asp Arg Asp
450                 455                 460
Gly Leu Ser Pro Leu Leu Ala Val Gln Gly Arg His Arg Glu Cys
465                 470                 475                 480
Ile Arg Leu Leu Arg Lys Ala Gly Ala Cys Leu Ser Pro Gln Asp Leu
                485                 490                 495
Lys Asp Ala Gly Thr Glu Leu Cys Arg Leu Ala Ser Arg Ala Asp Met
            500                 505                 510
Glu Gly Leu Gln Ala Trp Gly Gln Ala Gly Ala Asp Leu Gln Gln Pro
        515                 520                 525
Gly Tyr Asp Gly Arg Ser Ala Leu Cys Val Ala Glu Ala Ala Gly Asn
530                 535                 540
Gln Glu Val Leu Ala Leu Leu Arg Asn Leu Ala Leu Val Gly Pro Glu
545                 550                 555                 560
Val Pro Pro Ala Ile
                565

<210> SEQ ID NO 2
<211> LENGTH: 573
<212> TYPE: PRT
<213> ORGANISM: Homo sapiens

<400> SEQUENCE: 2

Met Ala Arg Ala Val Gly Pro Glu Arg Arg Leu Leu Ala Val Tyr Thr
1               5                   10                  15
Gly Gly Thr Ile Gly Met Arg Ser Glu Leu Gly Val Leu Val Pro Gly
            20                  25                  30
Thr Gly Leu Ala Ala Ile Leu Arg Thr Leu Pro Met Phe His Asp Glu
        35                  40                  45
Glu His Ala Arg Ala Arg Gly Leu Ser Glu Asp Thr Leu Val Leu Pro
    50                  55                  60
Pro Ala Ser Arg Asn Gln Arg Ile Leu Tyr Thr Val Leu Glu Cys Gln
65                  70                  75                  80
Pro Leu Phe Asp Ser Ser Asp Met Thr Ile Ala Glu Trp Val Cys Leu
                85                  90                  95
```

Ala Gln Thr Ile Lys Arg His Tyr Glu Gln Tyr His Gly Phe Val Val
                100                 105                 110

Ile His Gly Thr Asp Thr Met Ala Phe Ala Ala Ser Met Leu Ser Phe
            115                 120                 125

Met Leu Glu Asn Leu Gln Lys Thr Val Ile Leu Thr Gly Ala Gln Val
        130                 135                 140

Pro Ile His Ala Leu Trp Ser Asp Gly Arg Glu Asn Leu Leu Gly Ala
145                 150                 155                 160

Leu Leu Met Ala Gly Gln Tyr Val Ile Pro Glu Val Cys Leu Phe Phe
                165                 170                 175

Gln Asn Gln Leu Phe Arg Gly Asn Arg Ala Thr Lys Val Asp Ala Arg
            180                 185                 190

Arg Phe Ala Ala Phe Cys Ser Pro Asn Leu Leu Pro Leu Ala Thr Val
        195                 200                 205

Gly Ala Asp Ile Thr Ile Asn Arg Glu Leu Val Arg Lys Val Asp Gly
210                 215                 220

Lys Ala Gly Leu Val Val His Ser Ser Met Glu Gln Asp Val Gly Leu
225                 230                 235                 240

Leu Arg Leu Tyr Pro Gly Ile Pro Ala Ala Leu Val Arg Ala Phe Leu
                245                 250                 255

Gln Pro Pro Leu Lys Gly Val Val Met Glu Thr Phe Gly Ser Gly Asn
            260                 265                 270

Gly Pro Thr Lys Pro Asp Leu Leu Gln Glu Leu Arg Val Ala Thr Glu
        275                 280                 285

Arg Gly Leu Val Ile Val Asn Cys Thr His Cys Leu Gln Gly Ala Val
290                 295                 300

Thr Thr Asp Tyr Ala Ala Gly Met Ala Met Ala Gly Ala Gly Val Ile
305                 310                 315                 320

Ser Gly Phe Asp Met Thr Ser Glu Ala Ala Leu Ala Lys Leu Ser Tyr
                325                 330                 335

Val Leu Gly Gln Pro Gly Leu Ser Leu Asp Val Arg Lys Glu Leu Leu
            340                 345                 350

Thr Lys Asp Leu Arg Gly Glu Met Thr Pro Pro Ser Val Glu Glu Arg
        355                 360                 365

Arg Pro Ser Leu Gln Gly Asn Thr Leu Gly Gly Val Ser Trp Leu
370                 375                 380

Leu Ser Leu Ser Gly Ser Gln Glu Ala Asp Ala Leu Arg Asn Ala Leu
385                 390                 395                 400

Val Pro Ser Leu Ala Cys Ala Ala Ala His Ala Gly Asp Val Glu Ala
                405                 410                 415

Leu Gln Ala Leu Val Glu Leu Gly Ser Asp Leu Gly Leu Val Asp Phe
            420                 425                 430

Asn Gly Gln Thr Pro Leu His Ala Ala Arg Gly His Thr Glu
        435                 440                 445

Ala Val Thr Met Leu Leu Gln Arg Gly Val Asp Val Asn Thr Arg Asp
        450                 455                 460

Thr Asp Gly Phe Ser Pro Leu Leu Ala Val Arg Gly Arg His Pro
465                 470                 475                 480

Gly Val Ile Gly Leu Leu Arg Glu Ala Gly Ala Ser Leu Ser Thr Gln
                485                 490                 495

Glu Leu Glu Glu Ala Gly Thr Glu Leu Cys Arg Leu Ala Tyr Arg Ala
            500                 505                 510

Asp Leu Glu Gly Leu Gln Val Trp Gln Ala Gly Asp Leu Gly
            515                 520                 525

Gln Pro Gly Tyr Asp Gly His Ser Ala Leu His Val Ala Glu Ala Ala
    530                 535                 540

Gly Asn Leu Ala Val Val Ala Phe Leu Gln Ser Leu Glu Gly Ala Val
545                 550                 555                 560

Gly Ala Gln Ala Pro Cys Pro Glu Val Leu Pro Gly Val
                565                 570

<210> SEQ ID NO 3
<211> LENGTH: 359
<212> TYPE: PRT
<213> ORGANISM: Artificial Sequence
<220> FEATURE:
<223> OTHER INFORMATION: Synthetic polypeptide

<400> SEQUENCE: 3

Met Ala Arg Ala Ser Gly Ser Glu Arg His Leu Leu Ile Tyr Thr
1               5                   10                  15

Gly Gly Thr Leu Gly Met Gln Ser Lys Gly Gly Val Leu Val Pro Gly
                20                  25                  30

Pro Gly Leu Val Thr Leu Leu Arg Thr Leu Pro Met Phe His Asp Lys
            35                  40                  45

Glu Phe Ala Gln Ala Gln Gly Leu Pro Asp His Ala Leu Ala Leu Pro
    50                  55                  60

Pro Ala Ser His Gly Pro Arg Val Leu Tyr Thr Val Leu Glu Cys Gln
65                  70                  75                  80

Pro Leu Leu Asp Ser Ser Asp Met Thr Ile Asp Trp Ile Arg Ile
                85                  90                  95

Ala Lys Ile Ile Glu Arg His Tyr Glu Gln Tyr Gln Gly Phe Val Val
            100                 105                 110

Ile His Gly Thr Asp Thr Met Ala Ser Gly Ala Ser Met Leu Ser Phe
        115                 120                 125

Met Leu Glu Asn Leu His Lys Pro Val Ile Leu Thr Gly Ala Gln Val
130                 135                 140

Pro Ile Arg Val Leu Trp Asn Asp Ala Arg Glu Asn Leu Leu Gly Ala
145                 150                 155                 160

Leu Leu Val Ala Gly Gln Tyr Ile Ile Pro Glu Val Cys Leu Phe Met
                165                 170                 175

Asn Ser Gln Leu Phe Arg Gly Asn Arg Val Thr Lys Val Asp Ser Gln
            180                 185                 190

Lys Phe Glu Ala Phe Cys Ser Pro Asn Leu Ser Pro Leu Ala Thr Val
    195                 200                 205

Gly Ala Asp Val Thr Ile Ala Trp Asp Leu Val Arg Lys Val Lys Trp
210                 215                 220

Lys Asp Pro Leu Val Val His Ser Asn Met Glu His Asp Val Ala Leu
225                 230                 235                 240

Leu Arg Leu Tyr Pro Gly Ile Pro Ala Ser Leu Val Arg Ala Phe Leu
                245                 250                 255

Gln Pro Pro Leu Lys Gly Val Val Leu Glu Thr Phe Gly Ser Gly Asn
            260                 265                 270

Gly Pro Ser Lys Pro Asp Leu Leu Gln Glu Leu Arg Ala Ala Ala Gln
        275                 280                 285

Arg Gly Leu Ile Met Val Asn Cys Ser Gln Cys Leu Arg Gly Ser Val
    290                 295                 300

```
Thr Pro Gly Tyr Ala Thr Ser Leu Ala Gly Ala Asn Ile Val Ser Gly
305                 310                 315                 320

Leu Asp Met Thr Ser Glu Ala Ala Leu Ala Lys Leu Ser Tyr Val Leu
                325                 330                 335

Gly Leu Pro Glu Leu Ser Leu Glu Arg Arg Gln Glu Leu Leu Ala Lys
            340                 345                 350

Asp Leu Arg Gly Glu Met Thr
            355

<210> SEQ ID NO 4
<211> LENGTH: 367
<212> TYPE: PRT
<213> ORGANISM: Artificial Sequence
<220> FEATURE:
<223> OTHER INFORMATION: Synthetic polypeptide

<400> SEQUENCE: 4

Met Ala Arg Ala Ser Gly Ser Glu Arg His Leu Leu Ile Tyr Thr
1               5                   10                  15

Gly Gly Thr Leu Gly Met Gln Ser Lys Gly Val Leu Val Pro Gly
                20                  25                  30

Pro Gly Leu Val Thr Leu Leu Arg Thr Leu Pro Met Phe His Asp Lys
            35                  40                  45

Glu Phe Ala Gln Ala Gln Gly Leu Pro Asp His Ala Leu Ala Leu Pro
50                  55                  60

Pro Ala Ser His Gly Pro Arg Val Leu Tyr Thr Val Leu Glu Cys Gln
65                  70                  75                  80

Pro Leu Leu Asp Ser Ser Asp Met Thr Ile Asp Trp Ile Arg Ile
                85                  90                  95

Ala Lys Ile Ile Glu Arg His Tyr Glu Gln Tyr Gln Gly Phe Val Val
            100                 105                 110

Ile His Gly Thr Asp Thr Met Ala Ser Gly Ala Ser Met Leu Ser Phe
        115                 120                 125

Met Leu Glu Asn Leu His Lys Pro Val Ile Leu Thr Gly Ala Gln Val
130                 135                 140

Pro Ile Arg Val Leu Trp Asn Asp Ala Arg Glu Asn Leu Leu Gly Ala
145                 150                 155                 160

Leu Leu Val Ala Gly Gln Tyr Ile Ile Pro Glu Val Cys Leu Phe Met
                165                 170                 175

Asn Ser Gln Leu Phe Arg Gly Asn Arg Val Thr Lys Val Asp Ser Gln
            180                 185                 190

Lys Phe Glu Ala Phe Cys Ser Pro Asn Leu Ser Pro Leu Ala Thr Val
        195                 200                 205

Gly Ala Asp Val Thr Ile Ala Trp Asp Leu Val Arg Lys Val Lys Trp
210                 215                 220

Lys Asp Pro Leu Val Val His Ser Asn Met Glu His Asp Val Ala Leu
225                 230                 235                 240

Leu Arg Leu Tyr Pro Gly Ile Pro Ala Ser Leu Val Arg Ala Phe Leu
                245                 250                 255

Gln Pro Pro Leu Lys Gly Val Val Leu Glu Thr Phe Gly Ser Gly Asn
            260                 265                 270

Gly Pro Ser Lys Pro Asp Leu Leu Gln Glu Leu Arg Ala Ala Ala Gln
        275                 280                 285

Arg Gly Leu Ile Met Val Asn Cys Ser Gln Cys Leu Arg Gly Ser Val
290                 295                 300
```

```
Thr Pro Gly Tyr Ala Thr Ser Leu Ala Gly Ala Asn Ile Val Ser Gly
305                 310                 315                 320

Leu Asp Met Thr Ser Glu Ala Ala Leu Ala Lys Leu Ser Tyr Val Leu
            325                 330                 335

Gly Leu Pro Glu Leu Ser Leu Glu Arg Arg Gln Glu Leu Leu Ala Lys
        340                 345                 350

Asp Leu Arg Gly Glu Met Thr Leu Pro Thr Ala Asp Leu His Gln
    355                 360                 365
```

<210> SEQ ID NO 5
<211> LENGTH: 369
<212> TYPE: PRT
<213> ORGANISM: Artificial Sequence
<220> FEATURE:
<223> OTHER INFORMATION: Synthetic polypeptide

<400> SEQUENCE: 5

```
Met Ala Arg Ala Ser Gly Ser Glu Arg His Leu Leu Ile Tyr Thr
1               5                   10                  15

Gly Gly Thr Leu Gly Met Gln Ser Lys Gly Gly Val Leu Val Pro Gly
            20                  25                  30

Pro Gly Leu Val Thr Leu Leu Arg Thr Leu Pro Met Phe His Asp Lys
        35                  40                  45

Glu Phe Ala Gln Ala Gln Gly Leu Pro Asp His Ala Leu Ala Leu Pro
    50                  55                  60

Pro Ala Ser His Gly Pro Arg Val Leu Tyr Thr Val Leu Glu Cys Gln
65                  70                  75                  80

Pro Leu Leu Asp Ser Ser Asp Met Thr Ile Asp Trp Ile Arg Ile
                85                  90                  95

Ala Lys Ile Ile Glu Arg His Tyr Glu Gln Tyr Gln Gly Phe Val Val
            100                 105                 110

Ile His Gly Thr Asp Thr Met Ala Ser Gly Ala Ser Met Leu Ser Phe
        115                 120                 125

Met Leu Glu Asn Leu His Lys Pro Val Ile Leu Thr Gly Ala Gln Val
130                 135                 140

Pro Ile Arg Val Leu Trp Asn Asp Ala Arg Glu Asn Leu Leu Gly Ala
145                 150                 155                 160

Leu Leu Val Ala Gly Gln Tyr Ile Ile Pro Glu Val Cys Leu Phe Met
                165                 170                 175

Asn Ser Gln Leu Phe Arg Gly Asn Arg Val Thr Lys Val Asp Ser Gln
            180                 185                 190

Lys Phe Glu Ala Phe Cys Ser Pro Asn Leu Ser Pro Leu Ala Thr Val
        195                 200                 205

Gly Ala Asp Val Thr Ile Ala Trp Asp Leu Val Arg Lys Val Lys Trp
    210                 215                 220

Lys Asp Pro Leu Val Val His Ser Asn Met Glu His Asp Val Ala Leu
225                 230                 235                 240

Leu Arg Leu Tyr Pro Gly Ile Pro Ala Ser Leu Val Arg Ala Phe Leu
                245                 250                 255

Gln Pro Pro Leu Lys Gly Val Val Leu Glu Thr Phe Gly Ser Gly Asn
            260                 265                 270

Gly Pro Ser Lys Pro Asp Leu Leu Gln Glu Leu Arg Ala Ala Ala Gln
        275                 280                 285

Arg Gly Leu Ile Met Val Asn Cys Ser Gln Cys Leu Arg Gly Ser Val
    290                 295                 300
```

```
Thr Pro Gly Tyr Ala Thr Ser Leu Ala Gly Ala Asn Ile Val Ser Gly
305                 310                 315                 320

Leu Asp Met Thr Ser Glu Ala Ala Leu Ala Lys Leu Ser Tyr Val Leu
            325                 330                 335

Gly Leu Pro Glu Leu Ser Leu Glu Arg Arg Gln Glu Leu Leu Ala Lys
            340                 345                 350

Asp Leu Arg Gly Glu Met Thr Leu Pro Thr Ala Asp Leu His Gln Ser
            355                 360                 365

Ser

<210> SEQ ID NO 6
<211> LENGTH: 374
<212> TYPE: PRT
<213> ORGANISM: Artificial Sequence
<220> FEATURE:
<223> OTHER INFORMATION: Synthetic polypeptide

<400> SEQUENCE: 6

Met Ala Arg Ala Ser Gly Ser Glu Arg His Leu Leu Leu Ile Tyr Thr
1               5                   10                  15

Gly Gly Thr Leu Gly Met Gln Ser Lys Gly Gly Val Leu Val Pro Gly
            20                  25                  30

Pro Gly Leu Val Thr Leu Leu Arg Thr Leu Pro Met Phe His Asp Lys
            35                  40                  45

Glu Phe Ala Gln Ala Gln Gly Leu Pro Asp His Ala Leu Ala Leu Pro
        50                  55                  60

Pro Ala Ser His Gly Pro Arg Val Leu Tyr Thr Val Leu Glu Cys Gln
65                  70                  75                  80

Pro Leu Leu Asp Ser Ser Asp Met Thr Ile Asp Asp Trp Ile Arg Ile
                85                  90                  95

Ala Lys Ile Ile Glu Arg His Tyr Glu Gln Tyr Gln Gly Phe Val Val
            100                 105                 110

Ile His Gly Thr Asp Thr Met Ala Ser Gly Ala Ser Met Leu Ser Phe
        115                 120                 125

Met Leu Glu Asn Leu His Lys Pro Val Ile Leu Thr Gly Ala Gln Val
130                 135                 140

Pro Ile Arg Val Leu Trp Asn Asp Ala Arg Glu Asn Leu Leu Gly Ala
145                 150                 155                 160

Leu Leu Val Ala Gly Gln Tyr Ile Ile Pro Glu Val Cys Leu Phe Met
                165                 170                 175

Asn Ser Gln Leu Phe Arg Gly Asn Arg Val Thr Lys Val Asp Ser Gln
            180                 185                 190

Lys Phe Glu Ala Phe Cys Ser Pro Asn Leu Ser Pro Leu Ala Thr Val
        195                 200                 205

Gly Ala Asp Val Thr Ile Ala Trp Asp Leu Val Arg Lys Val Lys Trp
    210                 215                 220

Lys Asp Pro Leu Val Val His Ser Asn Met Glu His Asp Val Ala Leu
225                 230                 235                 240

Leu Arg Leu Tyr Pro Gly Ile Pro Ala Ser Leu Val Arg Ala Phe Leu
                245                 250                 255

Gln Pro Pro Leu Lys Gly Val Val Leu Glu Thr Phe Gly Ser Gly Asn
            260                 265                 270

Gly Pro Ser Lys Pro Asp Leu Leu Gln Glu Leu Arg Ala Ala Ala Gln
        275                 280                 285

Arg Gly Leu Ile Met Val Asn Cys Ser Gln Cys Leu Arg Gly Ser Val
```

```
            290                 295                 300
Thr Pro Gly Tyr Ala Thr Ser Leu Ala Gly Ala Asn Ile Val Ser Gly
305                 310                 315                 320

Leu Asp Met Thr Ser Glu Ala Ala Leu Ala Lys Leu Ser Tyr Val Leu
                325                 330                 335

Gly Leu Pro Glu Leu Ser Leu Glu Arg Arg Gln Glu Leu Leu Ala Lys
            340                 345                 350

Asp Leu Arg Gly Glu Met Thr Leu Pro Thr Ala Asp Leu His Gln Ser
        355                 360                 365

Ser Pro Pro Gly Ser Thr
    370

<210> SEQ ID NO 7
<211> LENGTH: 384
<212> TYPE: PRT
<213> ORGANISM: Artificial Sequence
<220> FEATURE:
<223> OTHER INFORMATION: Synthetic polypeptide

<400> SEQUENCE: 7

Met Ala Arg Ala Ser Gly Ser Glu Arg His Leu Leu Leu Ile Tyr Thr
1               5                   10                  15

Gly Gly Thr Leu Gly Met Gln Ser Lys Gly Gly Val Leu Val Pro Gly
            20                  25                  30

Pro Gly Leu Val Thr Leu Leu Arg Thr Leu Pro Met Phe His Asp Lys
        35                  40                  45

Glu Phe Ala Gln Ala Gln Gly Leu Pro Asp His Ala Leu Ala Leu Pro
    50                  55                  60

Pro Ala Ser His Gly Pro Arg Val Leu Tyr Thr Val Leu Glu Cys Gln
65                  70                  75                  80

Pro Leu Leu Asp Ser Ser Asp Met Thr Ile Asp Asp Trp Ile Arg Ile
                85                  90                  95

Ala Lys Ile Ile Glu Arg His Tyr Glu Gln Tyr Gln Gly Phe Val Val
            100                 105                 110

Ile His Gly Thr Asp Thr Met Ala Ser Gly Ala Ser Met Leu Ser Phe
        115                 120                 125

Met Leu Glu Asn Leu His Lys Pro Val Ile Leu Thr Gly Ala Gln Val
130                 135                 140

Pro Ile Arg Val Leu Trp Asn Asp Ala Arg Glu Asn Leu Leu Gly Ala
145                 150                 155                 160

Leu Leu Val Ala Gly Gln Tyr Ile Ile Pro Glu Val Cys Leu Phe Met
                165                 170                 175

Asn Ser Gln Leu Phe Arg Gly Asn Arg Val Thr Lys Val Asp Ser Gln
            180                 185                 190

Lys Phe Glu Ala Phe Cys Ser Pro Asn Leu Ser Pro Leu Ala Thr Val
        195                 200                 205

Gly Ala Asp Val Thr Ile Ala Trp Asp Leu Val Arg Lys Val Lys Trp
    210                 215                 220

Lys Asp Pro Leu Val Val His Ser Asn Met Glu His Asp Val Ala Leu
225                 230                 235                 240

Leu Arg Leu Tyr Pro Gly Ile Pro Ala Ser Leu Val Arg Ala Phe Leu
                245                 250                 255

Gln Pro Pro Leu Lys Gly Val Val Leu Glu Thr Phe Gly Ser Gly Asn
            260                 265                 270

Gly Pro Ser Lys Pro Asp Leu Leu Gln Glu Leu Arg Ala Ala Ala Gln
```

```
            275                 280                 285
Arg Gly Leu Ile Met Val Asn Cys Ser Gln Cys Leu Arg Gly Ser Val
    290                 295                 300

Thr Pro Gly Tyr Ala Thr Ser Leu Ala Gly Ala Asn Ile Val Ser Gly
305                 310                 315                 320

Leu Asp Met Thr Ser Glu Ala Ala Leu Ala Lys Leu Ser Tyr Val Leu
                325                 330                 335

Gly Leu Pro Glu Leu Ser Leu Glu Arg Arg Gln Glu Leu Leu Ala Lys
            340                 345                 350

Asp Leu Arg Gly Glu Met Thr Leu Pro Thr Ala Asp Leu His Gln Ser
        355                 360                 365

Ser Pro Pro Gly Ser Thr Leu Gly Gln Gly Val Ala Arg Leu Phe Ser
    370                 375                 380

<210> SEQ ID NO 8
<211> LENGTH: 392
<212> TYPE: PRT
<213> ORGANISM: Artificial Sequence
<220> FEATURE:
<223> OTHER INFORMATION: Synthetic polypeptide

<400> SEQUENCE: 8

Met Ala Arg Ala Ser Gly Ser Glu Arg His Leu Leu Leu Ile Tyr Thr
1               5                   10                  15

Gly Gly Thr Leu Gly Met Gln Ser Lys Gly Gly Val Leu Val Pro Gly
            20                  25                  30

Pro Gly Leu Val Thr Leu Leu Arg Thr Leu Pro Met Phe His Asp Lys
        35                  40                  45

Glu Phe Ala Gln Ala Gln Gly Leu Pro Asp His Ala Leu Ala Leu Pro
    50                  55                  60

Pro Ala Ser His Gly Pro Arg Val Leu Tyr Thr Val Leu Glu Cys Gln
65                  70                  75                  80

Pro Leu Leu Asp Ser Ser Asp Met Thr Ile Asp Trp Ile Arg Ile
                85                  90                  95

Ala Lys Ile Ile Glu Arg His Tyr Glu Gln Tyr Gln Gly Phe Val Val
            100                 105                 110

Ile His Gly Thr Asp Thr Met Ala Ser Gly Ala Ser Met Leu Ser Phe
        115                 120                 125

Met Leu Glu Asn Leu His Lys Pro Val Ile Leu Thr Gly Ala Gln Val
    130                 135                 140

Pro Ile Arg Val Leu Trp Asn Asp Ala Arg Glu Asn Leu Leu Gly Ala
145                 150                 155                 160

Leu Leu Val Ala Gly Gln Tyr Ile Ile Pro Glu Val Cys Leu Phe Met
                165                 170                 175

Asn Ser Gln Leu Phe Arg Gly Asn Arg Val Thr Lys Val Asp Ser Gln
            180                 185                 190

Lys Phe Glu Ala Phe Cys Ser Pro Asn Leu Ser Pro Leu Ala Thr Val
        195                 200                 205

Gly Ala Asp Val Thr Ile Ala Trp Asp Leu Val Arg Lys Val Lys Trp
    210                 215                 220

Lys Asp Pro Leu Val Val His Ser Asn Met Glu His Asp Val Ala Leu
225                 230                 235                 240

Leu Arg Leu Tyr Pro Gly Ile Pro Ala Ser Leu Val Arg Ala Phe Leu
                245                 250                 255

Gln Pro Pro Leu Lys Gly Val Val Leu Glu Thr Phe Gly Ser Gly Asn
```

```
                    260                 265                 270
Gly Pro Ser Lys Pro Asp Leu Leu Gln Glu Leu Arg Ala Ala Gln
            275                 280                 285

Arg Gly Leu Ile Met Val Asn Cys Ser Gln Cys Leu Arg Gly Ser Val
        290                 295                 300

Thr Pro Gly Tyr Ala Thr Ser Leu Ala Gly Ala Asn Ile Val Ser Gly
305                 310                 315                 320

Leu Asp Met Thr Ser Glu Ala Ala Leu Ala Lys Leu Ser Tyr Val Leu
                325                 330                 335

Gly Leu Pro Glu Leu Ser Leu Glu Arg Arg Gln Glu Leu Leu Ala Lys
            340                 345                 350

Asp Leu Arg Gly Glu Met Thr Leu Pro Thr Ala Asp Leu His Gln Ser
        355                 360                 365

Ser Pro Pro Gly Ser Thr Leu Gly Gln Gly Val Ala Arg Leu Phe Ser
    370                 375                 380

Leu Phe Gly Cys Gln Glu Glu Asp
385                 390

<210> SEQ ID NO 9
<211> LENGTH: 396
<212> TYPE: PRT
<213> ORGANISM: Artificial Sequence
<220> FEATURE:
<223> OTHER INFORMATION: Synthetic polypeptide

<400> SEQUENCE: 9

Met Ala Arg Ala Ser Gly Ser Glu Arg His Leu Leu Leu Ile Tyr Thr
1               5                   10                  15

Gly Gly Thr Leu Gly Met Gln Ser Lys Gly Gly Val Leu Val Pro Gly
            20                  25                  30

Pro Gly Leu Val Thr Leu Leu Arg Thr Leu Pro Met Phe His Asp Lys
        35                  40                  45

Glu Phe Ala Gln Ala Gln Gly Leu Pro Asp His Ala Leu Ala Leu Pro
    50                  55                  60

Pro Ala Ser His Gly Pro Arg Val Leu Tyr Thr Val Leu Glu Cys Gln
65                  70                  75                  80

Pro Leu Leu Asp Ser Ser Asp Met Thr Ile Asp Asp Trp Ile Arg Ile
                85                  90                  95

Ala Lys Ile Ile Glu Arg His Tyr Glu Gln Tyr Gln Gly Phe Val Val
            100                 105                 110

Ile His Gly Thr Asp Thr Met Ala Ser Gly Ala Ser Met Leu Ser Phe
        115                 120                 125

Met Leu Glu Asn Leu His Lys Pro Val Ile Leu Thr Gly Ala Gln Val
    130                 135                 140

Pro Ile Arg Val Leu Trp Asn Asp Ala Arg Glu Asn Leu Leu Gly Ala
145                 150                 155                 160

Leu Leu Val Ala Gly Gln Tyr Ile Ile Pro Glu Val Cys Leu Phe Met
                165                 170                 175

Asn Ser Gln Leu Phe Arg Gly Asn Arg Val Thr Lys Val Asp Ser Gln
            180                 185                 190

Lys Phe Glu Ala Phe Cys Ser Pro Asn Leu Ser Pro Leu Ala Thr Val
        195                 200                 205

Gly Ala Asp Val Thr Ile Ala Trp Asp Leu Val Arg Lys Val Lys Trp
    210                 215                 220

Lys Asp Pro Leu Val Val His Ser Asn Met Glu His Asp Val Ala Leu
```

```
            225                 230                 235                 240

Leu Arg Leu Tyr Pro Gly Ile Pro Ala Ser Leu Val Arg Ala Phe Leu
                245                 250                 255

Gln Pro Pro Leu Lys Gly Val Val Leu Glu Thr Phe Gly Ser Gly Asn
            260                 265                 270

Gly Pro Ser Lys Pro Asp Leu Gln Glu Leu Arg Ala Ala Gln
        275                 280                 285

Arg Gly Leu Ile Met Val Asn Cys Ser Gln Cys Leu Arg Gly Ser Val
    290                 295                 300

Thr Pro Gly Tyr Ala Thr Ser Leu Ala Gly Ala Asn Ile Val Ser Gly
305                 310                 315                 320

Leu Asp Met Thr Ser Glu Ala Ala Leu Ala Lys Leu Ser Tyr Val Leu
                325                 330                 335

Gly Leu Pro Glu Leu Ser Leu Glu Arg Arg Gln Glu Leu Leu Ala Lys
            340                 345                 350

Asp Leu Arg Gly Glu Met Thr Leu Pro Thr Ala Asp Leu His Gln Ser
        355                 360                 365

Ser Pro Pro Gly Ser Thr Leu Gly Gln Gly Val Ala Arg Leu Phe Ser
    370                 375                 380

Leu Phe Gly Cys Gln Glu Glu Asp Ser Val Gln Asp
385                 390                 395

<210> SEQ ID NO 10
<211> LENGTH: 33
<212> TYPE: DNA
<213> ORGANISM: Artificial Sequence
<220> FEATURE:
<223> OTHER INFORMATION: Synthetic oligonucleotide

<400> SEQUENCE: 10
aacgtcggat ccttaaatag ccggcgggac ttc                                33

<210> SEQ ID NO 11
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 11
atggcacgcg cttcgggctc ggaa                                          24

<210> SEQ ID NO 12
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 12
ccagattacg cagcagagc                                                19

<210> SEQ ID NO 13
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 13
gctcgtgctg tgggtccgga a                                             21
```

<210> SEQ ID NO 14
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 14
gacacccggc agcacttc                                                 18

<210> SEQ ID NO 15
<211> LENGTH: 44
<212> TYPE: DNA
<213> ORGANISM: Artificial Sequence
<220> FEATURE:
<223> OTHER INFORMATION: Synthetic oligonucleotide

<400> SEQUENCE: 15
ctgatgcagg tctgccgtcg gcagcgtcat ttcaccgcgc aggt                     44

<210> SEQ ID NO 16
<211> LENGTH: 43
<212> TYPE: DNA
<213> ORGANISM: Artificial Sequence
<220> FEATURE:
<223> OTHER INFORMATION: Synthetic oligonucleotide

<400> SEQUENCE: 16
aaggacctgc gcggtgaaat gacgctgccg acggcagacc tgc                      43

<210> SEQ ID NO 17
<211> LENGTH: 45
<212> TYPE: DNA
<213> ORGANISM: Artificial Sequence
<220> FEATURE:
<223> OTHER INFORMATION: Synthetic oligonucleotide

<400> SEQUENCE: 17
gcgacgttct tccacagacg gcggggtcat ttcaccacgc agatc                    45

<210> SEQ ID NO 18
<211> LENGTH: 44
<212> TYPE: DNA
<213> ORGANISM: Artificial Sequence
<220> FEATURE:
<223> OTHER INFORMATION: Synthetic oligonucleotide

<400> SEQUENCE: 18
aaagatctgc gtggtgaaat gaccccgccg tctgtggaag aacg                     44

<210> SEQ ID NO 19
<211> LENGTH: 48
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (22)..(23)
<223> OTHER INFORMATION: n is a, c, g, or t
<220> FEATURE:
<221> NAME/KEY: misc_feature
<222> LOCATION: (25)..(26)
<223> OTHER INFORMATION: n is a, c, g, or t

<400> SEQUENCE: 19
tacaccggcg gcaccattgg cnnknnkagt gagctcggcg tgcttgtg          48

<210> SEQ ID NO 20
<211> LENGTH: 48
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (23)..(24)
<223> OTHER INFORMATION: n is a, c, g, or t
<220> FEATURE:
<221> NAME/KEY: misc_feature
<222> LOCATION: (26)..(27)
<223> OTHER INFORMATION: n is a, c, g, or t

<400> SEQUENCE: 20
cacaagcacg ccgagctcac tmnnmnngcc aatggtgccg ccggtgta          48

<210> SEQ ID NO 21
<211> LENGTH: 51
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (22)..(23)
<223> OTHER INFORMATION: n is a, c, g, or t
<220> FEATURE:
<221> NAME/KEY: misc_feature
<222> LOCATION: (28)..(29)
<223> OTHER INFORMATION: n is a, c, g, or t

<400> SEQUENCE: 21
ctggagtgcc agcccctctt cnnktccnnk gacatgacca tcgctgagtg g          51

<210> SEQ ID NO 22
<211> LENGTH: 51
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (23)..(24)
<223> OTHER INFORMATION: n is a, c, g, or t
<220> FEATURE:
<221> NAME/KEY: misc_feature
<222> LOCATION: (29)..(30)
<223> OTHER INFORMATION: n is a, c, g, or t

<400> SEQUENCE: 22
ccactcagcg atggtcatgt cmnnggamnn gaagaggggc tggcactcca g          51

<210> SEQ ID NO 23
<211> LENGTH: 54
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (25)..(26)
<223> OTHER INFORMATION: n is a, c, g, or t
<220> FEATURE:
<221> NAME/KEY: misc_feature
<222> LOCATION: (28)..(29)
<223> OTHER INFORMATION: n is a, c, g, or t

<400> SEQUENCE: 23

```
cagtaccacg gctttgtggt catcnnknnk accgacacca tggcctttgc tgcc         54
```

<210> SEQ ID NO 24
<211> LENGTH: 54
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (26)..(27)
<223> OTHER INFORMATION: n is a, c, g, or t
<220> FEATURE:
<221> NAME/KEY: misc_feature
<222> LOCATION: (29)..(30)
<223> OTHER INFORMATION: n is a, c, g, or t

<400> SEQUENCE: 24

```
ggcagcaaag gccatggtgt cggtmnnmnn gatgaccaca aagccgtggt actg         54
```

<210> SEQ ID NO 25
<211> LENGTH: 53
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (24)..(25)
<223> OTHER INFORMATION: n is a, c, g, or t
<220> FEATURE:
<221> NAME/KEY: misc_feature
<222> LOCATION: (27)..(28)
<223> OTHER INFORMATION: n is a, c, g, or t
<220> FEATURE:
<221> NAME/KEY: misc_feature
<222> LOCATION: (30)..(31)
<223> OTHER INFORMATION: n is a, c, g, or t

<400> SEQUENCE: 25

```
agaagactgt catcctcact gggnnknnkn nkcccatcca tgccctgtgg agc          53
```

<210> SEQ ID NO 26
<211> LENGTH: 52
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (22)..(23)
<223> OTHER INFORMATION: n is a, c, g, or t
<220> FEATURE:
<221> NAME/KEY: misc_feature
<222> LOCATION: (25)..(26)
<223> OTHER INFORMATION: n is a, c, g, or t
<220> FEATURE:
<221> NAME/KEY: misc_feature
<222> LOCATION: (28)..(29)
<223> OTHER INFORMATION: n is a, c, g, or t

<400> SEQUENCE: 26

```
gctccacagg gcatgatggg mnnmnnmnnc ccagtgagga tgacagtctt ct           52
```

<210> SEQ ID NO 27
<211> LENGTH: 52
<212> TYPE: DNA
<213> ORGANISM: Artificial Sequence
<220> FEATURE:
<223> OTHER INFORMATION: Synthetic oligonucleotide
<220> FEATURE:

<220> FEATURE:
<221> NAME/KEY: misc_feature
<222> LOCATION: (24)..(25)
<223> OTHER INFORMATION: n is a, c, g, or t
<220> FEATURE:
<221> NAME/KEY: misc_feature
<222> LOCATION: (27)..(28)
<223> OTHER INFORMATION: n is a, c, g, or t

<400> SEQUENCE: 27
gcaaccgggc aaccaaggta gacnnknnka ggttcgcagc tttctgctcc cc        52

<210> SEQ ID NO 28
<211> LENGTH: 52
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (25)..(26)
<223> OTHER INFORMATION: n is a, c, g, or t
<220> FEATURE:
<221> NAME/KEY: misc_feature
<222> LOCATION: (28)..(29)
<223> OTHER INFORMATION: n is a, c, g, or t

<400> SEQUENCE: 28
ggggagcaga aagctgcgaa cctmnnmnng tctaccttgg ttgcccggtt gc        52

<210> SEQ ID NO 29
<211> LENGTH: 47
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (18)..(19)
<223> OTHER INFORMATION: n is a, c, g, or t
<220> FEATURE:
<221> NAME/KEY: misc_feature
<222> LOCATION: (27)..(28)
<223> OTHER INFORMATION: n is a, c, g, or t

<400> SEQUENCE: 29
tcatccacgg caccgacnnk atggccnnkg ctgcctcgat gctgtcc              47

<210> SEQ ID NO 30
<211> LENGTH: 47
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (20)..(21)
<223> OTHER INFORMATION: n is a, c, g, or t
<220> FEATURE:
<221> NAME/KEY: misc_feature
<222> LOCATION: (29)..(30)
<223> OTHER INFORMATION: n is a, c, g, or t

<400> SEQUENCE: 30
ggacagcatc gaggcagcmn nggccatmnn gtcggtgccg tggatga              47

<210> SEQ ID NO 31
<211> LENGTH: 63
<212> TYPE: DNA
<213> ORGANISM: Artificial Sequence
<220> FEATURE:
<223> OTHER INFORMATION: Synthetic oligonucleotide

```
<220> FEATURE:
<221> NAME/KEY: misc_feature
<222> LOCATION: (19)..(20)
<223> OTHER INFORMATION: n is a, c, g, or t
<220> FEATURE:
<221> NAME/KEY: misc_feature
<222> LOCATION: (31)..(32)
<223> OTHER INFORMATION: n is a, c, g, or t
<220> FEATURE:
<221> NAME/KEY: misc_feature
<222> LOCATION: (43)..(44)
<223> OTHER INFORMATION: n is a, c, g, or t

<400> SEQUENCE: 31
tccagtgaca tgaccatcnn kgagtgggtt nnkcttgccc agnnkatcaa gaggcactac      60
gag                                                                   63

<210> SEQ ID NO 32
<211> LENGTH: 63
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (20)..(21)
<223> OTHER INFORMATION: n is a, c, g, or t
<220> FEATURE:
<221> NAME/KEY: misc_feature
<222> LOCATION: (32)..(33)
<223> OTHER INFORMATION: n is a, c, g, or t
<220> FEATURE:
<221> NAME/KEY: misc_feature
<222> LOCATION: (44)..(45)
<223> OTHER INFORMATION: n is a, c, g, or t

<400> SEQUENCE: 32
ctcgtagtgc ctcttgatmn nctgggcaag mnnaacccac tcmnngatgg tcatgtcact      60
gga                                                                   63

<210> SEQ ID NO 33
<211> LENGTH: 48
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (19)..(20)
<223> OTHER INFORMATION: n is a, c, g, or t
<220> FEATURE:
<221> NAME/KEY: misc_feature
<222> LOCATION: (25)..(26)
<223> OTHER INFORMATION: n is a, c, g, or t
<220> FEATURE:
<221> NAME/KEY: misc_feature
<222> LOCATION: (28)..(29)
<223> OTHER INFORMATION: n is a, c, g, or t

<400> SEQUENCE: 33
ggcggcacca ttggcatgnn kagtnnknnk ggcgtgcttg tgcccggg                   48

<210> SEQ ID NO 34
<211> LENGTH: 48
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (20)..(21)
```

```
<223> OTHER INFORMATION: n is a, c, g, or t
<220> FEATURE:
<221> NAME/KEY: misc_feature
<222> LOCATION: (23)..(24)
<223> OTHER INFORMATION: n is a, c, g, or t
<220> FEATURE:
<221> NAME/KEY: misc_feature
<222> LOCATION: (29)..(30)
<223> OTHER INFORMATION: n is a, c, g, or t

<400> SEQUENCE: 34
cccgggcaca agcacgccmn nmnnactmnn catgccaatg gtgccgcc              48

<210> SEQ ID NO 35
<211> LENGTH: 1722
<212> TYPE: DNA
<213> ORGANISM: Artificial Sequence
<220> FEATURE:
<223> OTHER INFORMATION: Synthetic polynucleotide

<400> SEQUENCE: 35
atggctcgtg ctgtgggtcc ggaacgccgc ctgctggctg tctatacggg tggtacgatt      60
ggtatgcgct ctgaactggg tgtcctggtg ccgggtaccg gtctggcagc aattctgcgt     120
acgctgccga tgtttcatga tgaagaacac gcacgtgcac gcggtctgtc ggaagacacc     180
ctggtgctgc cgccggcaag ccgtaaccag cgcatcctgt ataccgttct ggaatgccaa     240
ccgctgtttg atagctctga catgaccatt gccgaatggg tttgtctggc acagacgatc     300
aaacgtcatt atgaacaata ccacggtttc gtggttattc atggcaccga tacgatggcc     360
tttgcagctt ccatgctgtc attcatgctg gaaaacctgc agaagacgt tattctgacg      420 ggcgctcaag tcccgatcca cgcactgtgg agcgacggtc gcgaaaatct gctgggcgcc     480
ctgctgatgg caggccagta tgtcatcccg gaagtgtgcc tgttttcca gaaccaactg      540 ttccgtggta atcgcgctac caaagtcgat gcgcgtcgct ttgcggcctt ctgtagcccg     600
aacctgctgc cgctgctac cgttggtgca gatattacga tcaatcgtga actggtgcgc     660
aaagttgacg gcaaggcagg tctggtcgtg catagttcca tggaacagga tgtcggcctg     720
ctgcgtctgt acccgggtat tccggcagct ctggtgcgtg cctttctgca gccgccgctg     780
aaaggtgttg tcatggaaac cttcggttct ggcaacggtc cgacgaagcc ggatctgctg     840
caggaactgc gtgtggcaac cgaacgcggc ctggtcattg tgaattgcac gcactgtctg     900
caaggcgcag ttaccacgga ttatgcagcc ggtatggcaa tggctggtgc gggtgtcatc     960
tcgggttttg acatgaccag cgaagcagct ctggcgaaac tgtcctacgt tctgggccag    1020
ccgggtctgt cactggatgt ccgtaaagaa ctgctgacca aggacctgcg cggtgaaatg    1080
acgccgccgt ctgtggaaga cgtcgcccg agtctgcagg gtaacaccct gggcggtggc     1140
gtttcttggc tgctgtcact gtcggcagc caagaagccg atgcactgcg caatgcactg      1200
gtgccgagtc tggcatgcgc agcagcacat gcaggtgacg tggaagctct gcaggcgctg    1260
gttgaactgg gttccgatct gggcctggtg gactttaacg tcaaacccc gctgcatgct     1320 gcagcacgtg gtggccacac cgaagcagtt acgatgctgc tgcagcgtgg cgttgatgtc    1380 aataccgcg atacggacgg tttcagtccg ctgctgctgg cagtccgtgg tcgtcatccg     1440
ggcgtgatcg gtctgctgcg cgaagctggt gcgtctctga gtacccagga actggaagaa    1500
gcgggcacgg aactgtgtcg tctggcctat cgcgcagatc tggaaggcct gcaagtgtgg    1560
tggcaagcag gtgcagatct gggtcagccg ggttacgacg tcatagcgc cctgcacgtt     1620 gcagaagcag ctggtaatct ggctgtggtt gcgtttctgc aaagtctgga aggtgccgtc    1680
```

| | | |
|---|---|---|
| ggtgcccaag cgccgtgccc ggaagtgctg ccgggtgtct aa | | 1722 |

<210> SEQ ID NO 36
<211> LENGTH: 1698
<212> TYPE: DNA
<213> ORGANISM: Artificial Sequence
<220> FEATURE:
<223> OTHER INFORMATION: Synthetic polynucleotide

<400> SEQUENCE: 36

| | | |
|---|---|---|
| atggcacgcg cttcgggctc ggaacgtcat ctgctgctga tctacacggg tggcacgctg | | 60 |
| ggtatgcaat ccaagggtgg tgttctggtc ccgggtccgg tctggtgac cctgctgcgt | | 120 |
| acgctgccga tgtttcatga taaagaattc gcacaggcac aaggcctgcc ggaccatgct | | 180 |
| ctggcgctgc cgccgccctc tcacggtccg cgcgtgctgt ataccgttct ggaatgccag | | 240 |
| ccgctgctgg atagctctga catgacgatt gatgactgga ttcgtatcgc gaagattatc | | 300 |
| gaacgccatt atgaacagta ccaaggtttt gtggttatcc acggcaccga tacgatggct | | 360 |
| tcaggcgcgt cgatgctgag cttcatgctg gaaaacctgc acaaaccggt gattctgacc | | 420 |
| ggtgcccagg tcccgatccg tgtgctgtgg aacgatgcac gcgaaaatct gctgggtgcc | | 480 |
| ctgctggttg caggccagta tattatcccg gaagtctgcc tgtttatgaa ctcgcaactg | | 540 |
| ttccgtggca atcgcgtcac gaaggtggat agccagaaat ttgaagcatt ctgttctccg | | 600 |
| aacctgagtc cgctggctac cgttggtgcg gatgtcacga ttgcgtggga cctggttcgt | | 660 |
| aaagtcaagt ggaaagatcc gctggtcgtg cattccaata tggaacacga cgtcgcactg | | 720 |
| ctgcgtctgt acccgggcat cccggctagc ctggttcgtg cgtttctgca gccgccgctg | | 780 |
| aagggtgttg tcctggaaac cttcggctcc ggtaatggcc cgtcaaaacc ggatctgctg | | 840 |
| caggaactgc gtgcagcagc acaacgcggc ctgattatgg tgaactgctc gcagtgtctg | | 900 |
| cgcggtagcg ttaccccggg ttatgccacg agcctggcag gtgcaaatat cgtgtctggc | | 960 |
| ctggatatga ccagtgaagc tgcgctggcg aagctgtctt acgttctggg cctgccggaa | | 1020 |
| ctgagtctgg aacgtcgcca ggaactgctg gctaaagatc tgcgtggtga aatgaccctg | | 1080 |
| ccgacggcag acctgcatca gagttccccg ccgggctcca cctgggtca aggcgtggcc | | 1140 |
| cgcctgtttt cactgttcgg ttgtcaggaa gaagattcgg tgcaagacgc agttatgccg | | 1200 |
| agcctggctc tggcactggc acacgcaggt gaactggaag ccctgcaagc actgatggaa | | 1260 |
| ctgggttccg atctgcgtct gaaagactca aacggccaga ccctgctgca tgttgccgca | | 1320 |
| cgtaatggtc gcgatggcgt ggttacgatg ctgctgcacc gcggtatgga cgtgaacgca | | 1380 |
| cgtgatcgtg acggtctgtc accgctgctg ctggcagttc aaggtcgtca tcgcgaatgc | | 1440 |
| attcgtctgc tgcgcaaggc tggcgcgtgt ctgtctccgc aggatctgaa agacgcgggt | | 1500 |
| accgaactgt gccgtctggc tagtcgcgcg gatatggaag gtctgcaggc atgggtcaa | | 1560 |
| gcaggtgcag atctgcagca accgggttac gacggccgta gtgccctgtg tgtgcagaa | | 1620 |
| gctgcgggta atcaggaagt gctggctctg ctgcgtaatc tggctctggt tggcccggaa | | 1680 |
| gtcccgccgg ctatttaa | | 1698 |

<210> SEQ ID NO 37
<211> LENGTH: 571
<212> TYPE: PRT
<213> ORGANISM: Artificial Sequence
<220> FEATURE:
<223> OTHER INFORMATION: Synthetic polypeptide

<400> SEQUENCE: 37

Met Ala Arg Ala Ser Gly Ser Glu Arg His Leu Leu Ile Tyr Thr
1               5                   10                  15

Gly Gly Thr Leu Gly Met Gln Ser Lys Gly Val Leu Val Pro Gly
            20                  25                  30

Pro Gly Leu Val Thr Leu Leu Arg Thr Leu Pro Met Phe His Asp Lys
        35                  40                  45

Glu Phe Ala Gln Ala Gln Gly Leu Pro Asp His Ala Leu Ala Leu Pro
    50                  55                  60

Pro Ala Ser His Gly Pro Arg Val Leu Tyr Thr Val Leu Glu Cys Gln
65              70                  75                  80

Pro Leu Leu Asp Ser Ser Asp Met Thr Ile Asp Asp Trp Ile Arg Ile
                85                  90                  95

Ala Lys Ile Ile Glu Arg His Tyr Glu Gln Tyr Gln Gly Phe Val Val
                100                 105                 110

Ile His Gly Thr Asp Thr Met Ala Ser Gly Ala Ser Met Leu Ser Phe
            115                 120                 125

Met Leu Glu Asn Leu His Lys Pro Val Ile Leu Thr Gly Ala Gln Val
130                 135                 140

Pro Ile Arg Val Leu Trp Asn Asp Ala Arg Glu Asn Leu Leu Gly Ala
145                 150                 155                 160

Leu Leu Val Ala Gly Gln Tyr Ile Ile Pro Glu Val Cys Leu Phe Met
                165                 170                 175

Asn Ser Gln Leu Phe Arg Gly Asn Arg Val Thr Lys Val Asp Ser Gln
            180                 185                 190

Lys Phe Glu Ala Phe Cys Ser Pro Asn Leu Ser Pro Leu Ala Thr Val
        195                 200                 205

Gly Ala Asp Val Thr Ile Ala Trp Asp Leu Val Arg Lys Val Lys Trp
210                 215                 220

Lys Asp Pro Leu Val Val His Ser Ser Met Glu Gln Asp Val Gly Leu
225                 230                 235                 240

Leu Arg Leu Tyr Pro Gly Ile Pro Ala Ser Leu Val Arg Ala Phe Leu
                245                 250                 255

Gln Pro Pro Leu Lys Gly Val Val Leu Glu Thr Phe Gly Ser Gly Asn
            260                 265                 270

Gly Pro Ser Lys Pro Asp Leu Leu Gln Glu Leu Arg Ala Ala Glu
        275                 280                 285

Arg Gly Leu Ile Met Val Asn Cys Ser Gln Cys Leu Arg Gly Ser Val
290                 295                 300

Thr Pro Gly Tyr Ala Thr Ser Leu Ala Gly Ala Asn Ile Val Ser Gly
305                 310                 315                 320

Leu Asp Met Thr Ser Glu Ala Ala Leu Ala Lys Leu Ser Tyr Val Leu
                325                 330                 335

Gly Leu Pro Glu Leu Ser Leu Glu Arg Arg Gln Glu Leu Leu Ala Lys
            340                 345                 350

Asp Leu Arg Gly Glu Met Thr Pro Pro Ser Val Glu Glu Arg Arg Pro
        355                 360                 365

Ser Leu Gln Gly Asn Thr Leu Gly Gly Val Ser Trp Leu Leu Ser
        370                 375                 380

Leu Ser Gly Ser Gln Glu Ala Asp Ala Leu Arg Asn Ala Leu Val Pro
385                 390                 395                 400

Ser Leu Ala Cys Ala Ala Ala His Ala Gly Asp Val Glu Ala Leu Gln
                405                 410                 415

```
Ala Leu Val Glu Leu Gly Ser Asp Leu Gly Leu Val Asp Phe Asn Gly
            420                 425                 430

Gln Thr Pro Leu His Ala Ala Arg Gly Gly His Thr Glu Ala Val
            435                 440                 445

Thr Met Leu Leu Gln Arg Gly Val Asp Val Asn Thr Arg Asp Thr Asp
    450                 455                 460

Gly Phe Ser Pro Leu Leu Ala Val Arg Gly Arg His Pro Gly Val
465                 470                 475                 480

Ile Gly Leu Leu Arg Glu Ala Gly Ala Ser Leu Ser Thr Gln Glu Leu
            485                 490                 495

Glu Glu Ala Gly Thr Glu Leu Cys Arg Leu Ala Tyr Arg Ala Asp Leu
            500                 505                 510

Glu Gly Leu Gln Val Trp Trp Gln Ala Gly Ala Asp Leu Gly Gln Pro
            515                 520                 525

Gly Tyr Asp Gly His Ser Ala Leu His Val Ala Glu Ala Ala Gly Asn
            530                 535                 540

Leu Ala Val Val Ala Phe Leu Gln Ser Leu Glu Gly Ala Val Gly Ala
545                 550                 555                 560

Gln Ala Pro Cys Pro Glu Val Leu Pro Gly Val
            565                 570
```

<210> SEQ ID NO 38
<211> LENGTH: 567
<212> TYPE: PRT
<213> ORGANISM: Artificial Sequence
<220> FEATURE:
<223> OTHER INFORMATION: Synthetic polypeptide

<400> SEQUENCE: 38

```
Met Ala Arg Ala Val Gly Pro Glu Arg Arg Leu Leu Ala Val Tyr Thr
1               5                   10                  15

Gly Gly Thr Ile Gly Met Arg Ser Glu Leu Gly Val Leu Val Pro Gly
            20                  25                  30

Thr Gly Leu Ala Ala Ile Leu Arg Thr Leu Pro Met Phe His Asp Glu
        35                  40                  45

Glu His Ala Arg Ala Arg Gly Leu Ser Glu Asp Thr Leu Val Leu Pro
    50                  55                  60

Pro Ala Ser Arg Asn Gln Arg Ile Leu Tyr Thr Val Leu Glu Cys Gln
65                  70                  75                  80

Pro Leu Phe Asp Ser Ser Asp Met Thr Ile Ala Glu Trp Val Cys Leu
                85                  90                  95

Ala Gln Thr Ile Lys Arg His Tyr Glu Gln Tyr His Gly Phe Val Val
            100                 105                 110

Ile His Gly Thr Asp Thr Met Ala Phe Ala Ala Ser Met Leu Ser Phe
        115                 120                 125

Met Leu Glu Asn Leu Gln Lys Thr Val Ile Leu Thr Gly Ala Gln Val
    130                 135                 140

Pro Ile His Ala Leu Trp Ser Asp Gly Arg Glu Asn Leu Leu Gly Ala
145                 150                 155                 160

Leu Leu Met Ala Gly Gln Tyr Val Ile Pro Glu Val Cys Leu Phe Phe
                165                 170                 175

Gln Asn Gln Leu Phe Arg Gly Asn Arg Ala Thr Lys Val Asp Ala Arg
            180                 185                 190

Arg Phe Ala Ala Phe Cys Ser Pro Asn Leu Leu Pro Leu Ala Thr Val
        195                 200                 205
```

Gly Ala Asp Ile Thr Ile Asn Arg Glu Leu Val Arg Lys Val Asp Gly
            210                 215                 220

Lys Ala Gly Leu Val Val His Ser Ser Met Glu Gln Asp Val Gly Leu
225                 230                 235                 240

Leu Arg Leu Tyr Pro Gly Ile Pro Ala Ala Leu Val Arg Ala Phe Leu
                245                 250                 255

Gln Pro Pro Leu Lys Gly Val Val Met Glu Thr Phe Gly Ser Gly Asn
            260                 265                 270

Gly Pro Thr Lys Pro Asp Leu Leu Gln Glu Leu Arg Val Ala Thr Glu
        275                 280                 285

Arg Gly Leu Val Ile Val Asn Cys Thr His Cys Leu Gln Gly Ala Val
    290                 295                 300

Thr Thr Asp Tyr Ala Ala Gly Met Ala Met Ala Gly Ala Gly Val Ile
305                 310                 315                 320

Ser Gly Phe Asp Met Thr Ser Glu Ala Ala Leu Ala Lys Leu Ser Tyr
                325                 330                 335

Val Leu Gly Gln Pro Gly Leu Ser Leu Asp Val Arg Lys Glu Leu Leu
            340                 345                 350

Thr Lys Asp Leu Arg Gly Glu Met Thr Leu Pro Thr Ala Asp Leu His
        355                 360                 365

Gln Ser Ser Pro Pro Gly Ser Thr Leu Gly Gln Gly Val Ala Arg Leu
    370                 375                 380

Phe Ser Leu Phe Gly Cys Gln Glu Glu Asp Ser Val Gln Asp Ala Val
385                 390                 395                 400

Met Pro Ser Leu Ala Leu Ala Leu Ala His Ala Gly Glu Leu Glu Ala
                405                 410                 415

Leu Gln Ala Leu Met Glu Leu Gly Ser Asp Leu Arg Leu Lys Asp Ser
            420                 425                 430

Asn Gly Gln Thr Leu Leu His Val Ala Ala Arg Asn Gly Arg Asp Gly
        435                 440                 445

Val Val Thr Met Leu Leu His Arg Gly Met Asp Val Asn Ala Arg Asp
    450                 455                 460

Arg Asp Gly Leu Ser Pro Leu Leu Leu Ala Val Gln Gly Arg His Arg
465                 470                 475                 480

Glu Cys Ile Arg Leu Leu Arg Lys Ala Gly Ala Cys Leu Ser Pro Gln
                485                 490                 495

Asp Leu Lys Asp Ala Gly Thr Glu Leu Cys Arg Leu Ala Ser Arg Ala
            500                 505                 510

Asp Met Glu Gly Leu Gln Ala Trp Gly Gln Ala Gly Ala Asp Leu Gln
        515                 520                 525

Gln Pro Gly Tyr Asp Gly Arg Ser Ala Leu Cys Val Ala Glu Ala Ala
    530                 535                 540

Gly Asn Gln Glu Val Leu Ala Leu Leu Arg Asn Leu Ala Leu Val Gly
545                 550                 555                 560

Pro Glu Val Pro Pro Ala Ile
                565

<210> SEQ ID NO 39
<211> LENGTH: 571
<212> TYPE: PRT
<213> ORGANISM: Artificial Sequence
<220> FEATURE:
<223> OTHER INFORMATION: Synthetic polypeptide

<400> SEQUENCE: 39

-continued

```
Met Ala Arg Ala Ser Gly Ser Glu Arg His Leu Leu Ile Tyr Thr
1               5                   10                  15
Gly Gly Thr Leu Gly Met Gln Ser Lys Gly Val Leu Val Pro Gly
                20                  25                  30
Pro Gly Leu Val Thr Leu Leu Arg Thr Leu Pro Met Phe His Asp Lys
            35                  40                  45
Glu Phe Ala Arg Ala Arg Gly Leu Ser Glu Asp Thr Leu Val Leu Pro
    50                  55                  60
Pro Ala Ser Arg Asn Gln Arg Ile Leu Tyr Thr Val Leu Glu Cys Gln
65                  70                  75                  80
Pro Leu Leu Asp Ser Ser Asp Met Thr Ile Asp Trp Ile Arg Ile
                85                  90                  95
Ala Lys Ile Ile Glu Arg His Tyr Glu Gln Tyr Gln Gly Phe Val Val
            100                 105                 110
Ile His Gly Thr Asp Thr Met Ala Phe Ala Ala Ser Met Leu Ser Phe
        115                 120                 125
Met Leu Glu Asn Leu His Lys Pro Val Ile Leu Thr Gly Ala Gln Val
    130                 135                 140
Pro Ile Arg Val Leu Trp Asn Asp Ala Arg Glu Asn Leu Leu Gly Ala
145                 150                 155                 160
Leu Leu Val Ala Gly Gln Tyr Ile Ile Pro Glu Val Cys Leu Phe Met
                165                 170                 175
Asn Ser Gln Leu Phe Arg Gly Asn Arg Val Thr Lys Val Asp Ser Gln
            180                 185                 190
Lys Phe Glu Ala Phe Cys Ser Pro Asn Leu Ser Pro Leu Ala Thr Val
    195                 200                 205
Gly Ala Asp Val Thr Ile Ala Trp Asp Leu Val Arg Lys Val Lys Trp
210                 215                 220
Lys Asp Pro Leu Val Val His Ser Ser Met Glu Gln Asp Val Gly Leu
225                 230                 235                 240
Leu Arg Leu Tyr Pro Gly Ile Pro Ala Ser Leu Val Arg Ala Phe Leu
                245                 250                 255
Gln Pro Pro Leu Lys Gly Val Val Leu Glu Thr Phe Gly Ser Gly Asn
            260                 265                 270
Gly Pro Ser Lys Pro Asp Leu Leu Gln Glu Leu Arg Ala Ala Glu
    275                 280                 285
Arg Gly Leu Ile Met Val Asn Cys Ser Gln Cys Leu Arg Gly Ser Val
    290                 295                 300
Thr Pro Gly Tyr Ala Thr Ser Leu Ala Gly Ala Asn Ile Val Ser Gly
305                 310                 315                 320
Leu Asp Met Thr Ser Glu Ala Ala Leu Ala Lys Leu Ser Tyr Val Leu
                325                 330                 335
Gly Leu Pro Glu Leu Ser Leu Glu Arg Arg Gln Glu Leu Leu Ala Lys
            340                 345                 350
Asp Leu Arg Gly Glu Met Thr Pro Pro Ser Val Glu Arg Arg Pro
    355                 360                 365
Ser Leu Gln Gly Asn Thr Leu Gly Gly Val Ser Trp Leu Leu Ser
    370                 375                 380
Leu Ser Gly Ser Gln Glu Ala Asp Ala Leu Arg Asn Ala Leu Val Pro
385                 390                 395                 400
Ser Leu Ala Cys Ala Ala His Ala Gly Asp Val Glu Ala Leu Gln
                405                 410                 415
```

Ala Leu Val Glu Leu Gly Ser Asp Leu Gly Leu Val Asp Phe Asn Gly
            420                 425                 430

Gln Thr Pro Leu His Ala Ala Arg Gly Gly His Thr Glu Ala Val
        435                 440                 445

Thr Met Leu Leu Gln Arg Gly Val Asp Val Asn Thr Arg Asp Thr Asp
450                 455                 460

Gly Phe Ser Pro Leu Leu Ala Val Arg Gly Arg His Pro Gly Val
465                 470                 475                 480

Ile Gly Leu Leu Arg Glu Ala Gly Ala Ser Leu Ser Thr Gln Glu Leu
                485                 490                 495

Glu Glu Ala Gly Thr Glu Leu Cys Arg Leu Ala Tyr Arg Ala Asp Leu
            500                 505                 510

Glu Gly Leu Gln Val Trp Trp Gln Ala Gly Ala Asp Leu Gly Gln Pro
        515                 520                 525

Gly Tyr Asp Gly His Ser Ala Leu His Val Ala Glu Ala Ala Gly Asn
    530                 535                 540

Leu Ala Val Val Ala Phe Leu Gln Ser Leu Glu Gly Ala Val Gly Ala
545                 550                 555                 560

Gln Ala Pro Cys Pro Glu Val Leu Pro Gly Val
                565                 570

<210> SEQ ID NO 40
<211> LENGTH: 513
<212> TYPE: PRT
<213> ORGANISM: Artificial Sequence
<220> FEATURE:
<223> OTHER INFORMATION: Synthetic polypeptide

<400> SEQUENCE: 40

Met Ala Arg Ala Ser Gly Ser Glu Arg His Leu Leu Leu Ile Tyr Thr
1               5                   10                  15

Gly Gly Thr Leu Gly Met Gln Ser Lys Gly Gly Val Leu Val Pro Gly
                20                  25                  30

Pro Gly Leu Val Thr Leu Leu Arg Thr Leu Pro Met Phe His Asp Glu
            35                  40                  45

Glu His Ala Arg Ala Arg Gly Leu Ser Glu Asp Thr Leu Val Leu Pro
        50                  55                  60

Pro Ala Ser Arg Asn Gln Arg Ile Leu Tyr Thr Val Leu Glu Cys Gln
65                  70                  75                  80

Pro Leu Leu Asp Ser Ser Asp Met Thr Ile Asp Asp Trp Ile Arg Ile
                85                  90                  95

Ala Lys Ile Ile Glu Arg His Tyr Glu Gln Tyr Gln Gly Phe Val Val
                100                 105                 110

Ile His Gly Thr Asp Thr Met Ala Phe Ala Ala Ser Met Leu Ser Phe
            115                 120                 125

Met Leu Glu Asn Leu His Lys Pro Val Ile Leu Thr Gly Ala Gln Val
        130                 135                 140

Pro Ile His Ala Leu Trp Ser Asp Gly Arg Glu Asn Leu Leu Gly Ala
145                 150                 155                 160

Leu Leu Val Ala Gly Gln Tyr Ile Ile Pro Glu Val Cys Leu Phe Met
                165                 170                 175

Asn Ser Gln Leu Phe Arg Gly Asn Arg Val Thr Lys Val Asp Ser Gln
                180                 185                 190

Lys Phe Glu Ala Phe Cys Ser Pro Asn Leu Ser Pro Leu Ala Thr Val
            195                 200                 205

Gly Ala Asp Val Thr Ile Ala Trp Asp Leu Val Arg Lys Val Lys Trp
            210                 215                 220

Lys Asp Pro Leu Val Val His Ser Ser Met Glu Gln Asp Val Gly Leu
225                 230                 235                 240

Leu Arg Leu Tyr Pro Gly Ile Pro Ala Ser Leu Val Arg Ala Phe Leu
                245                 250                 255

Gln Pro Pro Leu Lys Gly Val Val Met Glu Thr Phe Gly Ser Gly Asn
            260                 265                 270

Gly Pro Thr Lys Pro Asp Leu Leu Gln Glu Leu Arg Ala Ala Ala Glu
            275                 280                 285

Arg Gly Leu Ile Met Val Asn Cys Ser Gln Cys Leu Arg Gly Ser Val
290                 295                 300

Thr Pro Gly Tyr Ala Thr Ser Leu Ala Gly Ala Asn Ile Val Ser Gly
305                 310                 315                 320

Leu Asp Met Thr Ser Glu Ala Ala Leu Ala Lys Leu Ser Tyr Val Leu
                325                 330                 335

Gly Leu Pro Glu Leu Ser Leu Glu Arg Arg Gln Glu Leu Leu Ala Lys
            340                 345                 350

Asp Leu Arg Gly Glu Met Thr Pro Pro Ser Val Glu Glu Arg Arg Pro
            355                 360                 365

Ser Leu Gln Gly Asn Thr Leu Gly Gly Val Ser Trp Leu Leu Ser
370                 375                 380

Leu Ser Gly Ser Gln Glu Ala Asp Ala Leu Arg Asn Ala Leu Val Pro
385                 390                 395                 400

Ser Leu Ala Cys Ala Ala Ala His Ala Gly Asp Val Glu Ala Leu Gln
                405                 410                 415

Ala Leu Val Glu Leu Gly Ser Asp Leu Gly Leu Val Asp Phe Asn Gly
            420                 425                 430

Gln Thr Pro Leu His Ala Ala Arg Gly Gly His Thr Glu Ala Val
            435                 440                 445

Thr Met Leu Leu Gln Arg Gly Val Asp Val Asn Thr Arg Asp Thr Asp
            450                 455                 460

Gly Phe Ser Pro Leu Leu Leu Ala Val Arg Gly Arg His Pro Gly Val
465                 470                 475                 480

Ile Gly Leu Leu Arg Glu Ala Gly Ala Ser Leu Ser Thr Gln Glu Leu
                485                 490                 495

Glu Glu Ala Gly Thr Glu Leu Cys Arg Leu Ala Tyr Arg Ala Asp Leu
            500                 505                 510

Glu

<210> SEQ ID NO 41
<211> LENGTH: 571
<212> TYPE: PRT
<213> ORGANISM: Artificial Sequence
<220> FEATURE:
<223> OTHER INFORMATION: Synthetic polypeptide

<400> SEQUENCE: 41

Met Ala Arg Ala Ser Gly Ser Glu Arg His Leu Leu Leu Ile Tyr Thr
1               5                   10                  15

Gly Gly Thr Leu Gly Met Gln Ser Lys Gly Gly Val Leu Val Pro Gly
            20                  25                  30

Pro Gly Leu Val Thr Leu Leu Arg Thr Leu Pro Met Phe His Asp Glu
            35                  40                  45

Glu His Ala Arg Ala Arg Gly Leu Ser Glu Asp Thr Leu Val Leu Pro

```
            50                  55                  60
Pro Ala Ser Arg Asn Gln Arg Ile Leu Tyr Thr Val Leu Glu Cys Gln
 65                  70                  75                  80

Pro Leu Phe Asp Ser Ser Asp Met Thr Ile Ala Glu Trp Val Cys Leu
                 85                  90                  95

Ala Gln Thr Ile Lys Arg His Tyr Glu Gln Tyr His Gly Phe Val Val
            100                 105                 110

Ile His Gly Thr Asp Thr Met Ala Phe Ala Ala Ser Met Leu Ser Phe
            115                 120                 125

Met Leu Glu Asn Leu His Lys Pro Val Ile Leu Thr Gly Ala Gln Val
            130                 135                 140

Pro Ile His Ala Leu Trp Ser Asp Gly Arg Glu Asn Leu Leu Gly Ala
145                 150                 155                 160

Leu Leu Met Ala Gly Gln Tyr Val Ile Pro Glu Val Cys Leu Phe Phe
                165                 170                 175

Gln Asn Gln Leu Phe Arg Gly Asn Arg Ala Thr Lys Val Asp Ala Arg
            180                 185                 190

Arg Phe Ala Ala Phe Cys Ser Pro Asn Leu Leu Pro Leu Ala Thr Val
            195                 200                 205

Gly Ala Asp Val Thr Ile Ala Trp Asp Leu Val Arg Lys Val Lys Trp
210                 215                 220

Lys Asp Pro Leu Val Val His Ser Asn Met Glu His Asp Val Ala Leu
225                 230                 235                 240

Leu Arg Leu Tyr Pro Gly Ile Pro Ala Ala Leu Val Arg Ala Phe Leu
                245                 250                 255

Gln Pro Pro Leu Lys Gly Val Val Leu Glu Thr Phe Gly Ser Gly Asn
            260                 265                 270

Gly Pro Ser Lys Pro Asp Leu Leu Gln Glu Leu Arg Ala Ala Ala Glu
            275                 280                 285

Arg Gly Leu Ile Met Val Asn Cys Ser Gln Cys Leu Arg Gly Ser Val
            290                 295                 300

Thr Pro Gly Tyr Ala Thr Ser Leu Ala Gly Ala Asn Ile Val Ser Gly
305                 310                 315                 320

Leu Asp Met Thr Ser Glu Ala Ala Leu Ala Lys Leu Ser Tyr Val Leu
                325                 330                 335

Gly Leu Pro Glu Leu Ser Leu Glu Arg Arg Gln Glu Leu Leu Ala Lys
            340                 345                 350

Asp Leu Arg Gly Glu Met Thr Pro Pro Ser Val Glu Glu Arg Arg Pro
            355                 360                 365

Ser Leu Gln Gly Asn Thr Leu Gly Gly Gly Val Ser Trp Leu Leu Ser
370                 375                 380

Leu Ser Gly Ser Gln Glu Ala Asp Ala Leu Arg Asn Ala Leu Val Pro
385                 390                 395                 400

Ser Leu Ala Cys Ala Ala Ala His Ala Gly Asp Val Glu Ala Leu Gln
                405                 410                 415

Ala Leu Val Glu Leu Gly Ser Asp Leu Gly Leu Val Asp Phe Asn Gly
            420                 425                 430

Gln Thr Pro Leu His Ala Ala Arg Gly Gly His Thr Glu Ala Val
            435                 440                 445

Thr Met Leu Leu Gln Arg Gly Val Asp Val Asn Thr Arg Asp Thr Asp
450                 455                 460

Gly Phe Ser Pro Leu Leu Leu Ala Val Arg Gly Arg His Pro Gly Val
465                 470                 475                 480
```

Ile Gly Leu Leu Arg Glu Ala Gly Ala Ser Leu Ser Thr Gln Glu Leu
                485                 490                 495

Glu Glu Ala Gly Thr Glu Leu Cys Arg Leu Ala Tyr Arg Ala Asp Leu
                500                 505                 510

Glu Gly Leu Gln Val Trp Trp Gln Ala Gly Ala Asp Leu Gly Gln Pro
                515                 520                 525

Gly Tyr Asp Gly His Ser Ala Leu His Val Ala Glu Ala Ala Gly Asn
                530                 535                 540

Leu Ala Val Val Ala Phe Leu Gln Ser Leu Glu Gly Ala Val Gly Ala
545                 550                 555                 560

Gln Ala Pro Cys Pro Glu Val Leu Pro Gly Val
                565                 570

<210> SEQ ID NO 42
<211> LENGTH: 571
<212> TYPE: PRT
<213> ORGANISM: Artificial Sequence
<220> FEATURE:
<223> OTHER INFORMATION: Synthetic polypeptide

<400> SEQUENCE: 42

Met Ala Arg Ala Ser Gly Ser Glu Arg His Leu Leu Leu Ile Tyr Thr
1               5                   10                  15

Gly Gly Thr Leu Gly Met Gln Ser Lys Gly Gly Val Leu Val Pro Gly
                20                  25                  30

Pro Gly Leu Val Thr Leu Leu Arg Thr Leu Pro Met Phe His Asp Glu
                35                  40                  45

Glu His Ala Arg Ala Arg Gly Leu Ser Glu Asp Thr Leu Val Leu Pro
            50                  55                  60

Pro Ala Ser Arg Asn Gln Arg Ile Leu Tyr Thr Val Leu Glu Cys Gln
65              70                  75                  80

Pro Leu Leu Asp Ser Ser Asp Met Thr Ile Asp Asp Trp Ile Arg Ile
                85                  90                  95

Ala Lys Ile Ile Glu Arg His Tyr Glu Gln Tyr His Gly Phe Val Val
                100                 105                 110

Ile His Gly Thr Asp Thr Met Ala Phe Ala Ala Ser Met Leu Ser Phe
            115                 120                 125

Met Leu Glu Asn Leu Gln Lys Thr Val Ile Leu Thr Gly Ala Gln Val
            130                 135                 140

Pro Ile Arg Val Leu Trp Asn Asp Ala Arg Glu Asn Leu Leu Gly Ala
145                 150                 155                 160

Leu Leu Val Ala Gly Gln Tyr Ile Ile Pro Glu Val Cys Leu Phe Met
                165                 170                 175

Ser Asn Gln Leu Phe Arg Gly Asn Arg Ala Thr Lys Val Asp Ala Arg
                180                 185                 190

Arg Phe Ala Ala Phe Cys Ser Pro Asn Leu Ser Pro Leu Ala Thr Val
            195                 200                 205

Gly Ala Asp Ile Thr Ile Asn Arg Glu Leu Val Arg Lys Val Asp Gly
            210                 215                 220

Lys Ala Gly Leu Val Val His Ser Ser Met Glu Gln Asp Val Gly Leu
225                 230                 235                 240

Leu Arg Leu Tyr Pro Gly Ile Pro Ala Ala Leu Val Arg Ala Phe Leu
                245                 250                 255

Gln Pro Pro Leu Lys Gly Val Val Met Glu Thr Phe Gly Ser Gly Asn
                260                 265                 270

Gly Pro Thr Lys Pro Asp Leu Leu Gln Glu Leu Arg Val Ala Thr Glu
            275                 280                 285

Arg Gly Leu Val Ile Val Asn Cys Thr His Cys Leu Gln Gly Ala Val
        290                 295                 300

Thr Thr Gly Tyr Ala Thr Ser Leu Ala Gly Ala Asn Ile Val Ser Gly
305                 310                 315                 320

Leu Asp Met Thr Ser Glu Ala Ala Leu Ala Lys Leu Ser Tyr Val Leu
                325                 330                 335

Gly Leu Pro Glu Leu Ser Leu Glu Arg Arg Gln Glu Leu Leu Ala Lys
            340                 345                 350

Asp Leu Arg Gly Glu Met Thr Pro Pro Ser Val Glu Arg Arg Pro
        355                 360                 365

Ser Leu Gln Gly Asn Thr Leu Gly Gly Val Ser Trp Leu Leu Ser
    370                 375                 380

Leu Ser Gly Ser Gln Glu Ala Asp Ala Leu Arg Asn Ala Leu Val Pro
385                 390                 395                 400

Ser Leu Ala Cys Ala Ala His Ala Gly Asp Val Glu Ala Leu Gln
                405                 410                 415

Ala Leu Val Glu Leu Gly Ser Asp Leu Gly Leu Val Asp Phe Asn Gly
            420                 425                 430

Gln Thr Pro Leu His Ala Ala Arg Gly Gly His Thr Glu Ala Val
        435                 440                 445

Thr Met Leu Leu Gln Arg Gly Val Asp Val Asn Thr Arg Asp Thr Asp
450                 455                 460

Gly Phe Ser Pro Leu Leu Ala Val Arg Gly Arg His Pro Gly Val
465                 470                 475                 480

Ile Gly Leu Leu Arg Glu Ala Gly Ala Ser Leu Ser Thr Gln Glu Leu
            485                 490                 495

Glu Glu Ala Gly Thr Glu Leu Cys Arg Leu Ala Tyr Arg Ala Asp Leu
                500                 505                 510

Glu Gly Leu Gln Val Trp Trp Gln Ala Gly Ala Asp Leu Gly Gln Pro
            515                 520                 525

Gly Tyr Asp Gly His Ser Ala Leu His Val Ala Glu Ala Ala Gly Asn
        530                 535                 540

Leu Ala Val Val Ala Phe Leu Gln Ser Leu Glu Gly Ala Val Gly Ala
545                 550                 555                 560

Gln Ala Pro Cys Pro Glu Val Leu Pro Gly Val
                565                 570

<210> SEQ ID NO 43
<211> LENGTH: 6
<212> TYPE: PRT
<213> ORGANISM: Artificial Sequence
<220> FEATURE:
<223> OTHER INFORMATION: Synthetic peptide

<400> SEQUENCE: 43

Ser Glu Asp Thr Leu Val
1               5

<210> SEQ ID NO 44
<211> LENGTH: 6
<212> TYPE: PRT
<213> ORGANISM: Artificial Sequence
<220> FEATURE:
<223> OTHER INFORMATION: Synthetic peptide

<400> SEQUENCE: 44

Pro Asp His Ala Leu Ala
1               5

<210> SEQ ID NO 45
<211> LENGTH: 369
<212> TYPE: PRT
<213> ORGANISM: Artificial Sequence
<220> FEATURE:
<223> OTHER INFORMATION: Synthetic polypeptide

<400> SEQUENCE: 45

Met Ala Arg Ala Ser Gly Ser Glu Arg His Leu Leu Leu Ile Tyr Thr
1               5                   10                  15

Gly Gly Thr Leu Gly Met Arg Ser Glu Gly Val Leu Val Pro Gly
                20                  25                  30

Pro Gly Leu Val Thr Leu Leu Arg Thr Leu Pro Met Phe His Asp Glu
            35                  40                  45

Glu Phe Ala Arg Ala Arg Gly Leu Pro Asp His Ala Leu Ala Leu Pro
    50                  55                  60

Pro Ala Ser His Gly Pro Arg Val Leu Tyr Thr Val Leu Glu Cys Gln
65                  70                  75                  80

Pro Leu Leu Asp Ser Ser Asp Met Thr Ile Asp Asp Trp Ile Arg Ile
                85                  90                  95

Ala Gln Ile Ile Lys Arg His Tyr Glu Gln Tyr Gln Gly Phe Val Val
                100                 105                 110

Ile His Gly Thr Asp Thr Met Ala Phe Ala Ala Ser Met Leu Ser Phe
            115                 120                 125

Met Leu Glu Asn Leu Gln Lys Pro Val Ile Leu Thr Gly Ala Gln Val
130                 135                 140

Pro Ile Arg Val Leu Trp Asn Asp Ala Arg Glu Asn Leu Leu Gly Ala
145                 150                 155                 160

Leu Leu Val Ala Gly Gln Tyr Ile Ile Pro Glu Val Cys Leu Phe Met
                165                 170                 175

Asn Ser Gln Leu Phe Arg Gly Asn Arg Val Thr Lys Val Asp Ser Gln
            180                 185                 190

Lys Phe Glu Ala Phe Cys Ser Pro Asn Leu Ser Pro Leu Ala Thr Val
        195                 200                 205

Gly Ala Asp Val Thr Ile Ala Trp Asp Leu Val Arg Lys Val Lys Trp
210                 215                 220

Lys Asp Pro Leu Val Val His Ser Ser Met Glu His Asp Val Ala Leu
225                 230                 235                 240

Leu Arg Leu Tyr Pro Gly Ile Pro Ala Ser Leu Val Arg Ala Phe Leu
                245                 250                 255

Gln Pro Pro Leu Lys Gly Val Val Leu Glu Thr Phe Gly Ser Gly Asn
            260                 265                 270

Gly Pro Ser Lys Pro Asp Leu Leu Gln Glu Leu Arg Ala Ala Ala Glu
        275                 280                 285

Arg Gly Leu Ile Met Val Asn Cys Ser Gln Cys Leu Arg Gly Ser Val
290                 295                 300

Thr Pro Gly Tyr Ala Thr Ser Leu Ala Gly Ala Asn Ile Val Ser Gly
305                 310                 315                 320

Leu Asp Met Thr Ser Glu Ala Ala Leu Ala Lys Leu Ser Tyr Val Leu
                325                 330                 335

Gly Leu Pro Glu Leu Ser Leu Asp Arg Arg Gln Glu Leu Leu Ala Lys

```
            340                 345                 350
Asp Leu Arg Gly Glu Met Thr Pro Pro Ser Val Glu Glu Arg Arg Pro
        355                 360                 365

Ser

<210> SEQ ID NO 46
<211> LENGTH: 369
<212> TYPE: PRT
<213> ORGANISM: Artificial Sequence
<220> FEATURE:
<223> OTHER INFORMATION: Synthetic polypeptide

<400> SEQUENCE: 46

Met Ala Arg Ala Ser Gly Ser Glu Arg Arg Leu Leu Ile Tyr Thr
 1               5                  10                  15

Gly Gly Thr Leu Gly Met Arg Ser Glu Gly Gly Val Leu Val Pro Gly
                20                  25                  30

Pro Gly Leu Val Thr Leu Leu Arg Thr Leu Pro Met Phe His Asp Glu
            35                  40                  45

Glu Phe Ala Arg Ala Arg Gly Leu Pro Asp His Ala Leu Ala Leu Pro
        50                  55                  60

Pro Ala Ser His Gly Pro Arg Val Leu Tyr Thr Val Leu Glu Cys Gln
 65                  70                  75                  80

Pro Leu Leu Asp Ser Ser Asp Met Thr Ile Ala Glu Trp Ile Arg Ile
                85                  90                  95

Ala Gln Ile Ile Lys Arg His Tyr Glu Gln Tyr His Gly Phe Val Val
                100                 105                 110

Ile His Gly Thr Asp Thr Met Ala Phe Ala Ala Ser Met Leu Ser Phe
            115                 120                 125

Met Leu Glu Asn Leu Gln Lys Pro Val Ile Leu Thr Gly Ala Gln Val
        130                 135                 140

Pro Ile Arg Val Leu Trp Asn Asp Ala Arg Glu Asn Leu Leu Gly Ala
145                 150                 155                 160

Leu Leu Val Ala Gly Gln Tyr Ile Ile Pro Glu Val Cys Leu Phe Met
                165                 170                 175

Asn Ser Gln Leu Phe Arg Gly Asn Arg Val Thr Lys Val Asp Ser Gln
            180                 185                 190

Lys Phe Glu Ala Phe Cys Ser Pro Asn Leu Ser Pro Leu Ala Thr Val
        195                 200                 205

Gly Ala Asp Val Thr Ile Ala Trp Asp Leu Val Arg Lys Val Lys Trp
    210                 215                 220

Lys Asp Pro Leu Val Val His Ser Ser Met Glu Gln Asp Val Ala Leu
225                 230                 235                 240

Leu Arg Leu Tyr Pro Gly Ile Pro Ala Ala Leu Val Arg Ala Phe Leu
                245                 250                 255

Gln Pro Pro Leu Lys Gly Val Val Leu Glu Thr Phe Gly Ser Gly Asn
            260                 265                 270

Gly Pro Ser Lys Pro Asp Leu Leu Gln Glu Leu Arg Ala Ala Ala Glu
        275                 280                 285

Arg Gly Leu Ile Met Val Asn Cys Ser Gln Cys Leu Arg Gly Ser Val
    290                 295                 300

Thr Pro Gly Tyr Ala Thr Ser Leu Ala Gly Ala Asn Ile Val Ser Gly
305                 310                 315                 320

Leu Asp Met Thr Ser Glu Ala Ala Leu Ala Lys Leu Ser Tyr Val Leu
                325                 330                 335
```

Gly Leu Pro Glu Leu Ser Leu Asp Arg Arg Gln Glu Leu Leu Ala Lys
            340                 345                 350

Asp Leu Arg Gly Glu Met Thr Pro Pro Ser Val Glu Arg Arg Pro
            355                 360                 365

Ser

<210> SEQ ID NO 47
<211> LENGTH: 369
<212> TYPE: PRT
<213> ORGANISM: Artificial Sequence
<220> FEATURE:
<223> OTHER INFORMATION: Synthetic polypeptide

<400> SEQUENCE: 47

Met Ala Arg Ala Ser Gly Ser Glu Arg Arg Leu Leu Leu Ile Tyr Thr
1               5                   10                  15

Gly Gly Thr Leu Gly Met Arg Ser Glu Gly Gly Val Leu Val Pro Gly
            20                  25                  30

Pro Gly Leu Val Thr Leu Leu Arg Thr Leu Pro Met Phe His Asp Glu
        35                  40                  45

Glu Phe Ala Arg Ala Arg Gly Leu Pro Asp His Ala Leu Ala Leu Pro
    50                  55                  60

Pro Ala Ser His Gly Pro Arg Val Leu Tyr Thr Val Leu Glu Cys Gln
65                  70                  75                  80

Pro Leu Leu Asp Ser Ser Asp Met Thr Ile Ala Glu Trp Ile Arg Ile
                85                  90                  95

Ala Gln Ile Ile Lys Arg His Tyr Glu Gln Tyr His Gly Phe Val Val
            100                 105                 110

Ile His Gly Thr Asp Thr Met Ala Phe Ala Ala Ser Met Leu Ser Phe
        115                 120                 125

Met Leu Glu Asn Leu Gln Lys Pro Val Ile Leu Thr Gly Ala Gln Val
130                 135                 140

Pro Ile His Val Leu Trp Asn Asp Ala Arg Glu Asn Leu Leu Gly Ala
145                 150                 155                 160

Leu Leu Val Ala Gly Gln Tyr Ile Ile Pro Glu Val Cys Leu Phe Met
                165                 170                 175

Asn Ser Gln Leu Phe Arg Gly Asn Arg Val Thr Lys Val Asp Ser Gln
            180                 185                 190

Arg Phe Glu Ala Phe Cys Ser Pro Asn Leu Ser Pro Leu Ala Thr Val
        195                 200                 205

Gly Ala Asp Val Thr Ile Ala Trp Glu Leu Val Arg Lys Val Lys Trp
    210                 215                 220

Lys Asp Pro Leu Val Val His Ser Ser Met Glu Gln Asp Val Ala Leu
225                 230                 235                 240

Leu Arg Leu Tyr Pro Gly Ile Pro Ala Ala Leu Val Arg Ala Phe Leu
                245                 250                 255

Gln Pro Pro Leu Lys Gly Val Val Leu Glu Thr Phe Gly Ser Gly Asn
            260                 265                 270

Gly Pro Ser Lys Pro Asp Leu Leu Gln Glu Leu Arg Ala Ala Ala Glu
        275                 280                 285

Arg Gly Leu Ile Met Val Asn Cys Ser Gln Cys Leu Gln Gly Ser Val
    290                 295                 300

Thr Pro Gly Tyr Ala Thr Ser Leu Ala Gly Ala Asn Ile Val Ser Gly
305                 310                 315                 320

Leu Asp Met Thr Ser Glu Ala Ala Leu Ala Lys Leu Ser Tyr Val Leu
            325                 330                 335

Gly Leu Pro Glu Leu Ser Leu Asp Arg Arg Gln Glu Leu Leu Ala Lys
        340                 345                 350

Asp Leu Arg Gly Glu Met Thr Pro Pro Ser Val Glu Glu Arg Arg Pro
        355                 360                 365

Ser

<210> SEQ ID NO 48
<211> LENGTH: 369
<212> TYPE: PRT
<213> ORGANISM: Artificial Sequence
<220> FEATURE:
<223> OTHER INFORMATION: Synthetic polypeptide

<400> SEQUENCE: 48

Met Ala Arg Ala Ser Gly Ser Glu Arg His Leu Leu Ile Tyr Thr
1               5                   10                  15

Gly Gly Thr Leu Gly Met Arg Ser Glu Gly Val Leu Val Pro Gly
            20                  25                  30

Pro Gly Leu Val Thr Leu Leu Arg Thr Leu Pro Met Phe His Asp Glu
        35                  40                  45

Glu Phe Ala Arg Ala Arg Gly Leu Ser Glu Asp Thr Leu Val Leu Pro
    50                  55                  60

Pro Ala Ser His Gly Pro Arg Val Leu Tyr Thr Val Leu Glu Cys Gln
65                  70                  75                  80

Pro Leu Leu Asp Ser Ser Asp Met Thr Ile Asp Asp Trp Ile Arg Ile
                85                  90                  95

Ala Gln Ile Ile Lys Arg His Tyr Glu Gln Tyr Gln Gly Phe Val Val
                100                 105                 110

Ile His Gly Thr Asp Thr Met Ala Phe Ala Ala Ser Met Leu Ser Phe
            115                 120                 125

Met Leu Glu Asn Leu Gln Lys Pro Val Ile Leu Thr Gly Ala Gln Val
        130                 135                 140

Pro Ile Arg Val Leu Trp Asn Asp Ala Arg Glu Asn Leu Leu Gly Ala
145                 150                 155                 160

Leu Leu Val Ala Gly Gln Tyr Ile Ile Pro Glu Val Cys Leu Phe Met
                165                 170                 175

Asn Ser Gln Leu Phe Arg Gly Asn Arg Val Thr Lys Val Asp Ser Gln
                180                 185                 190

Lys Phe Glu Ala Phe Cys Ser Pro Asn Leu Ser Pro Leu Ala Thr Val
        195                 200                 205

Gly Ala Asp Val Thr Ile Ala Trp Asp Leu Val Arg Lys Val Lys Trp
    210                 215                 220

Lys Asp Pro Leu Val Val His Ser Ser Met Glu His Asp Val Ala Leu
225                 230                 235                 240

Leu Arg Leu Tyr Pro Gly Ile Pro Ala Ser Leu Val Arg Ala Phe Leu
                245                 250                 255

Gln Pro Pro Leu Lys Gly Val Val Leu Glu Thr Phe Gly Ser Gly Asn
            260                 265                 270

Gly Pro Ser Lys Pro Asp Leu Leu Gln Glu Leu Arg Ala Ala Ala Glu
        275                 280                 285

Arg Gly Leu Ile Met Val Asn Cys Ser Gln Cys Leu Arg Gly Ser Val
    290                 295                 300

Thr Pro Gly Tyr Ala Thr Ser Leu Ala Gly Ala Asn Ile Val Ser Gly

```
                      305                 310                 315                 320
Leu Asp Met Thr Ser Glu Ala Ala Leu Ala Lys Leu Ser Tyr Val Leu
                325                 330                 335

Gly Leu Pro Glu Leu Ser Leu Asp Arg Arg Gln Glu Leu Leu Ala Lys
                340                 345                 350

Asp Leu Arg Gly Glu Met Thr Pro Pro Ser Val Glu Arg Arg Pro
                355                 360                 365

Ser

<210> SEQ ID NO 49
<211> LENGTH: 369
<212> TYPE: PRT
<213> ORGANISM: Artificial Sequence
<220> FEATURE:
<223> OTHER INFORMATION: Synthetic polypeptide

<400> SEQUENCE: 49

Met Ala Arg Ala Ser Gly Ser Glu Arg Arg Leu Leu Leu Ile Tyr Thr
1               5                   10                  15

Gly Gly Thr Leu Gly Met Arg Ser Glu Gly Val Leu Val Pro Gly
                20                  25                  30

Pro Gly Leu Val Thr Leu Leu Arg Thr Leu Pro Met Phe His Asp Glu
                35                  40                  45

Glu Phe Ala Arg Ala Arg Gly Leu Ser Glu Asp Thr Leu Val Leu Pro
        50                  55                  60

Pro Ala Ser His Gly Pro Arg Val Leu Tyr Thr Val Leu Glu Cys Gln
65                  70                  75                  80

Pro Leu Leu Asp Ser Ser Asp Met Thr Ile Ala Glu Trp Ile Arg Ile
                85                  90                  95

Ala Gln Ile Ile Lys Arg His Tyr Glu Gln Tyr His Gly Phe Val Val
                100                 105                 110

Ile His Gly Thr Asp Thr Met Ala Phe Ala Ala Ser Met Leu Ser Phe
            115                 120                 125

Met Leu Glu Asn Leu Gln Lys Pro Val Ile Leu Thr Gly Ala Gln Val
        130                 135                 140

Pro Ile Arg Val Leu Trp Asn Asp Ala Arg Glu Asn Leu Leu Gly Ala
145                 150                 155                 160

Leu Leu Val Ala Gly Gln Tyr Ile Ile Pro Glu Val Cys Leu Phe Met
                165                 170                 175

Asn Ser Gln Leu Phe Arg Gly Asn Arg Val Thr Lys Val Asp Ser Gln
                180                 185                 190

Lys Phe Glu Ala Phe Cys Ser Pro Asn Leu Ser Pro Leu Ala Thr Val
        195                 200                 205

Gly Ala Asp Val Thr Ile Ala Trp Asp Leu Val Arg Lys Val Lys Trp
    210                 215                 220

Lys Asp Pro Leu Val Val His Ser Ser Met Glu Gln Asp Val Ala Leu
225                 230                 235                 240

Leu Arg Leu Tyr Pro Gly Ile Pro Ala Ala Leu Val Arg Ala Phe Leu
                245                 250                 255

Gln Pro Pro Leu Lys Gly Val Val Leu Glu Thr Phe Gly Ser Gly Asn
                260                 265                 270

Gly Pro Ser Lys Pro Asp Leu Leu Gln Glu Leu Arg Ala Ala Ala Glu
        275                 280                 285

Arg Gly Leu Ile Met Val Asn Cys Ser Gln Cys Leu Arg Gly Ser Val
    290                 295                 300
```

```
Thr Pro Gly Tyr Ala Thr Ser Leu Ala Gly Ala Asn Ile Val Ser Gly
305                 310                 315                 320

Leu Asp Met Thr Ser Glu Ala Ala Leu Ala Lys Leu Ser Tyr Val Leu
            325                 330                 335

Gly Leu Pro Glu Leu Ser Leu Asp Arg Arg Gln Glu Leu Leu Ala Lys
        340                 345                 350

Asp Leu Arg Gly Glu Met Thr Pro Pro Ser Val Glu Glu Arg Arg Pro
    355                 360                 365

Ser
```

<210> SEQ ID NO 50
<211> LENGTH: 369
<212> TYPE: PRT
<213> ORGANISM: Artificial Sequence
<220> FEATURE:
<223> OTHER INFORMATION: Synthetic polypeptide

<400> SEQUENCE: 50

```
Met Ala Arg Ala Ser Gly Ser Glu Arg Arg Leu Leu Ile Tyr Thr
1               5                   10                  15

Gly Gly Thr Leu Gly Met Arg Ser Glu Gly Gly Val Leu Val Pro Gly
            20                  25                  30

Pro Gly Leu Val Thr Leu Leu Arg Thr Leu Pro Met Phe His Asp Glu
        35                  40                  45

Glu Phe Ala Arg Ala Arg Gly Leu Ser Glu Asp Thr Leu Val Leu Pro
    50                  55                  60

Pro Ala Ser His Gly Pro Arg Val Leu Tyr Thr Val Leu Glu Cys Gln
65                  70                  75                  80

Pro Leu Leu Asp Ser Ser Asp Met Thr Ile Ala Glu Trp Ile Arg Ile
                85                  90                  95

Ala Gln Ile Ile Lys Arg His Tyr Glu Gln Tyr His Gly Phe Val Val
                100                 105                 110

Ile His Gly Thr Asp Thr Met Ala Phe Ala Ala Ser Met Leu Ser Phe
            115                 120                 125

Met Leu Glu Asn Leu Gln Lys Pro Val Ile Leu Thr Gly Ala Gln Val
        130                 135                 140

Pro Ile His Val Leu Trp Asn Asp Ala Arg Glu Asn Leu Leu Gly Ala
145                 150                 155                 160

Leu Leu Val Ala Gly Gln Tyr Ile Ile Pro Glu Val Cys Leu Phe Met
                165                 170                 175

Asn Ser Gln Leu Phe Arg Gly Asn Arg Val Thr Lys Val Asp Ser Gln
                180                 185                 190

Arg Phe Glu Ala Phe Cys Ser Pro Asn Leu Ser Pro Leu Ala Thr Val
        195                 200                 205

Gly Ala Asp Val Thr Ile Ala Trp Glu Leu Val Arg Lys Val Lys Trp
    210                 215                 220

Lys Asp Pro Leu Val Val His Ser Ser Met Glu Gln Asp Val Ala Leu
225                 230                 235                 240

Leu Arg Leu Tyr Pro Gly Ile Pro Ala Ala Leu Val Arg Ala Phe Leu
                245                 250                 255

Gln Pro Pro Leu Lys Gly Val Val Leu Glu Thr Phe Gly Ser Gly Asn
            260                 265                 270

Gly Pro Ser Lys Pro Asp Leu Leu Gln Glu Leu Arg Ala Ala Ala Glu
        275                 280                 285
```

```
Arg Gly Leu Ile Met Val Asn Cys Ser Gln Cys Leu Gln Gly Ser Val
            290                 295                 300
Thr Pro Gly Tyr Ala Thr Ser Leu Ala Gly Ala Asn Ile Val Ser Gly
305                 310                 315                 320
Leu Asp Met Thr Ser Glu Ala Ala Leu Ala Lys Leu Ser Tyr Val Leu
                    325                 330                 335
Gly Leu Pro Glu Leu Ser Leu Asp Arg Arg Gln Glu Leu Leu Ala Lys
                340                 345                 350
Asp Leu Arg Gly Glu Met Thr Pro Pro Ser Val Glu Arg Arg Pro
            355                 360                 365
Ser
```

<210> SEQ ID NO 51
<211> LENGTH: 369
<212> TYPE: PRT
<213> ORGANISM: Artificial Sequence
<220> FEATURE:
<223> OTHER INFORMATION: Synthetic polypeptide

<400> SEQUENCE: 51

```
Met Ala Arg Ala Ser Gly Ser Glu Arg His Leu Leu Leu Ile Tyr Thr
1               5                   10                  15
Gly Gly Thr Leu Gly Met Gln Ser Lys Gly Gly Val Leu Val Pro Gly
                20                  25                  30
Pro Gly Leu Val Thr Leu Leu Arg Thr Leu Pro Met Phe His Asp Lys
            35                  40                  45
Glu Phe Ala Gln Ala Gln Gly Leu Pro Asp His Ala Leu Ala Leu Pro
        50                  55                  60
Pro Ala Ser His Gly Pro Arg Val Leu Tyr Thr Val Leu Glu Cys Gln
65                  70                  75                  80
Pro Leu Leu Asp Ser Ser Asp Met Thr Ile Asp Asp Trp Ile Arg Ile
                85                  90                  95
Ala Lys Ile Ile Glu Arg His Tyr Glu Gln Tyr Gln Gly Phe Val Val
                100                 105                 110
Ile His Gly Thr Asp Thr Met Ala Ser Gly Ala Ser Met Leu Ser Phe
            115                 120                 125
Met Leu Glu Asn Leu His Lys Pro Val Ile Leu Thr Gly Ala Gln Val
130                 135                 140
Pro Ile Arg Val Leu Trp Asn Asp Ala Arg Glu Asn Leu Leu Gly Ala
145                 150                 155                 160
Leu Leu Val Ala Gly Gln Tyr Ile Ile Pro Glu Val Cys Leu Phe Met
                165                 170                 175
Asn Ser Gln Leu Phe Arg Gly Asn Arg Val Thr Lys Val Asp Ser Gln
                180                 185                 190
Lys Phe Glu Ala Phe Ala Ser Pro Asn Leu Ser Pro Leu Ala Thr Val
            195                 200                 205
Gly Ala Asp Val Thr Ile Ala Trp Asp Leu Val Arg Lys Val Lys Trp
        210                 215                 220
Lys Asp Pro Leu Val Val His Ser Asn Met Glu His Asp Val Ala Leu
225                 230                 235                 240
Leu Arg Leu Tyr Pro Gly Ile Pro Ala Ser Leu Val Arg Ala Phe Leu
                245                 250                 255
Gln Pro Pro Leu Lys Gly Val Val Leu Glu Thr Phe Gly Ser Gly Asn
                260                 265                 270
Gly Pro Ser Lys Pro Asp Leu Leu Gln Glu Leu Arg Ala Ala Ala Gln
```

```
                      275                 280                 285
Arg Gly Leu Ile Met Val Asn Cys Ser Gln Cys Leu Arg Gly Ser Val
            290                 295                 300
Thr Pro Gly Tyr Ala Thr Ser Leu Ala Gly Ala Asn Ile Val Ser Gly
305                 310                 315                 320
Leu Asp Met Thr Ser Glu Ala Ala Leu Ala Lys Leu Ser Tyr Val Leu
                325                 330                 335
Gly Leu Pro Glu Leu Ser Leu Glu Arg Arg Gln Glu Leu Leu Ala Lys
            340                 345                 350
Asp Leu Arg Gly Glu Met Thr Leu Pro Thr Ala Asp Leu His Gln Ser
                355                 360                 365
Ser
```

<210> SEQ ID NO 52
<211> LENGTH: 369
<212> TYPE: PRT
<213> ORGANISM: Artificial Sequence
<220> FEATURE:
<223> OTHER INFORMATION: Synthetic polypeptide

<400> SEQUENCE: 52

```
Met Ala Arg Ala Ser Gly Ser Glu Arg His Leu Leu Ile Tyr Thr
1               5                   10                  15
Gly Gly Thr Leu Gly Met Gln Ser Lys Gly Gly Val Leu Val Pro Gly
            20                  25                  30
Pro Gly Leu Val Thr Leu Leu Arg Thr Leu Pro Met Phe His Asp Lys
            35                  40                  45
Glu Phe Ala Gln Ala Gln Gly Leu Pro Asp His Ala Leu Ala Leu Pro
50                  55                  60
Pro Ala Ser His Gly Pro Arg Val Leu Tyr Thr Val Leu Glu Cys Gln
65                  70                  75                  80
Pro Leu Leu Asp Ser Ser Asp Met Thr Ile Asp Asp Trp Ile Arg Ile
                85                  90                  95
Ala Lys Ile Ile Glu Arg His Tyr Glu Gln Tyr Gln Gly Phe Val Val
            100                 105                 110
Ile His Gly Thr Asp Thr Met Ala Ser Gly Ala Ser Met Leu Ser Phe
            115                 120                 125
Met Leu Glu Asn Leu His Lys Pro Val Ile Leu Thr Gly Ala Gln Val
            130                 135                 140
Pro Ile Arg Val Leu Trp Asn Asp Ala Arg Glu Asn Leu Leu Gly Ala
145                 150                 155                 160
Leu Leu Val Ala Gly Gln Tyr Ile Ile Pro Glu Val Cys Leu Phe Met
                165                 170                 175
Asn Ser Gln Leu Phe Arg Gly Asn Arg Val Thr Lys Val Asp Ser Gln
                180                 185                 190
Lys Phe Glu Ala Phe Ser Ser Pro Asn Leu Ser Pro Leu Ala Thr Val
            195                 200                 205
Gly Ala Asp Val Thr Ile Ala Trp Asp Leu Val Arg Lys Val Lys Trp
            210                 215                 220
Lys Asp Pro Leu Val Val His Ser Asn Met Glu His Asp Val Ala Leu
225                 230                 235                 240
Leu Arg Leu Tyr Pro Gly Ile Pro Ala Ser Leu Val Arg Ala Phe Leu
                245                 250                 255
Gln Pro Pro Leu Lys Gly Val Val Leu Glu Thr Phe Gly Ser Gly Asn
            260                 265                 270
```

Gly Pro Ser Lys Pro Asp Leu Leu Gln Glu Leu Arg Ala Ala Gln
            275                 280                 285

Arg Gly Leu Ile Met Val Asn Cys Ser Gln Cys Leu Arg Gly Ser Val
    290                 295                 300

Thr Pro Gly Tyr Ala Thr Ser Leu Ala Gly Ala Asn Ile Val Ser Gly
305                 310                 315                 320

Leu Asp Met Thr Ser Glu Ala Ala Leu Ala Lys Leu Ser Tyr Val Leu
                325                 330                 335

Gly Leu Pro Glu Leu Ser Leu Glu Arg Arg Gln Glu Leu Leu Ala Lys
            340                 345                 350

Asp Leu Arg Gly Glu Met Thr Leu Pro Thr Ala Asp Leu His Gln Ser
            355                 360                 365

Ser

<210> SEQ ID NO 53
<211> LENGTH: 369
<212> TYPE: PRT
<213> ORGANISM: Artificial Sequence
<220> FEATURE:
<223> OTHER INFORMATION: Synthetic polypeptide

<400> SEQUENCE: 53

Met Ala Arg Ala Ser Gly Ser Glu Arg His Leu Leu Leu Ile Tyr Thr
1               5                   10                  15

Gly Gly Thr Leu Gly Met Gln Ser Lys Gly Val Leu Val Pro Gly
            20                  25                  30

Pro Gly Leu Val Thr Leu Leu Arg Thr Leu Pro Met Phe His Asp Lys
            35                  40                  45

Glu Phe Ala Gln Ala Gln Gly Leu Pro Asp His Ala Leu Ala Leu Pro
    50                  55                  60

Pro Ala Ser His Gly Pro Arg Val Leu Tyr Thr Val Leu Glu Cys Gln
65                  70                  75                  80

Pro Leu Leu Asp Ser Ser Asp Met Thr Ile Asp Asp Trp Ile Arg Ile
                85                  90                  95

Ala Lys Ile Ile Glu Arg His Tyr Glu Gln Tyr Gln Gly Phe Val Val
            100                 105                 110

Ile His Gly Thr Asp Thr Met Ala Ser Gly Ala Ser Met Leu Ser Phe
        115                 120                 125

Met Leu Glu Asn Leu His Lys Pro Val Ile Leu Thr Gly Ala Gln Val
    130                 135                 140

Pro Ile Arg Val Leu Trp Asn Asp Ala Arg Glu Asn Leu Leu Gly Ala
145                 150                 155                 160

Leu Leu Val Ala Gly Gln Tyr Ile Ile Pro Glu Val Cys Leu Phe Met
                165                 170                 175

Asn Ser Gln Leu Phe Arg Gly Asn Arg Val Thr Lys Val Asp Ser Gln
            180                 185                 190

Lys Phe Glu Ala Phe Val Ser Pro Asn Leu Ser Pro Leu Ala Thr Val
        195                 200                 205

Gly Ala Asp Val Thr Ile Ala Trp Asp Leu Val Arg Lys Val Lys Trp
    210                 215                 220

Lys Asp Pro Leu Val Val His Ser Asn Met Glu His Asp Val Ala Leu
225                 230                 235                 240

Leu Arg Leu Tyr Pro Gly Ile Pro Ala Ser Leu Val Arg Ala Phe Leu
                245                 250                 255

```
Gln Pro Pro Leu Lys Gly Val Val Leu Glu Thr Phe Gly Ser Gly Asn
            260                 265                 270

Gly Pro Ser Lys Pro Asp Leu Leu Gln Glu Leu Arg Ala Ala Ala Gln
        275                 280                 285

Arg Gly Leu Ile Met Val Asn Cys Ser Gln Cys Leu Arg Gly Ser Val
    290                 295                 300

Thr Pro Gly Tyr Ala Thr Ser Leu Ala Gly Ala Asn Ile Val Ser Gly
305                 310                 315                 320

Leu Asp Met Thr Ser Glu Ala Ala Leu Ala Lys Leu Ser Tyr Val Leu
                325                 330                 335

Gly Leu Pro Glu Leu Ser Leu Glu Arg Arg Gln Glu Leu Leu Ala Lys
            340                 345                 350

Asp Leu Arg Gly Glu Met Thr Leu Pro Thr Ala Asp Leu His Gln Ser
        355                 360                 365

Ser

<210> SEQ ID NO 54
<211> LENGTH: 369
<212> TYPE: PRT
<213> ORGANISM: Artificial Sequence
<220> FEATURE:
<223> OTHER INFORMATION: Synthetic polypeptide

<400> SEQUENCE: 54

Met Ala Arg Ala Ser Gly Ser Glu Arg His Leu Leu Leu Ile Tyr Thr
1               5                   10                  15

Gly Gly Thr Leu Gly Met Gln Ser Lys Gly Gly Val Leu Val Pro Gly
            20                  25                  30

Pro Gly Leu Val Thr Leu Leu Arg Thr Leu Pro Met Phe His Asp Lys
        35                  40                  45

Glu Phe Ala Gln Ala Gln Gly Leu Pro Asp His Ala Leu Ala Leu Pro
    50                  55                  60

Pro Ala Ser His Gly Pro Arg Val Leu Tyr Thr Val Leu Glu Cys Gln
65                  70                  75                  80

Pro Leu Leu Asp Ser Ser Asp Met Thr Ile Asp Asp Trp Ile Arg Ile
                85                  90                  95

Ala Lys Ile Ile Glu Arg His Tyr Glu Gln Tyr Gln Gly Phe Val Val
            100                 105                 110

Ile His Gly Thr Asp Thr Met Ala Ser Gly Ala Ser Met Leu Ser Phe
        115                 120                 125

Met Leu Glu Asn Leu His Lys Pro Val Ile Leu Thr Gly Ala Gln Val
    130                 135                 140

Pro Ile Arg Val Leu Trp Asn Asp Ala Arg Glu Asn Leu Leu Gly Ala
145                 150                 155                 160

Leu Leu Val Ala Gly Gln Tyr Ile Ile Pro Glu Val Cys Leu Phe Met
                165                 170                 175

Asn Ser Gln Leu Phe Arg Gly Asn Arg Val Thr Lys Val Asp Ser Gln
            180                 185                 190

Lys Phe Glu Ala Phe Ala Ser Pro Asn Leu Ser Pro Leu Ala Thr Val
        195                 200                 205

Gly Ala Asp Val Thr Ile Ala Trp Asp Leu Val Arg Lys Val Lys Trp
    210                 215                 220

Cys Asp Pro Leu Val Val His Ser Asn Met Glu His Asp Val Ala Leu
225                 230                 235                 240

Leu Arg Leu Tyr Pro Gly Ile Pro Ala Ser Leu Val Arg Ala Phe Leu
```

```
                        245                 250                 255
Gln Pro Pro Leu Lys Gly Val Val Leu Glu Thr Phe Gly Ser Gly Asn
                260                 265                 270
Gly Pro Ser Lys Pro Asp Leu Leu Gln Glu Leu Arg Ala Ala Ala Gln
            275                 280                 285
Arg Gly Leu Ile Met Val Asn Cys Ser Gln Cys Leu Arg Gly Ser Val
        290                 295                 300
Thr Pro Gly Tyr Ala Thr Ser Leu Ala Gly Ala Asn Ile Val Ser Gly
305                 310                 315                 320
Leu Asp Met Thr Ser Glu Ala Ala Leu Ala Lys Leu Ser Tyr Val Leu
                325                 330                 335
Gly Leu Pro Glu Leu Ser Leu Glu Arg Arg Gln Glu Leu Leu Ala Lys
                340                 345                 350
Asp Leu Arg Gly Glu Met Thr Leu Pro Thr Ala Asp Leu His Gln Ser
            355                 360                 365
Ser
```

<210> SEQ ID NO 55
<211> LENGTH: 369
<212> TYPE: PRT
<213> ORGANISM: Artificial Sequence
<220> FEATURE:
<223> OTHER INFORMATION: Synthetic polypeptide

<400> SEQUENCE: 55

```
Met Ala Arg Ala Ser Gly Ser Glu Arg His Leu Leu Leu Ile Tyr Thr
1               5                   10                  15
Gly Gly Thr Leu Gly Met Gln Ser Lys Gly Gly Val Leu Val Pro Gly
                20                  25                  30
Pro Gly Leu Val Thr Leu Leu Arg Thr Leu Pro Met Phe His Asp Lys
            35                  40                  45
Glu Phe Ala Gln Ala Gln Gly Leu Pro Asp His Ala Leu Ala Leu Pro
        50                  55                  60
Pro Ala Ser His Gly Pro Arg Val Leu Tyr Thr Val Leu Glu Cys Gln
65                  70                  75                  80
Pro Leu Leu Asp Ser Ser Asp Met Thr Ile Asp Asp Trp Ile Arg Ile
                85                  90                  95
Ala Lys Ile Ile Glu Arg His Tyr Glu Gln Tyr Gln Gly Phe Val Val
                100                 105                 110
Ile His Gly Thr Asp Thr Met Ala Ser Gly Ala Ser Met Leu Ser Phe
            115                 120                 125
Met Leu Glu Asn Leu His Lys Pro Val Ile Leu Thr Gly Ala Gln Val
        130                 135                 140
Pro Ile Arg Val Leu Trp Asn Asp Ala Arg Glu Asn Leu Leu Gly Ala
145                 150                 155                 160
Leu Leu Val Ala Gly Gln Tyr Ile Ile Pro Glu Val Cys Leu Phe Met
                165                 170                 175
Asn Ser Gln Leu Phe Arg Gly Asn Arg Val Thr Lys Val Asp Ser Gln
                180                 185                 190
Lys Phe Glu Ala Phe Ala Ser Pro Asn Leu Ser Pro Leu Ala Thr Val
            195                 200                 205
Gly Ala Asp Val Thr Ile Ala Trp Asp Leu Val Arg Lys Val Lys Trp
        210                 215                 220
Cys Asp Pro Leu Val Val His Ser Asn Met Glu His Asp Val Ala Leu
225                 230                 235                 240
```

Leu Arg Leu Tyr Pro Gly Ile Pro Ala Ser Leu Val Arg Ala Phe Leu
            245                 250                 255

Gln Pro Pro Leu Lys Gly Val Val Leu Glu Thr Phe Gly Ser Gly Asn
        260                 265                 270

Gly Pro Ser Lys Pro Asp Leu Leu Gln Glu Leu Arg Ala Ala Gln
        275                 280                 285

Arg Gly Leu Ile Met Val Asn Cys Ser Gln Cys Leu Arg Gly Ser Val
290                 295                 300

Thr Pro Gly Tyr Ala Thr Ser Leu Ala Gly Ala Asn Ile Val Ser Gly
305                 310                 315                 320

Leu Asp Met Thr Ser Glu Ala Ala Leu Ala Lys Leu Ser Tyr Val Leu
                325                 330                 335

Gly Leu Pro Cys Leu Ser Leu Glu Arg Arg Gln Glu Leu Leu Ala Lys
            340                 345                 350

Asp Leu Arg Gly Glu Met Thr Leu Pro Thr Ala Asp Leu His Gln Ser
        355                 360                 365

Ser

<210> SEQ ID NO 56
<211> LENGTH: 369
<212> TYPE: PRT
<213> ORGANISM: Artificial Sequence
<220> FEATURE:
<223> OTHER INFORMATION: Synthetic polypeptide

<400> SEQUENCE: 56

Met Ala Arg Ala Ser Gly Ser Glu Arg His Leu Leu Leu Ile Tyr Thr
1               5                   10                  15

Gly Gly Thr Leu Gly Met Gln Ser Lys Gly Gly Val Leu Val Pro Gly
            20                  25                  30

Pro Gly Leu Val Thr Leu Leu Arg Thr Leu Pro Met Phe His Asp Lys
        35                  40                  45

Cys Phe Ala Gln Ala Gln Gly Leu Pro Asp His Ala Leu Ala Leu Pro
    50                  55                  60

Pro Ala Ser His Gly Pro Arg Val Leu Tyr Thr Val Leu Glu Cys Gln
65                  70                  75                  80

Pro Leu Leu Asp Ser Ser Asp Met Thr Ile Asp Asp Trp Ile Arg Ile
                85                  90                  95

Ala Lys Ile Ile Glu Arg His Tyr Glu Gln Tyr Gln Gly Phe Val Val
            100                 105                 110

Ile His Gly Thr Asp Thr Met Ala Ser Gly Ala Ser Met Leu Ser Phe
        115                 120                 125

Met Leu Glu Asn Leu His Lys Pro Val Ile Leu Thr Gly Ala Gln Val
    130                 135                 140

Pro Ile Arg Val Leu Trp Asn Asp Ala Arg Glu Asn Leu Leu Gly Ala
145                 150                 155                 160

Leu Leu Val Ala Gly Gln Tyr Ile Ile Pro Glu Val Cys Leu Phe Met
                165                 170                 175

Asn Ser Gln Leu Phe Arg Gly Asn Arg Val Thr Lys Val Asp Ser Gln
            180                 185                 190

Lys Phe Glu Ala Phe Ala Ser Pro Asn Leu Ser Pro Leu Ala Thr Val
        195                 200                 205

Gly Ala Asp Val Thr Ile Ala Trp Asp Leu Val Arg Lys Val Lys Trp
    210                 215                 220

```
Cys Asp Pro Leu Val Val His Ser Asn Met Glu His Asp Val Ala Leu
225                 230                 235                 240

Leu Arg Leu Tyr Pro Gly Ile Pro Ala Ser Leu Val Arg Ala Phe Leu
            245                 250                 255

Gln Pro Pro Leu Lys Gly Val Val Leu Glu Thr Phe Gly Ser Gly Asn
        260                 265                 270

Gly Pro Ser Lys Pro Asp Leu Leu Gln Glu Leu Arg Ala Ala Ala Gln
    275                 280                 285

Arg Gly Leu Ile Met Val Asn Cys Ser Gln Cys Leu Arg Gly Ser Val
290                 295                 300

Thr Pro Gly Tyr Ala Thr Ser Leu Ala Gly Ala Asn Ile Val Ser Gly
305                 310                 315                 320

Leu Asp Met Thr Ser Glu Ala Ala Leu Ala Lys Leu Ser Tyr Val Leu
            325                 330                 335

Gly Leu Pro Cys Leu Ser Leu Glu Arg Arg Gln Glu Leu Leu Ala Lys
        340                 345                 350

Asp Leu Arg Gly Glu Met Thr Leu Pro Thr Ala Asp Leu His Gln Ser
    355                 360                 365

Ser

<210> SEQ ID NO 57
<211> LENGTH: 369
<212> TYPE: PRT
<213> ORGANISM: Artificial Sequence
<220> FEATURE:
<223> OTHER INFORMATION: Synthetic polypeptide

<400> SEQUENCE: 57

Met Ala Arg Ala Ser Gly Ser Glu Arg His Leu Leu Leu Ile Tyr Thr
1               5                   10                  15

Gly Gly Thr Leu Gly Met Gln Ser Lys Gly Gly Val Leu Val Pro Gly
            20                  25                  30

Pro Gly Leu Val Thr Leu Leu Arg Thr Leu Pro Met Phe His Asp Lys
        35                  40                  45

Cys Phe Ala Gln Ala Gln Gly Leu Pro Asp His Ala Leu Ala Leu Pro
    50                  55                  60

Pro Ala Ser His Gly Pro Arg Val Leu Tyr Thr Val Leu Glu Cys Gln
65                  70                  75                  80

Pro Leu Leu Asp Ser Ser Asp Met Thr Ile Asp Asp Trp Ile Arg Ile
                85                  90                  95

Ala Lys Ile Ile Glu Arg His Tyr Glu Gln Tyr Gln Gly Phe Val Val
            100                 105                 110

Ile His Gly Thr Asp Thr Met Ala Ser Gly Ala Ser Met Leu Ser Phe
        115                 120                 125

Met Leu Glu Asn Leu His Lys Pro Val Ile Leu Thr Gly Ala Gln Val
    130                 135                 140

Pro Ile Arg Val Leu Trp Asn Asp Ala Arg Glu Asn Leu Leu Gly Ala
145                 150                 155                 160

Leu Leu Val Ala Gly Gln Tyr Ile Ile Pro Glu Val Cys Leu Phe Met
                165                 170                 175

Asn Ser Gln Leu Phe Arg Gly Asn Arg Val Thr Lys Val Asp Ser Gln
            180                 185                 190

Lys Phe Glu Ala Phe Ala Ser Pro Asn Leu Ser Pro Leu Ala Thr Val
        195                 200                 205

Gly Ala Asp Val Thr Ile Ala Trp Asp Leu Val Arg Lys Val Lys Trp
```

```
            210                 215                 220
Cys Asp Pro Leu Val Val His Ser Asn Met Glu His Asp Val Ala Leu
225                 230                 235                 240

Leu Arg Leu Tyr Pro Gly Ile Pro Ala Ser Leu Val Arg Ala Phe Leu
                245                 250                 255

Cys Pro Pro Leu Lys Gly Val Val Leu Glu Thr Phe Gly Ser Gly Asn
                260                 265                 270

Gly Pro Ser Lys Pro Asp Leu Leu Gln Glu Leu Arg Ala Ala Gln
            275                 280                 285

Arg Gly Leu Ile Met Val Asn Cys Ser Gln Cys Leu Arg Gly Ser Val
        290                 295                 300

Thr Pro Gly Tyr Ala Thr Ser Leu Ala Gly Ala Asn Ile Val Ser Gly
305                 310                 315                 320

Leu Asp Met Thr Ser Glu Ala Ala Leu Ala Lys Leu Ser Tyr Val Leu
                325                 330                 335

Gly Leu Pro Cys Leu Ser Leu Glu Arg Arg Gln Glu Leu Leu Ala Lys
                340                 345                 350

Asp Leu Arg Gly Glu Met Thr Leu Pro Thr Ala Asp Leu His Gln Ser
                355                 360                 365

Ser

<210> SEQ ID NO 58
<211> LENGTH: 369
<212> TYPE: PRT
<213> ORGANISM: Artificial Sequence
<220> FEATURE:
<223> OTHER INFORMATION: Synthetic polypeptide

<400> SEQUENCE: 58

Met Ala Arg Ala Ser Gly Ser Glu Arg Leu Leu Leu Ile Tyr Thr
1               5                   10                  15

Gly Gly Thr Leu Gly Met Arg Ser Glu Gly Gly Val Leu Val Pro Gly
            20                  25                  30

Pro Gly Leu Val Thr Leu Leu Arg Thr Leu Pro Met Phe His Asp Glu
        35                  40                  45

Glu Phe Ala Arg Ala Arg Gly Leu Ser Glu Asp Thr Leu Val Leu Pro
    50                  55                  60

Pro Ala Ser His Gly Pro Arg Val Leu Tyr Thr Val Leu Glu Cys Gln
65                  70                  75                  80

Pro Leu Leu Asp Ser Ser Asp Met Thr Ile Ala Glu Trp Ile Arg Ile
                85                  90                  95

Ala Gln Ile Ile Lys Arg His Tyr Glu Gln Tyr His Gly Phe Val Val
                100                 105                 110

Ile His Gly Thr Asp Thr Met Ala Phe Ala Ala Ser Met Leu Ser Phe
            115                 120                 125

Met Leu Glu Asn Leu Gln Lys Pro Val Ile Leu Thr Gly Ala Gln Val
        130                 135                 140

Pro Ile His Val Leu Trp Asn Asp Ala Arg Glu Asn Leu Leu Gly Ala
145                 150                 155                 160

Leu Leu Val Ala Gly Gln Tyr Ile Ile Pro Glu Val Cys Leu Phe Met
                165                 170                 175

Asn Ser Gln Leu Phe Arg Gly Asn Arg Val Thr Lys Val Asp Ser Gln
            180                 185                 190

Arg Phe Glu Ala Phe Ala Ser Pro Asn Leu Ser Pro Leu Ala Thr Val
        195                 200                 205
```

```
Gly Ala Asp Val Thr Ile Ala Trp Glu Leu Val Arg Lys Val Lys Trp
            210                 215                 220
Lys Asp Pro Leu Val Val His Ser Ser Met Glu Gln Asp Val Ala Leu
225                 230                 235                 240
Leu Arg Leu Tyr Pro Gly Ile Pro Ala Ala Leu Val Arg Ala Phe Leu
                245                 250                 255
Gln Pro Pro Leu Lys Gly Val Val Leu Glu Thr Phe Gly Ser Gly Asn
                260                 265                 270
Gly Pro Ser Lys Pro Asp Leu Leu Gln Glu Leu Arg Ala Ala Ala Glu
                275                 280                 285
Arg Gly Leu Ile Met Val Asn Cys Ser Gln Cys Leu Gln Gly Ser Val
            290                 295                 300
Thr Pro Gly Tyr Ala Thr Ser Leu Ala Gly Ala Asn Ile Val Ser Gly
305                 310                 315                 320
Leu Asp Met Thr Ser Glu Ala Ala Leu Ala Lys Leu Ser Tyr Val Leu
                325                 330                 335
Gly Leu Pro Glu Leu Ser Leu Asp Arg Arg Gln Glu Leu Leu Ala Lys
                340                 345                 350
Asp Leu Arg Gly Glu Met Thr Pro Pro Ser Val Glu Glu Arg Arg Pro
            355                 360                 365
Ser

<210> SEQ ID NO 59
<211> LENGTH: 369
<212> TYPE: PRT
<213> ORGANISM: Artificial Sequence
<220> FEATURE:
<223> OTHER INFORMATION: Synthetic polypeptide

<400> SEQUENCE: 59

Met Ala Arg Ala Ser Gly Ser Glu Arg Arg Leu Leu Leu Ile Tyr Thr
1               5                   10                  15
Gly Gly Thr Leu Gly Met Arg Ser Glu Gly Val Leu Val Pro Gly
            20                  25                  30
Pro Gly Leu Val Thr Leu Leu Arg Thr Leu Pro Met Phe His Asp Glu
                35                  40                  45
Glu Phe Ala Cys Ala Arg Gly Leu Ser Glu Asp Thr Leu Val Leu Pro
50                  55                  60
Pro Ala Ser His Gly Pro Arg Val Leu Tyr Thr Val Leu Glu Cys Gln
65                  70                  75                  80
Pro Leu Leu Asp Ser Ser Asp Met Thr Ile Ala Glu Trp Ile Arg Ile
                85                  90                  95
Ala Gln Ile Ile Lys Arg His Tyr Glu Gln Tyr His Gly Phe Val Val
                100                 105                 110
Ile His Gly Thr Asp Thr Met Ala Phe Ala Ala Ser Met Leu Ser Phe
            115                 120                 125
Met Leu Glu Asn Leu Gln Lys Pro Val Ile Leu Thr Gly Ala Gln Val
130                 135                 140
Pro Ile His Val Leu Trp Asn Asp Ala Arg Glu Asn Leu Leu Gly Ala
145                 150                 155                 160
Leu Leu Val Ala Gly Gln Tyr Ile Ile Pro Glu Val Cys Leu Phe Met
                165                 170                 175
Asn Ser Gln Leu Phe Arg Gly Asn Arg Val Thr Lys Val Asp Ser Gln
                180                 185                 190
```

Arg Phe Glu Ala Phe Ala Ser Pro Asn Leu Ser Pro Leu Ala Thr Val
            195                 200                 205

Gly Ala Asp Val Thr Ile Ala Trp Glu Leu Val Arg Lys Val Lys Trp
210                 215                 220

Lys Asp Pro Leu Val Val His Ser Ser Met Glu Gln Asp Val Ala Leu
225                 230                 235                 240

Leu Arg Leu Tyr Pro Gly Ile Pro Ala Ala Leu Val Arg Ala Phe Leu
            245                 250                 255

Gln Pro Pro Leu Lys Gly Val Val Leu Glu Thr Phe Gly Ser Gly Asn
            260                 265                 270

Gly Pro Ser Lys Pro Asp Leu Leu Gln Glu Leu Arg Ala Ala Ala Glu
            275                 280                 285

Arg Gly Leu Ile Met Val Asn Cys Ser Gln Cys Leu Gln Gly Ser Val
290                 295                 300

Thr Pro Gly Tyr Ala Thr Ser Leu Ala Gly Ala Asn Ile Val Ser Gly
305                 310                 315                 320

Leu Asp Met Thr Ser Glu Ala Ala Leu Ala Lys Leu Ser Tyr Val Leu
            325                 330                 335

Gly Leu Pro Glu Leu Ser Leu Asp Arg Arg Gln Glu Leu Leu Ala Lys
            340                 345                 350

Asp Leu Arg Gly Glu Met Thr Pro Pro Ser Val Glu Glu Arg Arg Pro
            355                 360                 365

Ser

<210> SEQ ID NO 60
<211> LENGTH: 369
<212> TYPE: PRT
<213> ORGANISM: Artificial Sequence
<220> FEATURE:
<223> OTHER INFORMATION: Synthetic polypeptide

<400> SEQUENCE: 60

Met Ala Arg Ala Ser Gly Ser Glu Arg Arg Leu Leu Leu Ile Tyr Thr
1               5                   10                  15

Gly Gly Thr Leu Gly Met Arg Ser Glu Gly Gly Val Leu Val Pro Gly
            20                  25                  30

Pro Gly Leu Val Thr Leu Leu Arg Thr Leu Pro Met Phe His Asp Glu
            35                  40                  45

Glu Phe Ala Cys Ala Arg Gly Leu Ser Glu Asp Thr Leu Val Leu Pro
50                  55                  60

Pro Ala Ser His Gly Pro Arg Val Leu Tyr Thr Val Leu Glu Cys Gln
65                  70                  75                  80

Pro Leu Leu Asp Ser Ser Asp Met Thr Ile Ala Glu Trp Ile Arg Ile
            85                  90                  95

Ala Gln Ile Ile Lys Arg His Tyr Glu Gln Tyr His Gly Phe Val Val
            100                 105                 110

Ile His Gly Thr Asp Thr Met Ala Phe Ala Ala Ser Met Leu Ser Phe
            115                 120                 125

Met Leu Glu Asn Leu Gln Lys Pro Val Ile Leu Thr Gly Ala Gln Val
130                 135                 140

Pro Ile His Val Leu Trp Asn Asp Ala Arg Glu Asn Leu Leu Gly Ala
145                 150                 155                 160

Leu Leu Val Ala Gly Gln Tyr Ile Ile Pro Glu Val Cys Leu Phe Met
            165                 170                 175

Asn Ser Gln Leu Phe Arg Gly Asn Arg Val Thr Lys Val Asp Ser Gln

```
                180                 185                 190
Arg Phe Glu Ala Phe Ala Ser Pro Asn Leu Ser Pro Leu Ala Thr Val
            195                 200                 205
Gly Ala Asp Val Thr Ile Ala Trp Glu Leu Val Arg Lys Val Lys Trp
        210                 215                 220
Cys Asp Pro Leu Val Val His Ser Ser Met Glu Gln Asp Val Ala Leu
225                 230                 235                 240
Leu Arg Leu Tyr Pro Gly Ile Pro Ala Ala Leu Val Arg Ala Phe Leu
                245                 250                 255
Gln Pro Pro Leu Lys Gly Val Val Leu Glu Thr Phe Gly Ser Gly Asn
            260                 265                 270
Gly Pro Ser Lys Pro Asp Leu Leu Gln Glu Leu Arg Ala Ala Ala Glu
        275                 280                 285
Arg Gly Leu Ile Met Val Asn Cys Ser Gln Cys Leu Gln Gly Ser Val
    290                 295                 300
Thr Pro Gly Tyr Ala Thr Ser Leu Ala Gly Ala Asn Ile Val Ser Gly
305                 310                 315                 320
Leu Asp Met Thr Ser Glu Ala Ala Leu Ala Lys Leu Ser Tyr Val Leu
                325                 330                 335
Gly Leu Pro Glu Leu Ser Leu Asp Arg Arg Gln Glu Leu Leu Ala Lys
            340                 345                 350
Asp Leu Arg Gly Glu Met Thr Pro Pro Ser Val Glu Gly Arg Arg Pro
        355                 360                 365
Ser
```

<210> SEQ ID NO 61
<211> LENGTH: 369
<212> TYPE: PRT
<213> ORGANISM: Artificial Sequence
<220> FEATURE:
<223> OTHER INFORMATION: Synthetic polypeptide

<400> SEQUENCE: 61

```
Met Ala Arg Ala Ser Gly Ser Glu Arg Arg Leu Leu Leu Ile Tyr Thr
1               5                   10                  15
Gly Gly Thr Leu Gly Met Arg Ser Glu Gly Gly Val Leu Val Pro Gly
            20                  25                  30
Pro Gly Leu Val Thr Leu Leu Arg Thr Leu Pro Met Phe His Asp Glu
        35                  40                  45
Glu Phe Ala Cys Ala Arg Gly Leu Ser Glu Asp Thr Leu Val Leu Pro
    50                  55                  60
Pro Ala Ser His Gly Pro Arg Val Leu Tyr Thr Val Leu Glu Cys Gln
65                  70                  75                  80
Pro Leu Leu Asp Ser Ser Asp Met Thr Ile Ala Glu Trp Ile Arg Ile
                85                  90                  95
Ala Gln Ile Ile Lys Arg His Tyr Glu Gln Tyr His Gly Phe Val Val
            100                 105                 110
Ile His Gly Thr Asp Thr Met Ala Phe Ala Ala Ser Met Leu Ser Phe
        115                 120                 125
Met Leu Glu Asn Leu Gln Lys Pro Val Ile Leu Thr Gly Ala Gln Val
    130                 135                 140
Pro Ile His Val Leu Trp Asn Asp Ala Arg Glu Asn Leu Leu Gly Ala
145                 150                 155                 160
Leu Leu Val Ala Gly Gln Tyr Ile Ile Pro Glu Val Cys Leu Phe Met
                165                 170                 175
```

```
Asn Ser Gln Leu Phe Arg Gly Asn Arg Val Thr Lys Val Asp Ser Gln
                180                 185                 190

Arg Phe Glu Ala Phe Ala Ser Pro Asn Leu Ser Pro Leu Ala Thr Val
            195                 200                 205

Gly Ala Asp Val Thr Ile Ala Trp Glu Leu Val Arg Lys Val Lys Trp
210                 215                 220

Cys Asp Pro Leu Val Val His Ser Ser Met Glu Gln Asp Val Ala Leu
225                 230                 235                 240

Leu Arg Leu Tyr Pro Gly Ile Pro Ala Ala Leu Val Arg Ala Phe Leu
                245                 250                 255

Gln Pro Pro Leu Lys Gly Val Val Leu Glu Thr Phe Gly Ser Gly Asn
            260                 265                 270

Gly Pro Ser Lys Pro Asp Leu Leu Gln Glu Leu Arg Ala Ala Ala Glu
        275                 280                 285

Arg Gly Leu Ile Met Val Asn Cys Ser Gln Cys Leu Gln Gly Ser Val
    290                 295                 300

Thr Pro Gly Tyr Ala Thr Ser Leu Ala Gly Ala Asn Ile Val Ser Gly
305                 310                 315                 320

Leu Asp Met Thr Ser Glu Ala Ala Leu Ala Lys Leu Ser Tyr Val Leu
                325                 330                 335

Gly Leu Pro Cys Leu Ser Leu Asp Arg Arg Gln Glu Leu Leu Ala Lys
            340                 345                 350

Asp Leu Arg Gly Glu Met Thr Pro Pro Ser Val Glu Glu Arg Arg Pro
        355                 360                 365

Ser

<210> SEQ ID NO 62
<211> LENGTH: 369
<212> TYPE: PRT
<213> ORGANISM: Artificial Sequence
<220> FEATURE:
<223> OTHER INFORMATION: Synthetic polypeptide

<400> SEQUENCE: 62

Met Ala Arg Ala Ser Gly Ser Glu Arg Arg Leu Leu Leu Ile Tyr Thr
1               5                   10                  15

Gly Gly Thr Leu Gly Met Arg Ser Glu Gly Gly Val Leu Val Pro Gly
                20                  25                  30

Pro Gly Leu Val Thr Leu Leu Arg Thr Leu Pro Met Phe His Asp Glu
            35                  40                  45

Glu Phe Ala Cys Ala Arg Gly Leu Ser Glu Asp Thr Leu Val Leu Pro
        50                  55                  60

Pro Ala Ser His Gly Pro Arg Val Leu Tyr Thr Val Leu Glu Cys Gln
65                  70                  75                  80

Pro Leu Leu Asp Ser Ser Asp Met Thr Ile Ala Glu Trp Ile Arg Ile
                85                  90                  95

Ala Gln Ile Ile Lys Arg His Tyr Glu Gln Tyr His Gly Phe Val Val
                100                 105                 110

Ile His Gly Thr Asp Thr Met Ala Phe Ala Ala Ser Met Leu Ser Phe
            115                 120                 125

Met Leu Glu Asn Leu Gln Lys Pro Val Ile Leu Thr Gly Ala Gln Val
        130                 135                 140

Pro Ile His Val Leu Trp Asn Asp Ala Arg Glu Asn Leu Leu Gly Ala
145                 150                 155                 160
```

```
Leu Leu Val Ala Gly Gln Tyr Ile Ile Pro Glu Val Cys Leu Phe Met
                165                 170                 175

Asn Ser Gln Leu Phe Arg Gly Asn Arg Val Thr Lys Val Asp Ser Gln
            180                 185                 190

Arg Phe Glu Ala Phe Ala Ser Pro Asn Leu Ser Pro Leu Ala Thr Val
        195                 200                 205

Gly Ala Asp Val Thr Ile Ala Trp Glu Leu Val Arg Lys Val Lys Trp
    210                 215                 220

Cys Asp Pro Leu Val Val His Ser Ser Met Glu Gln Asp Val Ala Leu
225                 230                 235                 240

Leu Arg Leu Tyr Pro Gly Ile Pro Ala Ala Leu Val Arg Ala Phe Leu
            245                 250                 255

Gln Pro Pro Leu Lys Gly Val Val Leu Glu Thr Phe Gly Ser Gly Asn
        260                 265                 270

Gly Pro Ser Lys Pro Asp Leu Leu Cys Glu Leu Arg Ala Ala Ala Glu
    275                 280                 285

Arg Gly Leu Ile Met Val Asn Cys Ser Gln Cys Leu Gln Gly Ser Val
290                 295                 300

Thr Pro Gly Tyr Ala Thr Ser Leu Ala Gly Ala Asn Ile Val Ser Gly
305                 310                 315                 320

Leu Asp Met Thr Ser Glu Ala Ala Leu Ala Lys Leu Ser Tyr Val Leu
            325                 330                 335

Gly Leu Pro Cys Leu Ser Leu Asp Arg Arg Gln Glu Leu Leu Ala Lys
        340                 345                 350

Asp Leu Arg Gly Glu Met Thr Pro Pro Ser Val Glu Glu Arg Arg Pro
    355                 360                 365

Ser

<210> SEQ ID NO 63
<211> LENGTH: 369
<212> TYPE: PRT
<213> ORGANISM: Artificial Sequence
<220> FEATURE:
<223> OTHER INFORMATION: Synthetic polypeptide

<400> SEQUENCE: 63

Met Ala Arg Ala Ser Gly Ser Glu Arg His Leu Leu Leu Ile Tyr Thr
1               5                   10                  15

Gly Gly Thr Leu Gly Met Gln Ser Lys Gly Gly Val Leu Val Pro Gly
            20                  25                  30

Pro Gly Leu Val Thr Leu Leu Arg Thr Leu Pro Met Phe His Asp Lys
        35                  40                  45

Glu Phe Ala Gln Ala Lys Gly Leu Pro Asp His Ala Leu Ala Leu Pro
    50                  55                  60

Pro Ala Ser His Gly Pro Arg Val Leu Tyr Thr Val Leu Glu Cys Gln
65                  70                  75                  80

Pro Leu Leu Asp Ser Ser Asp Met Thr Ile Lys Asp Trp Ile Arg Ile
            85                  90                  95

Ala Lys Ile Ile Glu Arg His Tyr Glu Gln Tyr Gln Gly Phe Val Val
            100                 105                 110

Ile His Gly Thr Asp Thr Met Ala Ser Gly Ala Ser Met Leu Ser Phe
        115                 120                 125

Met Leu Glu Asn Leu His Lys Pro Val Ile Leu Thr Gly Ala Gln Val
    130                 135                 140

Pro Ile Arg Val Leu Trp Asn Asp Ala Arg Glu Asn Leu Leu Gly Ala
```

```
                145                 150                 155                 160
        Leu Leu Val Ala Gly Gln Tyr Ile Ile Pro Glu Val Cys Leu Phe Met
                        165                 170                 175

Asn Ser Gln Leu Phe Arg Gly Asn Arg Val Thr Lys Val Asp Ser Gln
                        180                 185                 190

Lys Phe Glu Ala Phe Cys Ser Pro Asn Leu Ser Pro Leu Ala Thr Val
                        195                 200                 205

Gly Ala Asp Val Thr Ile Ala Trp Asp Leu Val Arg Lys Val Asp Trp
                        210                 215                 220

Lys Asp Pro Leu Val Val His Ser Asn Met Glu His Asp Val Ala Leu
        225                 230                 235                 240

Leu Arg Leu Tyr Pro Gly Ile Pro Ala Ser Leu Val Arg Ala Phe Leu
                        245                 250                 255

Gln Pro Pro Leu Lys Gly Val Val Leu Glu Thr Phe Gly Ser Gly Asn
                        260                 265                 270

Gly Pro Ser Lys Pro Asp Leu Leu Gln Glu Leu Arg Ala Ala Ala Gln
                        275                 280                 285

Arg Gly Leu Ile Met Val Asn Cys Ser Gln Cys Leu Arg Gly Ser Val
                        290                 295                 300

Thr Pro Gly Tyr Ala Thr Lys Leu Ala Gly Ala Asn Ile Val Ser Gly
        305                 310                 315                 320

Leu Asp Met Thr Ser Glu Ala Ala Leu Ala Lys Leu Ser Tyr Val Leu
                        325                 330                 335

Gly Leu Pro Glu Leu Ser Leu Glu Arg Arg Gln Glu Leu Leu Ala Lys
                        340                 345                 350

Asp Leu Arg Gly Glu Met Thr Leu Pro Thr Ala Asp Leu His Gln Ser
                        355                 360                 365

Ser

<210> SEQ ID NO 64
<211> LENGTH: 369
<212> TYPE: PRT
<213> ORGANISM: Artificial Sequence
<220> FEATURE:
<223> OTHER INFORMATION: Synthetic polypeptide

<400> SEQUENCE: 64

Met Ala Arg Ala Ser Gly Ser Glu Arg Arg Leu Leu Leu Ile Tyr Thr
        1               5                   10                  15

Gly Gly Thr Leu Gly Met Arg Ser Glu Gly Gly Val Leu Val Pro Gly
                        20                  25                  30

Pro Gly Leu Val Thr Leu Leu Arg Thr Leu Pro Met Phe His Asp Glu
                        35                  40                  45

Glu Phe Ala Arg Ala Lys Gly Leu Pro Asp His Ala Leu Ala Leu Pro
                50                  55                  60

Pro Ala Ser His Gly Pro Arg Val Leu Tyr Thr Val Leu Glu Cys Gln
        65                  70                  75                  80

Pro Leu Leu Asp Ser Ser Asp Met Thr Ile Lys Glu Trp Ile Arg Ile
                        85                  90                  95

Ala Gln Ile Ile Lys Arg His Tyr Glu Gln Tyr His Gly Phe Val Val
                        100                 105                 110

Ile His Gly Thr Asp Thr Met Ala Phe Ala Ala Ser Met Leu Ser Phe
                        115                 120                 125

Met Leu Glu Asn Leu Gln Lys Pro Val Ile Leu Thr Gly Ala Gln Val
                        130                 135                 140
```

```
Pro Ile His Val Leu Trp Asn Asp Ala Arg Glu Asn Leu Leu Gly Ala
145                 150                 155                 160

Leu Leu Val Ala Gly Gln Tyr Ile Ile Pro Glu Val Cys Leu Phe Met
            165                 170                 175

Asn Ser Gln Leu Phe Arg Gly Asn Arg Val Thr Lys Val Asp Ser Gln
                180                 185                 190

Arg Phe Glu Ala Phe Ala Ser Pro Asn Leu Ser Pro Leu Ala Thr Val
            195                 200                 205

Gly Ala Asp Val Thr Ile Ala Trp Glu Leu Val Arg Lys Val Asp Trp
        210                 215                 220

Lys Asp Pro Leu Val Val His Ser Ser Met Glu Gln Asp Val Ala Leu
225                 230                 235                 240

Leu Arg Leu Tyr Pro Gly Ile Pro Ala Ala Leu Val Arg Ala Phe Leu
                245                 250                 255

Gln Pro Pro Leu Lys Gly Val Val Leu Glu Thr Phe Gly Ser Gly Asn
                260                 265                 270

Gly Pro Ser Lys Pro Asp Leu Leu Gln Glu Leu Arg Ala Ala Ala Glu
            275                 280                 285

Arg Gly Leu Ile Met Val Asn Cys Ser Gln Cys Leu Gln Gly Ser Val
        290                 295                 300

Thr Pro Gly Tyr Ala Thr Lys Leu Ala Gly Ala Asn Ile Val Ser Gly
305                 310                 315                 320

Leu Asp Met Thr Ser Glu Ala Ala Leu Ala Lys Leu Ser Tyr Val Leu
                325                 330                 335

Gly Leu Pro Glu Leu Ser Leu Asp Arg Arg Gln Glu Leu Leu Ala Lys
                340                 345                 350

Asp Leu Arg Gly Glu Met Thr Pro Pro Ser Val Glu Gly Arg Arg Pro
            355                 360                 365

Ser

<210> SEQ ID NO 65
<211> LENGTH: 369
<212> TYPE: PRT
<213> ORGANISM: Artificial Sequence
<220> FEATURE:
<223> OTHER INFORMATION: Synthetic polypeptide

<400> SEQUENCE: 65

Met Ala Arg Ala Ser Gly Ser Glu Arg Arg Leu Leu Leu Ile Tyr Thr
1               5                   10                  15

Gly Gly Thr Leu Gly Met Arg Ser Glu Gly Gly Val Leu Val Pro Gly
            20                  25                  30

Pro Gly Leu Val Thr Leu Leu Arg Thr Leu Pro Met Phe His Asp Glu
            35                  40                  45

Glu Phe Ala Arg Ala Lys Gly Leu Ser Glu Asp Thr Leu Val Leu Pro
        50                  55                  60

Pro Ala Ser His Gly Pro Arg Val Leu Tyr Thr Val Leu Glu Cys Gln
65                  70                  75                  80

Pro Leu Leu Asp Ser Ser Asp Met Thr Ile Lys Glu Trp Ile Arg Ile
                85                  90                  95

Ala Gln Ile Ile Lys Arg His Tyr Glu Gln Tyr His Gly Phe Val Val
            100                 105                 110

Ile His Gly Thr Asp Thr Met Ala Phe Ala Ala Ser Met Leu Ser Phe
        115                 120                 125
```

```
Met Leu Glu Asn Leu Gln Lys Pro Val Ile Leu Thr Gly Ala Gln Val
    130                 135                 140

Pro Ile His Val Leu Trp Asn Asp Ala Arg Glu Asn Leu Leu Gly Ala
145                 150                 155                 160

Leu Leu Val Ala Gly Gln Tyr Ile Ile Pro Glu Val Cys Leu Phe Met
                165                 170                 175

Asn Ser Gln Leu Phe Arg Gly Asn Arg Val Thr Lys Val Asp Ser Gln
            180                 185                 190

Arg Phe Glu Ala Phe Ala Ser Pro Asn Leu Ser Pro Leu Ala Thr Val
        195                 200                 205

Gly Ala Asp Val Thr Ile Ala Trp Glu Leu Val Arg Lys Val Asp Trp
    210                 215                 220

Lys Asp Pro Leu Val Val His Ser Ser Met Glu Gln Asp Val Ala Leu
225                 230                 235                 240

Leu Arg Leu Tyr Pro Gly Ile Pro Ala Ala Leu Val Arg Ala Phe Leu
                245                 250                 255

Gln Pro Pro Leu Lys Gly Val Val Leu Glu Thr Phe Gly Ser Gly Asn
            260                 265                 270

Gly Pro Ser Lys Pro Asp Leu Leu Gln Glu Leu Arg Ala Ala Ala Glu
        275                 280                 285

Arg Gly Leu Ile Met Val Asn Cys Ser Gln Cys Leu Gln Gly Ser Val
    290                 295                 300

Thr Pro Gly Tyr Ala Thr Lys Leu Ala Gly Ala Asn Ile Val Ser Gly
305                 310                 315                 320

Leu Asp Met Thr Ser Glu Ala Ala Leu Ala Lys Leu Ser Tyr Val Leu
                325                 330                 335

Gly Leu Pro Glu Leu Ser Leu Asp Arg Arg Gln Glu Leu Leu Ala Lys
            340                 345                 350

Asp Leu Arg Gly Glu Met Thr Pro Pro Ser Val Glu Glu Arg Arg Pro
        355                 360                 365

Ser

<210> SEQ ID NO 66
<211> LENGTH: 98
<212> TYPE: PRT
<213> ORGANISM: Artificial Sequence
<220> FEATURE:
<223> OTHER INFORMATION: Synthetic polypeptide

<400> SEQUENCE: 66

Met Ser Asp Ser Glu Val Asn Gln Glu Ala Lys Pro Glu Val Lys Pro
1               5                   10                  15

Glu Val Lys Pro Glu Thr His Ile Asn Leu Lys Val Ser Asp Gly Ser
                20                  25                  30

Ser Glu Ile Phe Phe Lys Ile Lys Lys Thr Thr Pro Leu Arg Arg Leu
            35                  40                  45

Met Glu Ala Phe Ala Lys Arg Gln Gly Lys Glu Met Asp Ser Leu Arg
        50                  55                  60

Phe Leu Tyr Asp Gly Ile Arg Ile Gln Ala Asp Gln Thr Pro Glu Asp
65                  70                  75                  80

Leu Asp Met Glu Asp Asn Asp Ile Ile Glu Ala His Arg Glu Gln Ile
                85                  90                  95

Gly Gly

<210> SEQ ID NO 67
```

<211> LENGTH: 97
<212> TYPE: PRT
<213> ORGANISM: Artificial Sequence
<220> FEATURE:
<223> OTHER INFORMATION: Synthetic polypeptide

<400> SEQUENCE: 67

```
Met Ser Asp Gln Glu Ala Lys Pro Ser Thr Glu Asp Leu Gly Asp Lys
1               5                   10                  15
Lys Glu Gly Glu Tyr Ile Lys Leu Lys Val Ile Gly Gln Asp Ser Ser
            20                  25                  30
Glu Ile His Phe Lys Val Lys Met Thr Thr His Leu Lys Lys Leu Lys
        35                  40                  45
Glu Ser Tyr Cys Gln Arg Gln Gly Val Pro Met Asn Ser Leu Arg Phe
    50                  55                  60
Leu Phe Glu Gly Gln Arg Ile Ala Asp Asn His Thr Pro Lys Glu Leu
65                  70                  75                  80
Gly Met Glu Glu Glu Asp Val Ile Glu Val Tyr Gln Glu Gln Thr Gly
                85                  90                  95
Gly
```

<210> SEQ ID NO 68
<211> LENGTH: 95
<212> TYPE: PRT
<213> ORGANISM: Artificial Sequence
<220> FEATURE:
<223> OTHER INFORMATION: Synthetic polypeptide

<400> SEQUENCE: 68

```
Met Ala Asp Glu Lys Pro Lys Glu Gly Val Lys Thr Glu Asn Asn Asp
1               5                   10                  15
His Ile Asn Leu Lys Val Ala Gly Gln Asp Gly Ser Val Val Gln Phe
            20                  25                  30
Lys Ile Lys Arg His Thr Pro Leu Ser Lys Leu Met Lys Ala Tyr Cys
        35                  40                  45
Glu Arg Gln Gly Leu Ser Met Arg Gln Ile Arg Phe Arg Phe Asp Gly
    50                  55                  60
Gln Pro Ile Asn Glu Thr Asp Thr Pro Ala Gln Leu Glu Met Glu Asp
65                  70                  75                  80
Glu Asp Thr Ile Asp Val Phe Gln Gln Gln Thr Gly Gly Val Tyr
                85                  90                  95
```

<210> SEQ ID NO 69
<211> LENGTH: 103
<212> TYPE: PRT
<213> ORGANISM: Artificial Sequence
<220> FEATURE:
<223> OTHER INFORMATION: Synthetic polypeptide

<400> SEQUENCE: 69

```
Met Ser Glu Glu Lys Pro Lys Glu Gly Val Lys Thr Glu Asn Asp His
1               5                   10                  15
Ile Asn Leu Lys Val Ala Gly Gln Asp Gly Ser Val Val Gln Phe Lys
            20                  25                  30
Ile Lys Arg His Thr Pro Leu Ser Lys Leu Met Lys Ala Tyr Cys Glu
        35                  40                  45
Arg Gln Gly Leu Ser Met Arg Gln Ile Arg Phe Arg Phe Asp Gly Gln
    50                  55                  60
Pro Ile Asn Glu Thr Asp Thr Pro Ala Gln Leu Glu Met Glu Asp Glu
```

```
                65                  70                  75                  80
Asp Thr Ile Asp Val Phe Gln Gln Thr Gly Gly Val Pro Glu Ser
                    85                  90                  95

Ser Leu Ala Gly His Ser Phe
                100

<210> SEQ ID NO 70
<211> LENGTH: 95
<212> TYPE: PRT
<213> ORGANISM: Artificial Sequence
<220> FEATURE:
<223> OTHER INFORMATION: Synthetic polypeptide

<400> SEQUENCE: 70

Met Ala Asn Glu Lys Pro Thr Glu Val Lys Thr Glu Asn Asn Asn
1               5                   10                  15

His Ile Asn Leu Lys Val Ala Gly Gln Asp Gly Ser Val Val Gln Phe
                20                  25                  30

Lys Ile Lys Arg Gln Thr Pro Leu Ser Lys Leu Met Lys Ala Tyr Cys
                35                  40                  45

Glu Pro Arg Gly Leu Ser Met Lys Gln Ile Arg Phe Arg Phe Gly Gly
                50                  55                  60

Gln Pro Ile Ser Gly Thr Asp Lys Pro Ala Gln Leu Glu Met Glu Asp
65                  70                  75                  80

Glu Asp Thr Ile Asp Val Phe Gln Gln Pro Thr Gly Gly Val Tyr
                    85                  90                  95

<210> SEQ ID NO 71
<211> LENGTH: 20
<212> TYPE: PRT
<213> ORGANISM: Artificial Sequence
<220> FEATURE:
<223> OTHER INFORMATION: Synthetic peptide

<400> SEQUENCE: 71

Gln Arg Leu Ile Glu Asp Ile Cys Leu Pro Arg Trp Gly Cys Leu Trp
1               5                   10                  15

Glu Asp Asp Phe
            20

<210> SEQ ID NO 72
<211> LENGTH: 18
<212> TYPE: PRT
<213> ORGANISM: Artificial Sequence
<220> FEATURE:
<223> OTHER INFORMATION: Synthetic peptide

<400> SEQUENCE: 72

Arg Leu Ile Glu Asp Ile Cys Leu Pro Arg Trp Gly Cys Leu Trp Glu
1               5                   10                  15

Asp Asp

<210> SEQ ID NO 73
<211> LENGTH: 15
<212> TYPE: PRT
<213> ORGANISM: Artificial Sequence
<220> FEATURE:
<223> OTHER INFORMATION: Synthetic peptide

<400> SEQUENCE: 73

Arg Leu Ile Glu Asp Ile Cys Leu Pro Arg Trp Gly Cys Leu Trp
1               5                   10                  15
```

<210> SEQ ID NO 74
<211> LENGTH: 468
<212> TYPE: PRT
<213> ORGANISM: Artificial Sequence
<220> FEATURE:
<223> OTHER INFORMATION: Synthetic polypeptide

<400> SEQUENCE: 74

```
Met Ser Asp Ser Glu Val Asn Gln Glu Ala Lys Pro Glu Val Lys Pro
1               5                   10                  15

Glu Val Lys Pro Glu Thr His Ile Asn Leu Lys Val Ser Asp Gly Ser
            20                  25                  30

Ser Glu Ile Phe Phe Lys Ile Lys Lys Thr Thr Pro Leu Arg Arg Leu
        35                  40                  45

Met Glu Ala Phe Ala Lys Arg Gln Gly Lys Glu Met Asp Ser Leu Arg
    50                  55                  60

Phe Leu Tyr Asp Gly Ile Arg Ile Gln Ala Asp Gln Thr Pro Glu Asp
65                  70                  75                  80

Leu Asp Met Glu Asp Asn Asp Ile Ile Glu Ala His Arg Glu Gln Ile
                85                  90                  95

Gly Gly His Met Ala Arg Ala Ser Gly Ser Glu Arg His Leu Leu Leu
            100                 105                 110

Ile Tyr Thr Gly Gly Thr Leu Gly Met Gln Ser Lys Gly Gly Val Leu
        115                 120                 125

Val Pro Gly Pro Gly Leu Val Thr Leu Leu Arg Thr Leu Pro Met Phe
    130                 135                 140

His Asp Lys Glu Phe Ala Gln Ala Gln Gly Leu Pro Asp His Ala Leu
145                 150                 155                 160

Ala Leu Pro Pro Ala Ser His Gly Pro Arg Val Leu Tyr Thr Val Leu
                165                 170                 175

Glu Lys Gln Pro Leu Leu Asp Ser Ser Asp Met Thr Ile Asp Asp Trp
            180                 185                 190

Ile Arg Ile Ala Lys Ile Ile Glu Arg His Tyr Glu Gln Tyr Gln Gly
        195                 200                 205

Phe Val Val Ile His Gly Thr Asp Thr Met Ala Ser Gly Ala Ser Met
    210                 215                 220

Leu Ser Phe Met Leu Glu Asn Leu His Lys Pro Val Ile Leu Thr Gly
225                 230                 235                 240

Ala Gln Val Pro Ile Arg Val Leu Trp Asn Asp Ala Arg Glu Asn Leu
                245                 250                 255

Leu Gly Ala Leu Leu Val Ala Gly Gln Tyr Ile Ile Pro Glu Val Cys
            260                 265                 270

Leu Phe Met Asn Ser Gln Leu Phe Arg Gly Asn Arg Val Thr Lys Val
        275                 280                 285

Asp Ser Gln Lys Phe Glu Ala Phe Ala Ser Pro Asn Leu Ser Pro Leu
    290                 295                 300

Ala Thr Val Gly Ala Asp Val Thr Ile Ala Trp Asp Leu Val Arg Lys
305                 310                 315                 320

Val Lys Trp Lys Asp Pro Leu Val Val His Ser Asn Met Glu His Asp
                325                 330                 335

Val Ala Leu Leu Arg Leu Tyr Pro Gly Ile Pro Ala Ser Leu Val Arg
            340                 345                 350

Ala Phe Leu Gln Pro Pro Leu Lys Gly Val Val Leu Glu Thr Phe Gly
        355                 360                 365
```

Ser Gly Asn Gly Pro Ser Lys Pro Asp Leu Leu Gln Glu Leu Arg Ala
          370                 375                 380

Ala Ala Gln Arg Gly Leu Ile Met Val Asn Cys Ser Gln Cys Leu Arg
385                 390                 395                 400

Gly Ser Val Thr Pro Gly Tyr Ala Thr Ser Leu Ala Gly Ala Asn Ile
                405                 410                 415

Val Ser Gly Leu Asp Met Thr Ser Glu Ala Ala Leu Ala Lys Leu Ser
            420                 425                 430

Tyr Val Leu Gly Leu Pro Glu Leu Ser Leu Glu Arg Arg Gln Glu Leu
            435                 440                 445

Leu Ala Lys Asp Leu Arg Gly Glu Met Thr Leu Pro Thr Ala Asp Leu
450                 455                 460

His Gln Ser Ser
465

<210> SEQ ID NO 75
<211> LENGTH: 467
<212> TYPE: PRT
<213> ORGANISM: Artificial Sequence
<220> FEATURE:
<223> OTHER INFORMATION: Synthetic polypeptide

<400> SEQUENCE: 75

Met Ser Asp Gln Glu Ala Lys Pro Ser Thr Glu Asp Leu Gly Asp Lys
1               5                   10                  15

Lys Glu Gly Glu Tyr Ile Lys Leu Lys Val Ile Gly Gln Asp Ser Ser
                20                  25                  30

Glu Ile His Phe Lys Val Lys Met Thr Thr His Leu Lys Lys Leu Lys
            35                  40                  45

Glu Ser Tyr Cys Gln Arg Gln Gly Val Pro Met Asn Ser Leu Arg Phe
        50                  55                  60

Leu Phe Glu Gly Gln Arg Ile Ala Asp Asn His Thr Pro Lys Glu Leu
65                  70                  75                  80

Gly Met Glu Glu Glu Asp Val Ile Glu Val Tyr Gln Glu Gln Thr Gly
                85                  90                  95

Gly His Met Ala Arg Ala Ser Gly Ser Glu Arg His Leu Leu Leu Ile
            100                 105                 110

Tyr Thr Gly Gly Thr Leu Gly Met Gln Ser Lys Gly Gly Val Leu Val
        115                 120                 125

Pro Gly Pro Gly Leu Val Thr Leu Leu Arg Thr Leu Pro Met Phe His
130                 135                 140

Asp Lys Glu Phe Ala Gln Ala Gln Gly Leu Pro Asp His Ala Leu Ala
145                 150                 155                 160

Leu Pro Pro Ala Ser His Gly Pro Arg Val Leu Tyr Thr Val Leu Glu
                165                 170                 175

Lys Gln Pro Leu Leu Asp Ser Ser Asp Met Thr Ile Asp Asp Trp Ile
            180                 185                 190

Arg Ile Ala Lys Ile Ile Glu Arg His Tyr Glu Gln Tyr Gln Gly Phe
        195                 200                 205

Val Val Ile His Gly Thr Asp Thr Met Ala Ser Gly Ala Ser Met Leu
    210                 215                 220

Ser Phe Met Leu Glu Asn Leu His Lys Pro Val Ile Leu Thr Gly Ala
225                 230                 235                 240

Gln Val Pro Ile Arg Val Leu Trp Asn Asp Ala Arg Glu Asn Leu Leu
                245                 250                 255

```
Gly Ala Leu Leu Val Ala Gly Gln Tyr Ile Ile Pro Glu Val Cys Leu
            260                 265                 270

Phe Met Asn Ser Gln Leu Phe Arg Gly Asn Arg Val Thr Lys Val Asp
        275                 280                 285

Ser Gln Lys Phe Glu Ala Phe Ala Ser Pro Asn Leu Ser Pro Leu Ala
        290                 295                 300

Thr Val Gly Ala Asp Val Thr Ile Ala Trp Asp Leu Val Arg Lys Val
305                 310                 315                 320

Lys Trp Lys Asp Pro Leu Val Val His Ser Asn Met Glu His Asp Val
                325                 330                 335

Ala Leu Leu Arg Leu Tyr Pro Gly Ile Pro Ala Ser Leu Val Arg Ala
            340                 345                 350

Phe Leu Gln Pro Pro Leu Lys Gly Val Val Leu Glu Thr Phe Gly Ser
        355                 360                 365

Gly Asn Gly Pro Ser Lys Pro Asp Leu Leu Gln Glu Leu Arg Ala Ala
    370                 375                 380

Ala Gln Arg Gly Leu Ile Met Val Asn Cys Ser Gln Cys Leu Arg Gly
385                 390                 395                 400

Ser Val Thr Pro Gly Tyr Ala Thr Ser Leu Ala Gly Ala Asn Ile Val
                405                 410                 415

Ser Gly Leu Asp Met Thr Ser Glu Ala Ala Leu Ala Lys Leu Ser Tyr
            420                 425                 430

Val Leu Gly Leu Pro Glu Leu Ser Leu Glu Arg Arg Gln Glu Leu Leu
        435                 440                 445

Ala Lys Asp Leu Arg Gly Glu Met Thr Leu Pro Thr Ala Asp Leu His
    450                 455                 460

Gln Ser Ser
465

<210> SEQ ID NO 76
<211> LENGTH: 386
<212> TYPE: PRT
<213> ORGANISM: Artificial Sequence
<220> FEATURE:
<223> OTHER INFORMATION: Synthetic polypeptide

<400> SEQUENCE: 76

Arg Leu Ile Glu Asp Ile Cys Leu Pro Arg Trp Gly Cys Leu Trp Glu
1               5                   10                  15

Asp Asp Ala Arg Ala Ser Gly Ser Glu Arg His Leu Leu Leu Ile Tyr
            20                  25                  30

Thr Gly Gly Thr Leu Gly Met Gln Ser Lys Gly Gly Val Leu Val Pro
        35                  40                  45

Gly Pro Gly Leu Val Thr Leu Leu Arg Thr Leu Pro Met Phe His Asp
    50                  55                  60

Lys Glu Phe Ala Gln Ala Gln Gly Leu Pro Asp His Ala Leu Ala Leu
65                  70                  75                  80

Pro Pro Ala Ser His Gly Pro Arg Val Leu Tyr Thr Val Leu Glu Cys
                85                  90                  95

Gln Pro Leu Leu Asp Ser Ser Asp Met Thr Ile Asp Asp Trp Ile Arg
            100                 105                 110

Ile Ala Lys Ile Ile Glu Arg His Tyr Glu Gln Tyr Gln Gly Phe Val
        115                 120                 125

Val Ile His Gly Thr Asp Thr Met Ala Ser Gly Ala Ser Met Leu Ser
    130                 135                 140
```

```
Phe Met Leu Glu Asn Leu His Lys Pro Val Ile Leu Thr Gly Ala Gln
145                 150                 155                 160

Val Pro Ile Arg Val Leu Trp Asn Asp Ala Arg Glu Asn Leu Leu Gly
            165                 170                 175

Ala Leu Leu Val Ala Gly Gln Tyr Ile Ile Pro Glu Val Cys Leu Phe
        180                 185                 190

Met Asn Ser Gln Leu Phe Arg Gly Asn Arg Val Thr Lys Val Asp Ser
    195                 200                 205

Gln Lys Phe Glu Ala Phe Ala Ser Pro Asn Leu Ser Pro Leu Ala Thr
    210                 215                 220

Val Gly Ala Asp Val Thr Ile Ala Trp Asp Leu Val Arg Lys Val Lys
225                 230                 235                 240

Trp Lys Asp Pro Leu Val Val His Ser Asn Met Glu His Asp Val Ala
            245                 250                 255

Leu Leu Arg Leu Tyr Pro Gly Ile Pro Ala Ser Leu Val Arg Ala Phe
        260                 265                 270

Leu Gln Pro Pro Leu Lys Gly Val Val Leu Glu Thr Phe Gly Ser Gly
    275                 280                 285

Asn Gly Pro Ser Lys Pro Asp Leu Leu Gln Glu Leu Arg Ala Ala Ala
290                 295                 300

Gln Arg Gly Leu Ile Met Val Asn Cys Ser Gln Cys Leu Arg Gly Ser
305                 310                 315                 320

Val Thr Pro Gly Tyr Ala Thr Ser Leu Ala Gly Ala Asn Ile Val Ser
            325                 330                 335

Gly Leu Asp Met Thr Ser Glu Ala Leu Ala Lys Leu Ser Tyr Val
        340                 345                 350

Leu Gly Leu Pro Glu Leu Ser Leu Glu Arg Arg Gln Glu Leu Leu Ala
    355                 360                 365

Lys Asp Leu Arg Gly Glu Met Thr Leu Pro Thr Ala Asp Leu His Gln
    370                 375                 380

Ser Ser
385

<210> SEQ ID NO 77
<211> LENGTH: 387
<212> TYPE: PRT
<213> ORGANISM: Artificial Sequence
<220> FEATURE:
<223> OTHER INFORMATION: Synthetic polypeptide

<400> SEQUENCE: 77

Met Ala Arg Ala Ser Gly Ser Glu Arg His Leu Leu Leu Ile Tyr Thr
1               5                   10                  15

Gly Gly Thr Leu Gly Met Gln Ser Lys Gly Gly Val Leu Val Pro Gly
            20                  25                  30

Pro Gly Leu Val Thr Leu Leu Arg Thr Leu Pro Met Phe His Asp Lys
        35                  40                  45

Glu Phe Ala Gln Ala Gln Gly Leu Pro Asp His Ala Leu Ala Leu Pro
    50                  55                  60

Pro Ala Ser His Gly Pro Arg Val Leu Tyr Thr Val Leu Glu Cys Gln
65                  70                  75                  80

Pro Leu Leu Asp Ser Ser Asp Met Thr Ile Asp Asp Trp Ile Arg Ile
            85                  90                  95

Ala Lys Ile Ile Glu Arg His Tyr Glu Gln Tyr Gln Gly Phe Val Val
        100                 105                 110
```

```
Ile His Gly Thr Asp Thr Met Ala Ser Gly Ala Ser Met Leu Ser Phe
        115                 120                 125

Met Leu Glu Asn Leu His Lys Pro Val Ile Leu Thr Gly Ala Gln Val
    130                 135                 140

Pro Ile Arg Val Leu Trp Asn Asp Ala Arg Glu Asn Leu Leu Gly Ala
145                 150                 155                 160

Leu Leu Val Ala Gly Gln Tyr Ile Ile Pro Glu Val Cys Leu Phe Met
                165                 170                 175

Asn Ser Gln Leu Phe Arg Gly Asn Arg Val Thr Lys Val Asp Ser Gln
            180                 185                 190

Lys Phe Glu Ala Phe Ala Ser Pro Asn Leu Ser Pro Leu Ala Thr Val
        195                 200                 205

Gly Ala Asp Val Thr Ile Ala Trp Asp Leu Val Arg Lys Val Lys Trp
    210                 215                 220

Lys Asp Pro Leu Val Val His Ser Asn Met Glu His Asp Val Ala Leu
225                 230                 235                 240

Leu Arg Leu Tyr Pro Gly Ile Pro Ala Ser Leu Val Arg Ala Phe Leu
                245                 250                 255

Gln Pro Pro Leu Lys Gly Val Val Leu Glu Thr Phe Gly Ser Gly Asn
            260                 265                 270

Gly Pro Ser Lys Pro Asp Leu Leu Gln Glu Leu Arg Ala Ala Ala Gln
        275                 280                 285

Arg Gly Leu Ile Met Val Asn Cys Ser Gln Cys Leu Arg Gly Ser Val
    290                 295                 300

Thr Pro Gly Tyr Ala Thr Ser Leu Ala Gly Ala Asn Ile Val Ser Gly
305                 310                 315                 320

Leu Asp Met Thr Ser Glu Ala Ala Leu Ala Lys Leu Ser Tyr Val Leu
                325                 330                 335

Gly Leu Pro Glu Leu Ser Leu Glu Arg Arg Gln Glu Leu Leu Ala Lys
            340                 345                 350

Asp Leu Arg Gly Glu Met Thr Leu Pro Thr Ala Asp Leu His Gln Ser
        355                 360                 365

Ser Arg Leu Ile Glu Asp Ile Cys Leu Pro Arg Trp Gly Cys Leu Trp
    370                 375                 380

Glu Asp Asp
385

<210> SEQ ID NO 78
<211> LENGTH: 486
<212> TYPE: PRT
<213> ORGANISM: Artificial Sequence
<220> FEATURE:
<223> OTHER INFORMATION: Synthetic polypeptide

<400> SEQUENCE: 78

Met Ser Asp Ser Glu Val Asn Gln Glu Ala Lys Pro Glu Val Lys Pro
1               5                   10                  15

Glu Val Lys Pro Glu Thr His Ile Asn Leu Lys Val Ser Asp Gly Ser
            20                  25                  30

Ser Glu Ile Phe Phe Lys Ile Lys Lys Thr Thr Pro Leu Arg Arg Leu
        35                  40                  45

Met Glu Ala Phe Ala Lys Arg Gln Gly Lys Glu Met Asp Ser Leu Arg
    50                  55                  60

Phe Leu Tyr Asp Gly Ile Arg Ile Gln Ala Asp Gln Thr Pro Glu Asp
65                  70                  75                  80
```

```
Leu Asp Met Glu Asp Asn Asp Ile Ile Glu Ala His Arg Glu Gln Ile
                85                  90                  95
Gly Gly His Met Ala Arg Ala Ser Gly Ser Glu Arg His Leu Leu Leu
            100                 105                 110
Ile Tyr Thr Gly Gly Thr Leu Gly Met Gln Ser Lys Gly Gly Val Leu
        115                 120                 125
Val Pro Gly Pro Gly Leu Val Thr Leu Leu Arg Thr Leu Pro Met Phe
130                 135                 140
His Asp Lys Glu Phe Ala Gln Ala Gln Gly Leu Pro Asp His Ala Leu
145                 150                 155                 160
Ala Leu Pro Pro Ala Ser His Gly Pro Arg Val Leu Tyr Thr Val Leu
                165                 170                 175
Glu Cys Gln Pro Leu Leu Asp Ser Ser Asp Met Thr Ile Asp Asp Trp
            180                 185                 190
Ile Arg Ile Ala Lys Ile Ile Glu Arg His Tyr Glu Gln Tyr Gln Gly
        195                 200                 205
Phe Val Val Ile His Gly Thr Asp Thr Met Ala Ser Gly Ala Ser Met
210                 215                 220
Leu Ser Phe Met Leu Glu Asn Leu His Lys Pro Val Ile Leu Thr Gly
225                 230                 235                 240
Ala Gln Val Pro Ile Arg Val Leu Trp Asn Asp Ala Arg Glu Asn Leu
                245                 250                 255
Leu Gly Ala Leu Leu Val Ala Gly Gln Tyr Ile Ile Pro Glu Val Cys
            260                 265                 270
Leu Phe Met Asn Ser Gln Leu Phe Arg Gly Asn Arg Val Thr Lys Val
        275                 280                 285
Asp Ser Gln Lys Phe Glu Ala Phe Ala Ser Pro Asn Leu Ser Pro Leu
290                 295                 300
Ala Thr Val Gly Ala Asp Val Thr Ile Ala Trp Asp Leu Val Arg Lys
305                 310                 315                 320
Val Lys Trp Lys Asp Pro Leu Val Val His Ser Asn Met Glu His Asp
                325                 330                 335
Val Ala Leu Leu Arg Leu Tyr Pro Gly Ile Pro Ala Ser Leu Val Arg
            340                 345                 350
Ala Phe Leu Gln Pro Pro Leu Lys Gly Val Val Leu Glu Thr Phe Gly
        355                 360                 365
Ser Gly Asn Gly Pro Ser Lys Pro Asp Leu Leu Gln Glu Leu Arg Ala
370                 375                 380
Ala Ala Gln Arg Gly Leu Ile Met Val Asn Cys Ser Gln Cys Leu Arg
385                 390                 395                 400
Gly Ser Val Thr Pro Gly Tyr Ala Thr Ser Leu Ala Gly Ala Asn Ile
                405                 410                 415
Val Ser Gly Leu Asp Met Thr Ser Glu Ala Leu Ala Lys Leu Ser
            420                 425                 430
Tyr Val Leu Gly Leu Pro Glu Leu Ser Leu Glu Arg Gln Glu Leu
        435                 440                 445
Leu Ala Lys Asp Leu Arg Gly Glu Met Thr Leu Pro Thr Ala Asp Leu
450                 455                 460
His Gln Ser Ser Arg Leu Ile Glu Asp Ile Cys Leu Pro Arg Trp Gly
465                 470                 475                 480
Cys Leu Trp Glu Asp Asp
                485
```

<210> SEQ ID NO 79
<211> LENGTH: 485
<212> TYPE: PRT
<213> ORGANISM: Artificial Sequence
<220> FEATURE:
<223> OTHER INFORMATION: Synthetic polypeptide

<400> SEQUENCE: 79

```
Met Ser Asp Gln Glu Ala Lys Pro Ser Thr Glu Asp Leu Gly Asp Lys
1               5                   10                  15

Lys Glu Gly Glu Tyr Ile Lys Leu Lys Val Ile Gly Gln Asp Ser Ser
            20                  25                  30

Glu Ile His Phe Lys Val Lys Met Thr Thr His Leu Lys Lys Leu Lys
        35                  40                  45

Glu Ser Tyr Cys Gln Arg Gln Gly Val Pro Met Asn Ser Leu Arg Phe
    50                  55                  60

Leu Phe Glu Gly Gln Arg Ile Ala Asp Asn His Thr Pro Lys Glu Leu
65                  70                  75                  80

Gly Met Glu Glu Glu Asp Val Ile Glu Val Tyr Gln Glu Gln Thr Gly
                85                  90                  95

Gly His Met Ala Arg Ala Ser Gly Ser Glu Arg His Leu Leu Leu Ile
            100                 105                 110

Tyr Thr Gly Gly Thr Leu Gly Met Gln Ser Lys Gly Gly Val Leu Val
        115                 120                 125

Pro Gly Pro Gly Leu Val Thr Leu Leu Arg Thr Leu Pro Met Phe His
    130                 135                 140

Asp Lys Glu Phe Ala Gln Ala Gln Gly Leu Pro Asp His Ala Leu Ala
145                 150                 155                 160

Leu Pro Pro Ala Ser His Gly Pro Arg Val Leu Tyr Thr Val Leu Glu
                165                 170                 175

Cys Gln Pro Leu Leu Asp Ser Ser Asp Met Thr Ile Asp Asp Trp Ile
            180                 185                 190

Arg Ile Ala Lys Ile Ile Glu Arg His Tyr Glu Gln Tyr Gln Gly Phe
        195                 200                 205

Val Val Ile His Gly Thr Asp Thr Met Ala Ser Gly Ala Ser Met Leu
    210                 215                 220

Ser Phe Met Leu Glu Asn Leu His Lys Pro Val Ile Leu Thr Gly Ala
225                 230                 235                 240

Gln Val Pro Ile Arg Val Leu Trp Asn Asp Ala Arg Glu Asn Leu Leu
                245                 250                 255

Gly Ala Leu Leu Val Ala Gly Gln Tyr Ile Ile Pro Glu Val Cys Leu
            260                 265                 270

Phe Met Asn Ser Gln Leu Phe Arg Gly Asn Arg Val Thr Lys Val Asp
        275                 280                 285

Ser Gln Lys Phe Glu Ala Phe Ala Ser Pro Asn Leu Ser Pro Leu Ala
    290                 295                 300

Thr Val Gly Ala Asp Val Thr Ile Ala Trp Asp Leu Val Arg Lys Val
305                 310                 315                 320

Lys Trp Lys Asp Pro Leu Val Val His Ser Asn Met Glu His Asp Val
                325                 330                 335

Ala Leu Leu Arg Leu Tyr Pro Gly Ile Pro Ala Ser Leu Val Arg Ala
            340                 345                 350

Phe Leu Gln Pro Pro Leu Lys Gly Val Val Leu Glu Thr Phe Gly Ser
        355                 360                 365
```

Gly Asn Gly Pro Ser Lys Pro Asp Leu Leu Gln Glu Leu Arg Ala Ala
            370                 375                 380

Ala Gln Arg Gly Leu Ile Met Val Asn Cys Ser Gln Cys Leu Arg Gly
385                 390                 395                 400

Ser Val Thr Pro Gly Tyr Ala Thr Ser Leu Ala Gly Ala Asn Ile Val
                405                 410                 415

Ser Gly Leu Asp Met Thr Ser Glu Ala Ala Leu Ala Lys Leu Ser Tyr
            420                 425                 430

Val Leu Gly Leu Pro Glu Leu Ser Leu Glu Arg Arg Gln Glu Leu Leu
            435                 440                 445

Ala Lys Asp Leu Arg Gly Glu Met Thr Leu Pro Thr Ala Asp Leu His
    450                 455                 460

Gln Ser Ser Arg Leu Ile Glu Asp Ile Cys Leu Pro Arg Trp Gly Cys
465                 470                 475                 480

Leu Trp Glu Asp Asp
            485

<210> SEQ ID NO 80
<211> LENGTH: 167
<212> TYPE: PRT
<213> ORGANISM: Artificial Sequence
<220> FEATURE:
<223> OTHER INFORMATION: Synthetic polypeptide

<400> SEQUENCE: 80

Arg Glu Arg Gly Pro Gln Arg Val Ala Ala His Ile Thr Gly Thr Arg
1               5                   10                  15

Gly Arg Ser Asn Thr Leu Ser Ser Pro Asn Ser Lys Asn Glu Lys Ala
            20                  25                  30

Leu Gly Arg Lys Ile Asn Ser Trp Glu Ser Ser Arg Ser Gly His Ser
        35                  40                  45

Phe Leu Ser Asn Leu His Leu Arg Asn Gly Glu Leu Val Ile His Glu
    50                  55                  60

Lys Gly Phe Tyr Tyr Ile Tyr Ser Gln Thr Tyr Phe Arg Phe Gln Glu
65                  70                  75                  80

Glu Ile Lys Glu Asn Thr Lys Asn Asp Lys Gln Met Val Gln Tyr Ile
                85                  90                  95

Tyr Lys Tyr Thr Ser Tyr Pro Asp Pro Ile Leu Leu Met Lys Ser Ala
            100                 105                 110

Arg Asn Ser Cys Trp Ser Lys Asp Ala Glu Tyr Gly Leu Tyr Ser Ile
        115                 120                 125

Tyr Gln Gly Gly Ile Phe Glu Leu Lys Glu Asn Asp Arg Ile Phe Val
    130                 135                 140

Ser Val Thr Asn Glu His Leu Ile Asp Met Asp His Glu Ala Ser Phe
145                 150                 155                 160

Phe Gly Ala Phe Leu Val Gly
            165

<210> SEQ ID NO 81
<211> LENGTH: 16
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (5)..(16)
<223> OTHER INFORMATION: Residue may be present or absent

```
<400> SEQUENCE: 81

Gly Gly Gly Ser Gly Gly Gly Ser Gly Gly Gly Ser Gly Gly Gly Ser
1               5                   10                  15

<210> SEQ ID NO 82
<211> LENGTH: 24
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (10)..(24)
<223> OTHER INFORMATION: Residue may be present or absent

<400> SEQUENCE: 82

Gly Gly Gly Ser Gly Gly Gly Ser Gly Gly Gly Ser Gly Gly Gly Gly
1               5                   10                  15

Gly Gly Ser Gly Gly Gly Gly Ser
            20

<210> SEQ ID NO 83
<211> LENGTH: 24
<212> TYPE: PRT
<213> ORGANISM: Artificial Sequence
<220> FEATURE:
<223> OTHER INFORMATION: Synthetic peptide

<400> SEQUENCE: 83

Gly Gly Gly Ser Gly Gly Gly Ser Gly Gly Gly Ser Gly Gly Gly Gly
1               5                   10                  15

Gly Gly Ser Gly Gly Gly Gly Ser
            20

<210> SEQ ID NO 84
<211> LENGTH: 19
<212> TYPE: PRT
<213> ORGANISM: Artificial Sequence
<220> FEATURE:
<223> OTHER INFORMATION: Synthetic peptide

<400> SEQUENCE: 84

Ser Gly Ser Gly Ser Gly Ser Gly Ser Gly Ser Gly Ser Gly Ser Gly
1               5                   10                  15

Ser Gly Ser

<210> SEQ ID NO 85
<211> LENGTH: 27
<212> TYPE: PRT
<213> ORGANISM: Artificial Sequence
<220> FEATURE:
<223> OTHER INFORMATION: Synthetic peptide

<400> SEQUENCE: 85

Gly Tyr Ile Pro Glu Ala Pro Arg Asp Gly Gln Ala Tyr Val Arg Lys
1               5                   10                  15

Asp Gly Glu Trp Val Leu Leu Ser Thr Phe Leu
            20                  25

<210> SEQ ID NO 86
<211> LENGTH: 369
<212> TYPE: PRT
<213> ORGANISM: Artificial Sequence
<220> FEATURE:
<223> OTHER INFORMATION: Synthetic polypeptide
```

<400> SEQUENCE: 86

```
Met Ala Arg Ala Ser Gly Lys Glu Arg Arg Leu Leu Leu Ile Tyr Thr
1               5                   10                  15
Gly Gly Thr Leu Gly Met Arg Ser Glu Gly Val Leu Val Pro Gly
                20                  25                  30
Pro Gly Leu Val Thr Leu Leu Arg Thr Leu Pro Met Phe His Asp Glu
            35                  40                  45
Glu Phe Ala Arg Lys Lys Gly Leu Lys Lys Asp Thr Leu Val Leu Pro
50                  55                  60
Pro Ala Ser His Gly Pro Arg Val Leu Tyr Thr Val Leu Glu Cys Gln
65                  70                  75                  80
Pro Leu Leu Asp Ser Ser Asp Met Thr Ile Ala Glu Trp Ile Arg Ile
                85                  90                  95
Ala Lys Ile Ile Lys Arg His Tyr Glu Lys Tyr His Gly Phe Val Val
                100                 105                 110
Ile His Gly Thr Asp Thr Met Ala Phe Ala Ala Ser Met Leu Ser Phe
            115                 120                 125
Met Leu Glu Asn Leu Gln Lys Pro Val Ile Leu Thr Gly Ala Gln Val
130                 135                 140
Pro Ile His Val Leu Trp Asn Asp Ala Arg Glu Asn Leu Leu Gly Ala
145                 150                 155                 160
Leu Leu Val Ala Gly Gln Tyr Ile Ile Pro Glu Val Cys Leu Phe Met
                165                 170                 175
Asn Ser Gln Leu Phe Arg Gly Asn Arg Val Thr Lys Val Asp Ser Gln
            180                 185                 190
Arg Phe Glu Ala Phe Ala Ser Pro Asn Leu Ser Pro Leu Ala Thr Val
        195                 200                 205
Gly Ala Asp Val Thr Ile Ala Trp Glu Leu Val Arg Lys Val Lys Trp
    210                 215                 220
Lys Asp Pro Leu Val Val His Ser Lys Met Glu Gln Asp Val Ala Leu
225                 230                 235                 240
Leu Arg Leu Tyr Pro Gly Ile Pro Ala Lys Leu Val Arg Ala Phe Leu
                245                 250                 255
Lys Pro Pro Leu Lys Gly Val Val Leu Glu Thr Phe Gly Ser Gly Asn
            260                 265                 270
Gly Pro Ser Lys Pro Asp Leu Leu Lys Glu Leu Arg Ala Ala Ala Glu
        275                 280                 285
Arg Gly Leu Ile Met Val Asn Cys Ser Gln Cys Leu Gln Gly Ser Val
    290                 295                 300
Thr Pro Gly Tyr Ala Thr Lys Leu Ala Gly Ala Asn Ile Val Ser Gly
305                 310                 315                 320
Leu Asp Met Thr Ser Glu Ala Ala Leu Ala Lys Leu Ser Tyr Val Leu
                325                 330                 335
Gly Leu Pro Lys Leu Ser Leu Asp Arg Arg Gln Glu Leu Leu Ala Lys
            340                 345                 350
Asp Leu Arg Gly Glu Met Thr Pro Pro Ser Val Glu Glu Arg Arg Pro
        355                 360                 365
Ser
```

<210> SEQ ID NO 87
<211> LENGTH: 503
<212> TYPE: PRT
<213> ORGANISM: Artificial Sequence
<220> FEATURE:
<223> OTHER INFORMATION: Synthetic polypeptide

<400> SEQUENCE: 87

```
Arg Glu Arg Gly Pro Gln Arg Val Ala Ala His Ile Thr Gly Thr Arg
1               5                   10                  15

Gly Arg Ser Asn Thr Leu Ser Ser Pro Asn Ser Lys Asn Glu Lys Ala
            20                  25                  30

Leu Gly Arg Lys Ile Asn Ser Trp Glu Ser Ser Arg Ser Gly His Ser
        35                  40                  45

Phe Leu Ser Asn Leu His Leu Arg Asn Gly Glu Leu Val Ile His Glu
    50                  55                  60

Lys Gly Phe Tyr Tyr Ile Tyr Ser Gln Thr Tyr Phe Arg Phe Gln Glu
65                  70                  75                  80

Glu Ile Lys Glu Asn Thr Lys Asn Asp Lys Gln Met Val Gln Tyr Ile
                85                  90                  95

Tyr Lys Tyr Thr Ser Tyr Pro Asp Pro Ile Leu Leu Met Lys Ser Ala
            100                 105                 110

Arg Asn Ser Cys Trp Ser Lys Asp Ala Glu Tyr Gly Leu Tyr Ser Ile
        115                 120                 125

Tyr Gln Gly Gly Ile Phe Glu Leu Lys Glu Asn Asp Arg Ile Phe Val
    130                 135                 140

Ser Val Thr Asn Glu His Leu Ile Asp Met Asp His Glu Ala Ser Phe
145                 150                 155                 160

Phe Gly Ala Phe Leu Val Gly Gly Arg Glu Arg Gly Pro Gln Arg Val
                165                 170                 175

Ala Ala His Ile Thr Gly Thr Arg Gly Arg Ser Asn Thr Leu Ser Ser
            180                 185                 190

Pro Asn Ser Lys Asn Glu Lys Ala Leu Gly Arg Lys Ile Asn Ser Trp
        195                 200                 205

Glu Ser Ser Arg Ser Gly His Ser Phe Leu Ser Asn Leu His Leu Arg
    210                 215                 220

Asn Gly Glu Leu Val Ile His Glu Lys Gly Phe Tyr Tyr Ile Tyr Ser
225                 230                 235                 240

Gln Thr Tyr Phe Arg Phe Gln Glu Glu Ile Lys Glu Asn Thr Lys Asn
                245                 250                 255

Asp Lys Gln Met Val Gln Tyr Ile Tyr Lys Tyr Thr Ser Tyr Pro Asp
            260                 265                 270

Pro Ile Leu Leu Met Lys Ser Ala Arg Asn Ser Cys Trp Ser Lys Asp
        275                 280                 285

Ala Glu Tyr Gly Leu Tyr Ser Ile Tyr Gln Gly Gly Ile Phe Glu Leu
    290                 295                 300

Lys Glu Asn Asp Arg Ile Phe Val Ser Val Thr Asn Glu His Leu Ile
305                 310                 315                 320

Asp Met Asp His Glu Ala Ser Phe Phe Gly Ala Phe Leu Val Gly Ser
                325                 330                 335

Arg Glu Arg Gly Pro Gln Arg Val Ala Ala His Ile Thr Gly Thr Arg
            340                 345                 350

Gly Arg Ser Asn Thr Leu Ser Ser Pro Asn Ser Lys Asn Glu Lys Ala
        355                 360                 365

Leu Gly Arg Lys Ile Asn Ser Trp Glu Ser Ser Arg Ser Gly His Ser
    370                 375                 380

Phe Leu Ser Asn Leu His Leu Arg Asn Gly Glu Leu Val Ile His Glu
385                 390                 395                 400
```

```
Lys Gly Phe Tyr Tyr Ile Tyr Ser Gln Thr Tyr Phe Arg Phe Gln Glu
            405                 410                 415

Glu Ile Lys Glu Asn Thr Lys Asn Asp Lys Gln Met Val Gln Tyr Ile
        420                 425                 430

Tyr Lys Tyr Thr Ser Tyr Pro Asp Pro Ile Leu Leu Met Lys Ser Ala
        435                 440                 445

Arg Asn Ser Cys Trp Ser Lys Asp Ala Glu Tyr Gly Leu Tyr Ser Ile
        450                 455                 460

Tyr Gln Gly Gly Ile Phe Glu Leu Lys Glu Asn Asp Arg Ile Phe Val
465                 470                 475                 480

Ser Val Thr Asn Glu His Leu Ile Asp Met Asp His Glu Ala Ser Phe
                485                 490                 495

Phe Gly Ala Phe Leu Val Gly
            500
```

<210> SEQ ID NO 88
<211> LENGTH: 503
<212> TYPE: PRT
<213> ORGANISM: Artificial Sequence
<220> FEATURE:
<223> OTHER INFORMATION: Synthetic polypeptide

<400> SEQUENCE: 88

```
Arg Glu Arg Gly Pro Gln Arg Val Ala Ala His Ile Thr Gly Thr Arg
1               5                   10                  15

Gly Arg Ser Asn Thr Leu Ser Ser Pro Asn Ser Lys Asn Glu Lys Ala
            20                  25                  30

Leu Gly Arg Lys Ile Asn Ser Trp Glu Ser Ser Arg Ser Gly His Ser
        35                  40                  45

Phe Leu Ser Asn Leu His Leu Arg Asn Gly Glu Leu Val Ile His Glu
    50                  55                  60

Lys Gly Phe Tyr Tyr Ile Tyr Ser Gln Thr Tyr Phe Arg Phe Gln Glu
65                  70                  75                  80

Glu Ile Lys Glu Asn Thr Lys Asn Asp Lys Gln Met Val Gln Tyr Ile
                85                  90                  95

Tyr Lys Tyr Thr Ser Tyr Pro Asp Pro Ile Leu Leu Met Lys Ser Ala
            100                 105                 110

Arg Asn Ser Cys Trp Ser Lys Asp Ala Glu Tyr Gly Leu Tyr Ser Ile
        115                 120                 125

Tyr Gln Gly Gly Ile Phe Glu Leu Lys Glu Asn Asp Arg Ile Phe Val
    130                 135                 140

Ser Val Thr Asn Glu His Leu Ile Asp Met Asp His Glu Ala Ser Phe
145                 150                 155                 160

Phe Gly Ala Phe Leu Val Gly Ser Arg Glu Arg Gly Pro Gln Arg Val
                165                 170                 175

Ala Ala His Ile Thr Gly Thr Arg Gly Arg Ser Asn Thr Leu Ser Ser
            180                 185                 190

Pro Asn Ser Lys Asn Glu Lys Ala Leu Gly Arg Lys Ile Asn Ser Trp
        195                 200                 205

Glu Ser Ser Arg Ser Gly His Ser Phe Leu Ser Asn Leu His Leu Arg
    210                 215                 220

Asn Gly Glu Leu Val Ile His Glu Lys Gly Phe Tyr Tyr Ile Tyr Ser
225                 230                 235                 240

Gln Thr Tyr Phe Arg Phe Gln Glu Glu Ile Lys Glu Asn Thr Lys Asn
                245                 250                 255
```

```
Asp Lys Gln Met Val Gln Tyr Ile Tyr Lys Tyr Thr Ser Tyr Pro Asp
            260                 265                 270

Pro Ile Leu Leu Met Lys Ser Ala Arg Asn Ser Cys Trp Ser Lys Asp
            275                 280                 285

Ala Glu Tyr Gly Leu Tyr Ser Ile Tyr Gln Gly Gly Ile Phe Glu Leu
            290                 295                 300

Lys Glu Asn Asp Arg Ile Phe Val Ser Val Thr Asn Glu His Leu Ile
305                 310                 315                 320

Asp Met Asp His Glu Ala Ser Phe Phe Gly Ala Phe Leu Val Gly Ser
            325                 330                 335

Arg Glu Arg Gly Pro Gln Arg Val Ala Ala His Ile Thr Gly Thr Arg
            340                 345                 350

Gly Arg Ser Asn Thr Leu Ser Ser Pro Asn Ser Lys Asn Glu Lys Ala
            355                 360                 365

Leu Gly Arg Lys Ile Asn Ser Trp Glu Ser Ser Arg Ser Gly His Ser
            370                 375                 380

Phe Leu Ser Asn Leu His Leu Arg Asn Gly Glu Leu Val Ile His Glu
385                 390                 395                 400

Lys Gly Phe Tyr Tyr Ile Tyr Ser Gln Thr Tyr Phe Arg Phe Gln Glu
            405                 410                 415

Glu Ile Lys Glu Asn Thr Lys Asn Asp Lys Gln Met Val Gln Tyr Ile
            420                 425                 430

Tyr Lys Tyr Thr Ser Tyr Pro Asp Pro Ile Leu Leu Met Lys Ser Ala
            435                 440                 445

Arg Asn Ser Cys Trp Ser Lys Asp Ala Glu Tyr Gly Leu Tyr Ser Ile
            450                 455                 460

Tyr Gln Gly Gly Ile Phe Glu Leu Lys Glu Asn Asp Arg Ile Phe Val
465                 470                 475                 480

Ser Val Thr Asn Glu His Leu Ile Asp Met Asp His Glu Ala Ser Phe
            485                 490                 495

Phe Gly Ala Phe Leu Val Gly
            500

<210> SEQ ID NO 89
<211> LENGTH: 874
<212> TYPE: PRT
<213> ORGANISM: Artificial Sequence
<220> FEATURE:
<223> OTHER INFORMATION: Synthetic polypeptide

<400> SEQUENCE: 89

Met Ala Arg Ala Ser Gly Ser Glu Arg Leu Leu Leu Ile Tyr Thr
1               5                   10                  15

Gly Gly Thr Leu Gly Met Arg Ser Glu Gly Gly Val Leu Val Pro Gly
            20                  25                  30

Pro Gly Leu Val Thr Leu Leu Arg Thr Leu Pro Met Phe His Asp Glu
            35                  40                  45

Glu Phe Ala Arg Ala Arg Gly Leu Ser Glu Asp Thr Leu Val Leu Pro
    50                  55                  60

Pro Ala Ser His Gly Pro Arg Val Leu Tyr Thr Val Leu Glu Cys Gln
65                  70                  75                  80

Pro Leu Leu Asp Ser Ser Asp Met Thr Ile Ala Glu Trp Ile Arg Ile
            85                  90                  95

Ala Gln Ile Ile Lys Arg His Tyr Glu Gln Tyr His Gly Phe Val Val
            100                 105                 110
```

-continued

```
Ile His Gly Thr Asp Thr Met Ala Phe Ala Ala Ser Met Leu Ser Phe
    115                 120                 125

Met Leu Glu Asn Leu Gln Lys Pro Val Ile Leu Thr Gly Ala Gln Val
    130                 135                 140

Pro Ile His Val Leu Trp Asn Asp Ala Arg Glu Asn Leu Leu Gly Ala
145                 150                 155                 160

Leu Leu Val Ala Gly Gln Tyr Ile Ile Pro Glu Val Cys Leu Phe Met
                165                 170                 175

Asn Ser Gln Leu Phe Arg Gly Asn Arg Val Thr Lys Val Asp Ser Gln
                180                 185                 190

Arg Phe Glu Ala Phe Ala Ser Pro Asn Leu Ser Pro Leu Ala Thr Val
            195                 200                 205

Gly Ala Asp Val Thr Ile Ala Trp Glu Leu Val Arg Lys Val Lys Trp
        210                 215                 220

Lys Asp Pro Leu Val Val His Ser Ser Met Glu Gln Asp Val Ala Leu
225                 230                 235                 240

Leu Arg Leu Tyr Pro Gly Ile Pro Ala Ala Leu Val Arg Ala Phe Leu
                245                 250                 255

Gln Pro Pro Leu Lys Gly Val Val Leu Glu Thr Phe Gly Ser Gly Asn
                260                 265                 270

Gly Pro Ser Lys Pro Asp Leu Leu Gln Glu Leu Arg Ala Ala Ala Glu
            275                 280                 285

Arg Gly Leu Ile Met Val Asn Cys Ser Gln Cys Leu Gln Gly Ser Val
        290                 295                 300

Thr Pro Gly Tyr Ala Thr Ser Leu Ala Gly Ala Asn Ile Val Ser Gly
305                 310                 315                 320

Leu Asp Met Thr Ser Glu Ala Ala Leu Ala Lys Leu Ser Tyr Val Leu
                325                 330                 335

Gly Leu Pro Glu Leu Ser Leu Asp Arg Arg Gln Glu Leu Leu Ala Lys
                340                 345                 350

Asp Leu Arg Gly Glu Met Thr Pro Pro Ser Val Glu Glu Arg Arg Pro
            355                 360                 365

Ser Thr Ser Arg Glu Arg Gly Pro Gln Arg Val Ala Ala His Ile Thr
        370                 375                 380

Gly Thr Arg Gly Arg Ser Asn Thr Leu Ser Ser Pro Asn Ser Lys Asn
385                 390                 395                 400

Glu Lys Ala Leu Gly Arg Lys Ile Asn Ser Trp Glu Ser Ser Arg Ser
                405                 410                 415

Gly His Ser Phe Leu Ser Asn Leu His Leu Arg Asn Gly Glu Leu Val
                420                 425                 430

Ile His Glu Lys Gly Phe Tyr Tyr Ile Tyr Ser Gln Thr Tyr Phe Arg
            435                 440                 445

Phe Gln Glu Glu Ile Lys Glu Asn Thr Lys Asn Asp Lys Gln Met Val
        450                 455                 460

Gln Tyr Ile Tyr Lys Tyr Thr Ser Tyr Pro Asp Pro Ile Leu Leu Met
465                 470                 475                 480

Lys Ser Ala Arg Asn Ser Cys Trp Ser Lys Asp Ala Glu Tyr Gly Leu
                485                 490                 495

Tyr Ser Ile Tyr Gln Gly Gly Ile Phe Glu Leu Lys Glu Asn Asp Arg
                500                 505                 510

Ile Phe Val Ser Val Thr Asn Glu His Leu Ile Asp Met Asp His Glu
            515                 520                 525
```

```
Ala Ser Phe Phe Gly Ala Phe Leu Val Gly Gly Arg Glu Arg Gly Pro
        530                 535                 540

Gln Arg Val Ala Ala His Ile Thr Gly Thr Arg Gly Arg Ser Asn Thr
545                 550                 555                 560

Leu Ser Ser Pro Asn Ser Lys Asn Glu Lys Ala Leu Gly Arg Lys Ile
                565                 570                 575

Asn Ser Trp Glu Ser Ser Arg Ser Gly His Ser Phe Leu Ser Asn Leu
            580                 585                 590

His Leu Arg Asn Gly Glu Leu Val Ile His Glu Lys Gly Phe Tyr Tyr
        595                 600                 605

Ile Tyr Ser Gln Thr Tyr Phe Arg Phe Gln Glu Ile Lys Glu Asn
610                 615                 620

Thr Lys Asn Asp Lys Gln Met Val Gln Tyr Ile Tyr Lys Tyr Thr Ser
625                 630                 635                 640

Tyr Pro Asp Pro Ile Leu Leu Met Lys Ser Ala Arg Asn Ser Cys Trp
                645                 650                 655

Ser Lys Asp Ala Glu Tyr Gly Leu Tyr Ser Ile Tyr Gln Gly Gly Ile
            660                 665                 670

Phe Glu Leu Lys Glu Asn Asp Arg Ile Phe Val Ser Val Thr Asn Glu
        675                 680                 685

His Leu Ile Asp Met Asp His Glu Ala Ser Phe Phe Gly Ala Phe Leu
    690                 695                 700

Val Gly Ser Arg Glu Arg Gly Pro Gln Arg Val Ala Ala His Ile Thr
705                 710                 715                 720

Gly Thr Arg Gly Arg Ser Asn Thr Leu Ser Ser Pro Asn Ser Lys Asn
                725                 730                 735

Glu Lys Ala Leu Gly Arg Lys Ile Asn Ser Trp Glu Ser Ser Arg Ser
            740                 745                 750

Gly His Ser Phe Leu Ser Asn Leu His Leu Arg Asn Gly Glu Leu Val
        755                 760                 765

Ile His Glu Lys Gly Phe Tyr Tyr Ile Tyr Ser Gln Thr Tyr Phe Arg
    770                 775                 780

Phe Gln Glu Glu Ile Lys Glu Asn Thr Lys Asn Asp Lys Gln Met Val
785                 790                 795                 800

Gln Tyr Ile Tyr Lys Tyr Thr Ser Tyr Pro Asp Pro Ile Leu Leu Met
                805                 810                 815

Lys Ser Ala Arg Asn Ser Cys Trp Ser Lys Asp Ala Glu Tyr Gly Leu
            820                 825                 830

Tyr Ser Ile Tyr Gln Gly Gly Ile Phe Glu Leu Lys Glu Asn Asp Arg
        835                 840                 845

Ile Phe Val Ser Val Thr Asn Glu His Leu Ile Asp Met Asp His Glu
850                 855                 860

Ala Ser Phe Phe Gly Ala Phe Leu Val Gly
865                 870

<210> SEQ ID NO 90
<211> LENGTH: 883
<212> TYPE: PRT
<213> ORGANISM: Artificial Sequence
<220> FEATURE:
<223> OTHER INFORMATION: Synthetic polypeptide

<400> SEQUENCE: 90

Ser Glu Arg Arg Leu Leu Leu Ile Tyr Thr Gly Gly Thr Leu Gly Met
1               5                   10                  15
```

-continued

Arg Ser Glu Gly Gly Val Leu Val Pro Gly Leu Val Thr Leu
          20                  25                  30

Leu Arg Thr Leu Pro Met Phe His Asp Glu Glu Phe Ala Arg Ala Arg
         35                  40                  45

Gly Leu Ser Glu Asp Thr Leu Val Leu Pro Pro Ala Ser His Gly Pro
     50                  55                  60

Arg Val Leu Tyr Thr Val Leu Glu Cys Gln Pro Leu Leu Asp Ser Ser
65                  70                  75                  80

Asp Met Thr Ile Ala Glu Trp Ile Arg Ile Ala Gln Ile Ile Lys Arg
                85                  90                  95

His Tyr Glu Gln Tyr His Gly Phe Val Val Ile His Gly Thr Asp Thr
             100                 105                 110

Met Ala Phe Ala Ala Ser Met Leu Ser Phe Met Leu Glu Asn Leu Gln
         115                 120                 125

Lys Pro Val Ile Leu Thr Gly Ala Gln Val Pro Ile His Val Leu Trp
    130                 135                 140

Asn Asp Ala Arg Glu Asn Leu Leu Gly Ala Leu Leu Val Ala Gly Gln
145                 150                 155                 160

Tyr Ile Ile Pro Glu Val Cys Leu Phe Met Asn Ser Gln Leu Phe Arg
                165                 170                 175

Gly Asn Arg Val Thr Lys Val Asp Ser Gln Arg Phe Glu Ala Phe Ala
             180                 185                 190

Ser Pro Asn Leu Ser Pro Leu Ala Thr Val Gly Ala Asp Val Thr Ile
         195                 200                 205

Ala Trp Glu Leu Val Arg Lys Val Lys Trp Lys Asp Pro Leu Val Val
    210                 215                 220

His Ser Ser Met Glu Gln Asp Val Ala Leu Leu Arg Leu Tyr Pro Gly
225                 230                 235                 240

Ile Pro Ala Ala Leu Val Arg Ala Phe Leu Gln Pro Pro Leu Lys Gly
                245                 250                 255

Val Val Leu Glu Thr Phe Gly Ser Gly Asn Gly Pro Ser Lys Pro Asp
             260                 265                 270

Leu Leu Gln Glu Leu Arg Ala Ala Ala Glu Arg Gly Leu Ile Met Val
         275                 280                 285

Asn Cys Ser Gln Cys Leu Gln Gly Ser Val Thr Pro Gly Tyr Ala Thr
    290                 295                 300

Ser Leu Ala Gly Ala Asn Ile Val Ser Gly Leu Asp Met Thr Ser Glu
305                 310                 315                 320

Ala Ala Leu Ala Lys Leu Ser Tyr Val Leu Gly Leu Pro Glu Leu Ser
                325                 330                 335

Leu Asp Arg Arg Gln Glu Leu Leu Ala Lys Asp Leu Arg Gly Glu Met
             340                 345                 350

Thr Pro Pro Ser Val Glu Glu Arg Pro Ser Leu Gln Gly Asn Thr
         355                 360                 365

Leu Gly Gly Gly Val Ser Trp Leu Leu Ser Thr Ser Arg Glu Arg Gly
    370                 375                 380

Pro Gln Arg Val Ala Ala His Ile Thr Gly Thr Arg Gly Arg Ser Asn
385                 390                 395                 400

Thr Leu Ser Ser Pro Asn Ser Lys Asn Glu Lys Ala Leu Gly Arg Lys
                405                 410                 415

Ile Asn Ser Trp Glu Ser Ser Arg Ser Gly His Ser Phe Leu Ser Asn
             420                 425                 430

Leu His Leu Arg Asn Gly Glu Leu Val Ile His Glu Lys Gly Phe Tyr

```
                435                 440                 445
Tyr Ile Tyr Ser Gln Thr Tyr Phe Arg Phe Gln Glu Glu Ile Lys Glu
450                 455                 460

Asn Thr Lys Asn Asp Lys Gln Met Val Gln Tyr Ile Tyr Lys Tyr Thr
465                 470                 475                 480

Ser Tyr Pro Asp Pro Ile Leu Leu Met Lys Ser Ala Arg Asn Ser Cys
                485                 490                 495

Trp Ser Lys Asp Ala Glu Tyr Gly Leu Tyr Ser Ile Tyr Gln Gly Gly
                500                 505                 510

Ile Phe Glu Leu Lys Glu Asn Asp Arg Ile Phe Val Ser Val Thr Asn
                515                 520                 525

Glu His Leu Ile Asp Met Asp His Glu Ala Ser Phe Phe Gly Ala Phe
                530                 535                 540

Leu Val Gly Ser Arg Glu Arg Gly Pro Gln Arg Val Ala Ala His Ile
545                 550                 555                 560

Thr Gly Thr Arg Gly Arg Ser Asn Thr Leu Ser Ser Pro Asn Ser Lys
                565                 570                 575

Asn Glu Lys Ala Leu Gly Arg Lys Ile Asn Ser Trp Glu Ser Ser Arg
                580                 585                 590

Ser Gly His Ser Phe Leu Ser Asn Leu His Leu Arg Asn Gly Glu Leu
                595                 600                 605

Val Ile His Glu Lys Gly Phe Tyr Tyr Ile Tyr Ser Gln Thr Tyr Phe
610                 615                 620

Arg Phe Gln Glu Glu Ile Lys Glu Asn Thr Lys Asn Asp Lys Gln Met
625                 630                 635                 640

Val Gln Tyr Ile Tyr Lys Tyr Thr Ser Tyr Pro Asp Pro Ile Leu Leu
                645                 650                 655

Met Lys Ser Ala Arg Asn Ser Cys Trp Ser Lys Asp Ala Glu Tyr Gly
                660                 665                 670

Leu Tyr Ser Ile Tyr Gln Gly Gly Ile Phe Glu Leu Lys Glu Asn Asp
                675                 680                 685

Arg Ile Phe Val Ser Val Thr Asn Glu His Leu Ile Asp Met Asp His
690                 695                 700

Glu Ala Ser Phe Phe Gly Ala Phe Leu Val Gly Ser Arg Glu Arg Gly
705                 710                 715                 720

Pro Gln Arg Val Ala Ala His Ile Thr Gly Thr Arg Gly Arg Ser Asn
                725                 730                 735

Thr Leu Ser Ser Pro Asn Ser Lys Asn Glu Lys Ala Leu Gly Arg Lys
                740                 745                 750

Ile Asn Ser Trp Glu Ser Ser Arg Ser Gly His Ser Phe Leu Ser Asn
                755                 760                 765

Leu His Leu Arg Asn Gly Glu Leu Val Ile His Glu Lys Gly Phe Tyr
                770                 775                 780

Tyr Ile Tyr Ser Gln Thr Tyr Phe Arg Phe Gln Glu Glu Ile Lys Glu
785                 790                 795                 800

Asn Thr Lys Asn Asp Lys Gln Met Val Gln Tyr Ile Tyr Lys Tyr Thr
                805                 810                 815

Ser Tyr Pro Asp Pro Ile Leu Leu Met Lys Ser Ala Arg Asn Ser Cys
                820                 825                 830

Trp Ser Lys Asp Ala Glu Tyr Gly Leu Tyr Ser Ile Tyr Gln Gly Gly
                835                 840                 845

Ile Phe Glu Leu Lys Glu Asn Asp Arg Ile Phe Val Ser Val Thr Asn
850                 855                 860
```

Glu His Leu Ile Asp Met Asp His Glu Ala Ser Phe Phe Gly Ala Phe
865                 870                 875                 880

Leu Val Gly

<210> SEQ ID NO 91
<211> LENGTH: 872
<212> TYPE: PRT
<213> ORGANISM: Artificial Sequence
<220> FEATURE:
<223> OTHER INFORMATION: Synthetic polypeptide

<400> SEQUENCE: 91

Arg Glu Arg Gly Pro Gln Arg Val Ala Ala His Ile Thr Gly Thr Arg
1               5                   10                  15

Gly Arg Ser Asn Thr Leu Ser Ser Pro Asn Ser Lys Asn Glu Lys Ala
            20                  25                  30

Leu Gly Arg Lys Ile Asn Ser Trp Glu Ser Ser Arg Ser Gly His Ser
        35                  40                  45

Phe Leu Ser Asn Leu His Leu Arg Asn Gly Glu Leu Val Ile His Glu
    50                  55                  60

Lys Gly Phe Tyr Tyr Ile Tyr Ser Gln Thr Tyr Phe Arg Phe Gln Glu
65                  70                  75                  80

Glu Ile Lys Glu Asn Thr Lys Asn Asp Lys Gln Met Val Gln Tyr Ile
                85                  90                  95

Tyr Lys Tyr Thr Ser Tyr Pro Asp Pro Ile Leu Leu Met Lys Ser Ala
            100                 105                 110

Arg Asn Ser Cys Trp Ser Lys Asp Ala Glu Tyr Gly Leu Tyr Ser Ile
        115                 120                 125

Tyr Gln Gly Gly Ile Phe Glu Leu Lys Glu Asn Asp Arg Ile Phe Val
    130                 135                 140

Ser Val Thr Asn Glu His Leu Ile Asp Met Asp His Glu Ala Ser Phe
145                 150                 155                 160

Phe Gly Ala Phe Leu Val Gly Ser Arg Glu Arg Gly Pro Gln Arg Val
                165                 170                 175

Ala Ala His Ile Thr Gly Thr Arg Gly Arg Ser Asn Thr Leu Ser Ser
            180                 185                 190

Pro Asn Ser Lys Asn Glu Lys Ala Leu Gly Arg Lys Ile Asn Ser Trp
        195                 200                 205

Glu Ser Ser Arg Ser Gly His Ser Phe Leu Ser Asn Leu His Leu Arg
    210                 215                 220

Asn Gly Glu Leu Val Ile His Glu Lys Gly Phe Tyr Tyr Ile Tyr Ser
225                 230                 235                 240

Gln Thr Tyr Phe Arg Phe Gln Glu Glu Ile Lys Glu Asn Thr Lys Asn
                245                 250                 255

Asp Lys Gln Met Val Gln Tyr Ile Tyr Lys Tyr Thr Ser Tyr Pro Asp
            260                 265                 270

Pro Ile Leu Leu Met Lys Ser Ala Arg Asn Ser Cys Trp Ser Lys Asp
        275                 280                 285

Ala Glu Tyr Gly Leu Tyr Ser Ile Tyr Gln Gly Gly Ile Phe Glu Leu
    290                 295                 300

Lys Glu Asn Asp Arg Ile Phe Val Ser Val Thr Asn Glu His Leu Ile
305                 310                 315                 320

Asp Met Asp His Glu Ala Ser Phe Phe Gly Ala Phe Leu Val Gly Ser
                325                 330                 335

```
Arg Glu Arg Gly Pro Gln Arg Val Ala Ala His Ile Thr Gly Thr Arg
            340                 345                 350

Gly Arg Ser Asn Thr Leu Ser Ser Pro Asn Ser Lys Asn Glu Lys Ala
        355                 360                 365

Leu Gly Arg Lys Ile Asn Ser Trp Glu Ser Ser Arg Ser Gly His Ser
370                 375                 380

Phe Leu Ser Asn Leu His Leu Arg Asn Gly Glu Leu Val Ile His Glu
385                 390                 395                 400

Lys Gly Phe Tyr Tyr Ile Tyr Ser Gln Thr Tyr Phe Arg Phe Gln Glu
                405                 410                 415

Glu Ile Lys Glu Asn Thr Lys Asn Asp Lys Gln Met Val Gln Tyr Ile
            420                 425                 430

Tyr Lys Tyr Thr Ser Tyr Pro Asp Pro Ile Leu Leu Met Lys Ser Ala
        435                 440                 445

Arg Asn Ser Cys Trp Ser Lys Asp Ala Glu Tyr Gly Leu Tyr Ser Ile
450                 455                 460

Tyr Gln Gly Gly Ile Phe Glu Leu Lys Glu Asn Asp Arg Ile Phe Val
465                 470                 475                 480

Ser Val Thr Asn Glu His Leu Ile Asp Met Asp His Glu Ala Ser Phe
                485                 490                 495

Phe Gly Ala Phe Leu Val Gly Met Ala Arg Ala Ser Gly Ser Glu Arg
            500                 505                 510

Arg Leu Leu Leu Ile Tyr Thr Gly Thr Leu Gly Met Arg Ser Glu
        515                 520                 525

Gly Gly Val Leu Val Pro Gly Pro Gly Leu Val Thr Leu Leu Arg Thr
530                 535                 540

Leu Pro Met Phe His Asp Glu Glu Phe Ala Arg Ala Arg Gly Leu Ser
545                 550                 555                 560

Glu Asp Thr Leu Val Leu Pro Pro Ala Ser His Gly Pro Arg Val Leu
                565                 570                 575

Tyr Thr Val Leu Glu Cys Gln Pro Leu Leu Asp Ser Ser Asp Met Thr
            580                 585                 590

Ile Ala Glu Trp Ile Arg Ile Ala Gln Ile Ile Lys Arg His Tyr Glu
        595                 600                 605

Gln Tyr His Gly Phe Val Val Ile His Gly Thr Asp Thr Met Ala Phe
610                 615                 620

Ala Ala Ser Met Leu Ser Phe Met Leu Glu Asn Leu Gln Lys Pro Val
625                 630                 635                 640

Ile Leu Thr Gly Ala Gln Val Pro Ile His Val Leu Trp Asn Asp Ala
                645                 650                 655

Arg Glu Asn Leu Leu Gly Ala Leu Leu Val Ala Gly Gln Tyr Ile Ile
            660                 665                 670

Pro Glu Val Cys Leu Phe Met Asn Ser Gln Leu Phe Arg Gly Asn Arg
        675                 680                 685

Val Thr Lys Val Asp Ser Gln Arg Phe Glu Ala Phe Ala Ser Pro Asn
690                 695                 700

Leu Ser Pro Leu Ala Thr Val Gly Ala Asp Val Thr Ile Ala Trp Glu
705                 710                 715                 720

Leu Val Arg Lys Val Lys Trp Lys Asp Pro Leu Val Val His Ser Ser
                725                 730                 735

Met Glu Gln Asp Val Ala Leu Leu Arg Leu Tyr Pro Gly Ile Pro Ala
            740                 745                 750

Ala Leu Val Arg Ala Phe Leu Gln Pro Pro Leu Lys Gly Val Val Leu
```

```
                    755                 760                 765
Glu Thr Phe Gly Ser Gly Asn Gly Pro Ser Lys Pro Asp Leu Leu Gln
770                 775                 780

Glu Leu Arg Ala Ala Glu Arg Gly Leu Ile Met Val Asn Cys Ser
785                 790                 795                 800

Gln Cys Leu Gln Gly Ser Val Thr Pro Gly Tyr Ala Thr Ser Leu Ala
                    805                 810                 815

Gly Ala Asn Ile Val Ser Gly Leu Asp Met Thr Ser Glu Ala Ala Leu
                820                 825                 830

Ala Lys Leu Ser Tyr Val Leu Gly Leu Pro Glu Leu Ser Leu Asp Arg
            835                 840                 845

Arg Gln Glu Leu Leu Ala Lys Asp Leu Arg Gly Glu Met Thr Pro Pro
        850                 855                 860

Ser Val Glu Glu Arg Arg Pro Ser
865                 870
```

<210> SEQ ID NO 92
<211> LENGTH: 891
<212> TYPE: PRT
<213> ORGANISM: Artificial Sequence
<220> FEATURE:
<223> OTHER INFORMATION: Synthetic polypeptide

<400> SEQUENCE: 92

```
Arg Glu Arg Gly Pro Gln Arg Val Ala Ala His Ile Thr Gly Thr Arg
1               5                   10                  15

Gly Arg Ser Asn Thr Leu Ser Ser Pro Asn Ser Lys Asn Glu Lys Ala
            20                  25                  30

Leu Gly Arg Lys Ile Asn Ser Trp Glu Ser Ser Arg Ser Gly His Ser
        35                  40                  45

Phe Leu Ser Asn Leu His Leu Arg Asn Gly Glu Leu Val Ile His Glu
    50                  55                  60

Lys Gly Phe Tyr Tyr Ile Tyr Ser Gln Thr Tyr Phe Arg Phe Gln Glu
65                  70                  75                  80

Glu Ile Lys Glu Asn Thr Lys Asn Asp Lys Gln Met Val Gln Tyr Ile
                85                  90                  95

Tyr Lys Tyr Thr Ser Tyr Pro Asp Pro Ile Leu Leu Met Lys Ser Ala
            100                 105                 110

Arg Asn Ser Cys Trp Ser Lys Asp Ala Glu Tyr Gly Leu Tyr Ser Ile
        115                 120                 125

Tyr Gln Gly Gly Ile Phe Glu Leu Lys Glu Asn Asp Arg Ile Phe Val
    130                 135                 140

Ser Val Thr Asn Glu His Leu Ile Asp Met Asp His Glu Ala Ser Phe
145                 150                 155                 160

Phe Gly Ala Phe Leu Val Gly Ser Arg Glu Arg Gly Pro Gln Arg Val
                165                 170                 175

Ala Ala His Ile Thr Gly Thr Arg Gly Arg Ser Asn Thr Leu Ser Ser
            180                 185                 190

Pro Asn Ser Lys Asn Glu Lys Ala Leu Gly Arg Lys Ile Asn Ser Trp
        195                 200                 205

Glu Ser Ser Arg Ser Gly His Ser Phe Leu Ser Asn Leu His Leu Arg
    210                 215                 220

Asn Gly Glu Leu Val Ile His Glu Lys Gly Phe Tyr Tyr Ile Tyr Ser
225                 230                 235                 240

Gln Thr Tyr Phe Arg Phe Gln Glu Glu Ile Lys Glu Asn Thr Lys Asn
```

-continued

```
                245                 250                 255
Asp Lys Gln Met Val Gln Tyr Ile Tyr Lys Tyr Thr Ser Tyr Pro Asp
                260                 265                 270
Pro Ile Leu Leu Met Lys Ser Ala Arg Asn Ser Cys Trp Ser Lys Asp
            275                 280                 285
Ala Glu Tyr Gly Leu Tyr Ser Ile Tyr Gln Gly Gly Ile Phe Glu Leu
        290                 295                 300
Lys Glu Asn Asp Arg Ile Phe Val Ser Val Thr Asn Glu His Leu Ile
305                 310                 315                 320
Asp Met Asp His Glu Ala Ser Phe Phe Gly Ala Phe Leu Val Gly Ser
                325                 330                 335
Arg Glu Arg Gly Pro Gln Arg Val Ala Ala His Ile Thr Gly Thr Arg
                340                 345                 350
Gly Arg Ser Asn Thr Leu Ser Ser Pro Asn Ser Lys Asn Glu Lys Ala
            355                 360                 365
Leu Gly Arg Lys Ile Asn Ser Trp Glu Ser Ser Arg Ser Gly His Ser
        370                 375                 380
Phe Leu Ser Asn Leu His Leu Arg Asn Gly Glu Leu Val Ile His Glu
385                 390                 395                 400
Lys Gly Phe Tyr Tyr Ile Tyr Ser Gln Thr Tyr Phe Arg Phe Gln Glu
                405                 410                 415
Glu Ile Lys Glu Asn Thr Lys Asn Asp Lys Gln Met Val Gln Tyr Ile
                420                 425                 430
Tyr Lys Tyr Thr Ser Tyr Pro Asp Pro Ile Leu Leu Met Lys Ser Ala
            435                 440                 445
Arg Asn Ser Cys Trp Ser Lys Asp Ala Glu Tyr Gly Leu Tyr Ser Ile
        450                 455                 460
Tyr Gln Gly Gly Ile Phe Glu Leu Lys Glu Asn Asp Arg Ile Phe Val
465                 470                 475                 480
Ser Val Thr Asn Glu His Leu Ile Asp Met Asp His Glu Ala Ser Phe
                485                 490                 495
Phe Gly Ala Phe Leu Val Gly Ser Gly Ser Gly Ser Gly Ser Gly Ser
                500                 505                 510
Gly Ser Gly Ser Gly Ser Gly Ser Gly Ser Met Ala Arg Ala Ser Gly
            515                 520                 525
Ser Glu Arg Arg Leu Leu Leu Ile Tyr Thr Gly Thr Leu Gly Met
        530                 535                 540
Arg Ser Glu Gly Gly Val Leu Val Pro Gly Pro Gly Leu Val Thr Leu
545                 550                 555                 560
Leu Arg Thr Leu Pro Met Phe His Asp Glu Glu Phe Ala Arg Ala Arg
                565                 570                 575
Gly Leu Ser Glu Asp Thr Leu Val Leu Pro Pro Ala Ser His Gly Pro
            580                 585                 590
Arg Val Leu Tyr Thr Val Leu Glu Cys Gln Pro Leu Leu Asp Ser Ser
        595                 600                 605
Asp Met Thr Ile Ala Glu Trp Ile Arg Ile Ala Gln Ile Ile Lys Arg
        610                 615                 620
His Tyr Glu Gln Tyr His Gly Phe Val Val Ile His Gly Thr Asp Thr
625                 630                 635                 640
Met Ala Phe Ala Ala Ser Met Leu Ser Phe Met Leu Glu Asn Leu Gln
                645                 650                 655
Lys Pro Val Ile Leu Thr Gly Ala Gln Val Pro Ile His Val Leu Trp
            660                 665                 670
```

Asn Asp Ala Arg Glu Asn Leu Leu Gly Ala Leu Leu Val Ala Gly Gln
                675                 680                 685

Tyr Ile Ile Pro Glu Val Cys Leu Phe Met Asn Ser Gln Leu Phe Arg
            690                 695                 700

Gly Asn Arg Val Thr Lys Val Asp Ser Gln Arg Phe Glu Ala Phe Ala
705                 710                 715                 720

Ser Pro Asn Leu Ser Pro Leu Ala Thr Val Gly Ala Asp Val Thr Ile
                725                 730                 735

Ala Trp Glu Leu Val Arg Lys Val Lys Trp Lys Asp Pro Leu Val Val
            740                 745                 750

His Ser Ser Met Glu Gln Asp Val Ala Leu Leu Arg Leu Tyr Pro Gly
                755                 760                 765

Ile Pro Ala Ala Leu Val Arg Ala Phe Leu Gln Pro Pro Leu Lys Gly
            770                 775                 780

Val Val Leu Glu Thr Phe Gly Ser Gly Asn Gly Pro Ser Lys Pro Asp
785                 790                 795                 800

Leu Leu Gln Glu Leu Arg Ala Ala Glu Arg Gly Leu Ile Met Val
                805                 810                 815

Asn Cys Ser Gln Cys Leu Gln Gly Ser Val Thr Pro Gly Tyr Ala Thr
            820                 825                 830

Ser Leu Ala Gly Ala Asn Ile Val Ser Gly Leu Asp Met Thr Ser Glu
                835                 840                 845

Ala Ala Leu Ala Lys Leu Ser Tyr Val Leu Gly Leu Pro Glu Leu Ser
            850                 855                 860

Leu Asp Arg Arg Gln Glu Leu Leu Ala Lys Asp Leu Arg Gly Glu Met
865                 870                 875                 880

Thr Pro Pro Ser Val Glu Glu Arg Arg Pro Ser
                885                 890

<210> SEQ ID NO 93
<211> LENGTH: 387
<212> TYPE: PRT
<213> ORGANISM: Artificial Sequence
<220> FEATURE:
<223> OTHER INFORMATION: Synthetic polypeptide

<400> SEQUENCE: 93

Met Ala Arg Ala Ser Gly Ser Glu Arg Arg Leu Leu Leu Ile Tyr Thr
1               5                   10                  15

Gly Gly Thr Leu Gly Met Arg Ser Glu Gly Gly Val Leu Val Pro Gly
            20                  25                  30

Pro Gly Leu Val Thr Leu Leu Arg Thr Leu Pro Met Phe His Asp Glu
        35                  40                  45

Glu Phe Ala Arg Ala Arg Gly Leu Ser Glu Asp Thr Leu Val Leu Pro
    50                  55                  60

Pro Ala Ser His Gly Pro Arg Val Leu Tyr Thr Val Leu Glu Cys Gln
65                  70                  75                  80

Pro Leu Leu Asp Ser Ser Asp Met Thr Ile Ala Glu Trp Ile Arg Ile
                85                  90                  95

Ala Gln Ile Ile Lys Arg His Tyr Glu Gln Tyr His Gly Phe Val Val
            100                 105                 110

Ile His Gly Thr Asp Thr Met Ala Phe Ala Ala Ser Met Leu Ser Phe
        115                 120                 125

Met Leu Glu Asn Leu Gln Lys Pro Val Ile Leu Thr Gly Ala Gln Val
    130                 135                 140

```
Pro Ile His Val Leu Trp Asn Asp Ala Arg Glu Asn Leu Leu Gly Ala
145                 150                 155                 160

Leu Leu Val Ala Gly Gln Tyr Ile Ile Pro Glu Val Cys Leu Phe Met
            165                 170                 175

Asn Ser Gln Leu Phe Arg Gly Asn Arg Val Thr Lys Val Asp Ser Gln
            180                 185                 190

Arg Phe Glu Ala Phe Ala Ser Pro Asn Leu Ser Pro Leu Ala Thr Val
        195                 200                 205

Gly Ala Asp Val Thr Ile Ala Trp Glu Leu Val Arg Lys Val Lys Trp
    210                 215                 220

Lys Arg Leu Ile Glu Asp Ile Cys Leu Pro Arg Trp Gly Cys Leu Trp
225                 230                 235                 240

Glu Asp Asp Pro Leu Val Val His Ser Ser Met Glu Gln Asp Val
                245                 250                 255

Ala Leu Leu Arg Leu Tyr Pro Gly Ile Pro Ala Ala Leu Val Arg Ala
            260                 265                 270

Phe Leu Gln Pro Pro Leu Lys Gly Val Val Leu Glu Thr Phe Gly Ser
        275                 280                 285

Gly Asn Gly Pro Ser Lys Pro Asp Leu Leu Gln Glu Leu Arg Ala Ala
    290                 295                 300

Ala Glu Arg Gly Leu Ile Met Val Asn Cys Ser Gln Cys Leu Gln Gly
305                 310                 315                 320

Ser Val Thr Pro Gly Tyr Ala Thr Ser Leu Ala Gly Ala Asn Ile Val
                325                 330                 335

Ser Gly Leu Asp Met Thr Ser Glu Ala Leu Ala Lys Leu Ser Tyr
            340                 345                 350

Val Leu Gly Leu Pro Glu Leu Ser Leu Asp Arg Arg Gln Glu Leu Leu
        355                 360                 365

Ala Lys Asp Leu Arg Gly Glu Met Thr Pro Pro Ser Val Glu Glu Arg
    370                 375                 380

Arg Pro Ser
385

<210> SEQ ID NO 94
<211> LENGTH: 387
<212> TYPE: PRT
<213> ORGANISM: Artificial Sequence
<220> FEATURE:
<223> OTHER INFORMATION: Synthetic polypeptide

<400> SEQUENCE: 94

Met Ala Arg Ala Ser Gly Ser Glu Arg Arg Leu Leu Leu Ile Tyr Thr
1               5                   10                  15

Gly Gly Thr Leu Gly Met Arg Ser Glu Gly Val Leu Val Pro Gly
            20                  25                  30

Pro Gly Leu Val Thr Leu Leu Arg Thr Leu Pro Met Phe His Asp Glu
        35                  40                  45

Glu Phe Ala Arg Ala Arg Gly Leu Ser Glu Asp Thr Leu Val Leu Pro
    50                  55                  60

Pro Ala Ser His Gly Pro Arg Val Leu Tyr Thr Val Leu Glu Cys Gln
65                  70                  75                  80

Pro Leu Leu Asp Ser Ser Asp Met Thr Ile Ala Glu Trp Ile Arg Ile
                85                  90                  95

Ala Gln Ile Ile Lys Arg His Tyr Glu Gln Tyr His Gly Phe Val Val
                100                 105                 110
```

-continued

```
Ile His Gly Thr Asp Thr Met Ala Phe Ala Ala Ser Met Leu Ser Phe
        115             120             125

Met Leu Glu Asn Leu Gln Lys Pro Val Ile Leu Thr Gly Ala Gln Val
        130             135             140

Pro Ile His Val Leu Trp Asn Asp Ala Arg Glu Asn Leu Leu Gly Ala
145             150             155             160

Leu Leu Val Ala Gly Gln Tyr Ile Ile Pro Glu Val Cys Leu Phe Met
                165             170             175

Asn Ser Gln Leu Phe Arg Gly Asn Arg Val Thr Lys Val Asp Ser Gln
            180             185             190

Arg Phe Glu Ala Phe Ala Ser Pro Asn Leu Ser Pro Leu Ala Thr Val
        195             200             205

Gly Ala Asp Val Thr Ile Ala Trp Glu Leu Val Arg Lys Val Lys Trp
210             215             220

Lys Asp Pro Leu Val Val His Ser Ser Met Glu Gln Asp Val Ala Leu
225             230             235             240

Leu Arg Leu Tyr Pro Gly Ile Pro Ala Ala Leu Val Arg Ala Phe Leu
                245             250             255

Gln Pro Pro Leu Lys Gly Val Val Leu Glu Thr Phe Gly Ser Gly Asn
            260             265             270

Gly Pro Ser Lys Pro Asp Leu Leu Gln Glu Leu Arg Ala Ala Ala Glu
            275             280             285

Arg Gly Leu Ile Met Val Asn Cys Ser Gln Cys Leu Gln Gly Ser Val
        290             295             300

Thr Pro Gly Tyr Ala Thr Ser Leu Ala Gly Ala Asn Ile Val Ser Gly
305             310             315             320

Leu Asp Met Thr Ser Glu Ala Ala Leu Ala Lys Leu Ser Tyr Val Leu
            325             330             335

Gly Leu Pro Glu Arg Leu Ile Glu Asp Ile Cys Leu Pro Arg Trp Gly
            340             345             350

Cys Leu Trp Glu Asp Asp Leu Ser Leu Asp Arg Arg Gln Glu Leu Leu
        355             360             365

Ala Lys Asp Leu Arg Gly Glu Met Thr Pro Pro Ser Val Glu Glu Arg
    370             375             380

Arg Pro Ser
385
```